US006130320A

United States Patent [19]

[11] Patent Number: 6,130,320

Lamm et al.

[45] Date of Patent: Oct. 10, 2000

[54] ACID DISAZO DYES AS WELL AS SULPHONAMIDES AS THEIR INTERMEDIATE PRODUCT

[75] Inventors: Gunther Lamm, Hassloch; Helmut Reichelt, Neustadt; Gerhard Wagenblast, Wachenheim, all of Germany

[73] Assignee: BASF Aktiengesellschaft, Ludwigshafen, Germany

[21] Appl. No.: 09/101,777

[22] PCT Filed: Jan. 16, 1997

[86] PCT No.: PCT/EP97/00174

§ 371 Date: Jul. 22, 1998

§ 102(e) Date: Jul. 22, 1998

[87] PCT Pub. No.: WO97/27248

PCT Pub. Date: Jul. 31, 1997

[30] Foreign Application Priority Data

Jan. 25, 1996 [DE] Germany ........................... 196 02 542

[51] Int. Cl.[7] ......................... C09B 62/513; C09B 31/10

[52] U.S. Cl. ......................... 534/642; 534/654; 534/797; 534/819; 8/549; 8/681

[58] Field of Search .................................... 534/642, 654, 534/797, 819; 8/549, 681

[56] References Cited

FOREIGN PATENT DOCUMENTS

| | | |
|---|---|---|
| 0 043 560 | 1/1982 | European Pat. Off. . |
| 0 048 692 | 3/1982 | European Pat. Off. . |
| 0 559 617 | 2/1993 | European Pat. Off. . |
| 739 468 | 1/1933 | France . |
| 1 558 340 | 2/1969 | France . |
| 1558679 | 2/1969 | France . |
| 34 20 467 | 6/1984 | Germany . |
| 65 651 | 11/1992 | Germany . |
| 195 30 176 | 8/1995 | Germany . |
| 192 048 | 10/1937 | Switzerland . |
| 192 049 | 10/1937 | Switzerland . |
| 192 050 | 10/1937 | Switzerland . |
| 92 14791 | 9/1992 | WIPO . |

OTHER PUBLICATIONS

Dyes and Pigments 24 (1994) 125–141, Elsevier Science Limited, England, Printed in Great Britain.

Chemical Abstracts, vol. 99, No. 4, Jul. 25, 1983, Abs. No. 23999r, "disazo reactive dyes".

*Primary Examiner*—Fiona T. Powers

*Attorney, Agent, or Firm*—Oblon, Spivak, McClelland, Maier & Neustadt, P.C.

[57] ABSTRACT

(I)

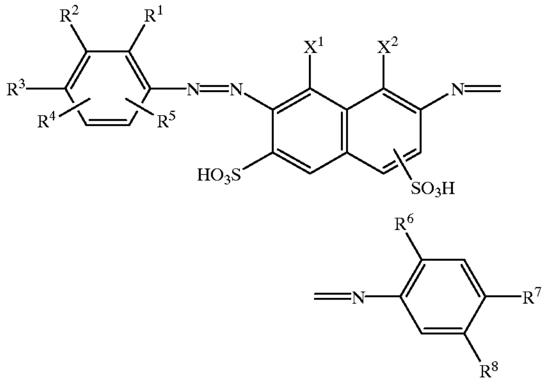

Disazo dyes of formula (I) where one of the two symbols $X^1$ and $X^2$ means hydroxy and the other amino and $R^1$, $R^2$, $R^3$, $R^4$, $R^5$, $R^6$, $R^7$ and $R^8$ are as defined in the specification. The invention also relates to sulphonamides as their intermediate products and to the use of the dyes for the dyeing of natural and synthetic substrates.

13 Claims, No Drawings

ACID DISAZO DYES AS WELL AS SULPHONAMIDES AS THEIR INTERMEDIATE PRODUCT

This application is a 371 of PCT/EP97/00174 filed Jan. 16, 1997.

The present invention relates to novel disazo dyes of the formula I (I)

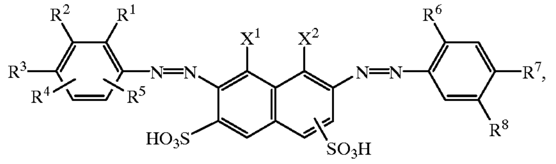

where one of the two radicals $X^1$ and $X^2$ is hydroxyl and the other is amino, $R^1$ is hydrogen, hydroxysulfonyl or a radical of the formula CO—Ar, CO—Alk, $SO_2$—Ar, $SO_2$—Alk, $SO_2$—OAr,

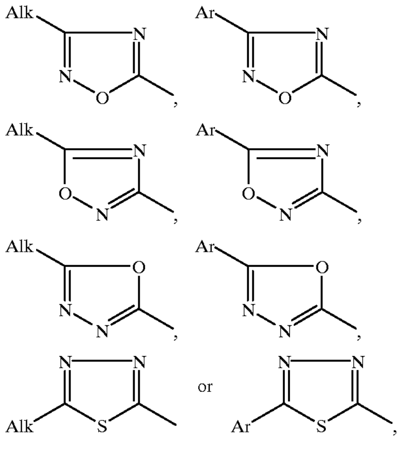

, , , , , , or , $R^2$ is hydrogen or $R^2$ and $R^1$ together are a radical of the formula

CO—$NZ^1$—CO or

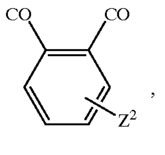

, $R^3$ is hydrogen, hydroxysulfonyl, $C_1$–$C_4$-alkyl, halogen or a radical of the formula $SO_2$—OAr, $SO_2$—N(Ar)Alk or $SO_2$—NHAr or $R^3$ and $R^2$ together are a radical of the formula CO—$NZ^1$—Y, $R^4$ is hydrogen, hydroxysulfonyl, pyrrolidinylsulfonyl, piperidinylsulfonyl, morpholinylsulfonyl or a radical of the formula CO—Ar, CO—OAlk, CO—NHAr, CO—N(Ar)Alk, CO—$N(Alk)_2$, $SO_2$—Alk, $SO_2$—OAr, $SO_2$—$N(Alk)_2$, $SO_2$—NHAlk, $SO_2$—N(Ar)Alk or $SO_2$—NHAr, $R^5$ is hydrogen, $C_1$–$C_4$-alkyl, halogen or hydroxysulfonyl, and $R^6$, $R^7$ and $R^8$ are each independently of the others hydrogen, $C_1$–$C_4$-alkyl, halogen, cyano, nitro, hydroxysulfonyl, pyrrolidinylsulfonyl, piperidinylsulfonyl, morpholinylsulfonyl or a radical of the formula CO—Ar, CO—OAr, CO—OAlk, CO—N(Ar)Alk, CO—$N(Alk)_2$, $SO_2$—Ar, $SO_2$—Alk, $SO_2$—$CH_2CH{=}CH_2$, $SO_2$—$CH{=}CH_2$, $SO_2$—$C_2H_4$—Q, $SO_2$—OAr, $SO_2$—$N(Alk)_2$, $SO_2$—NHAlk, $SO_2$—N(Ar)Alk, $SO_2$—NHAr,

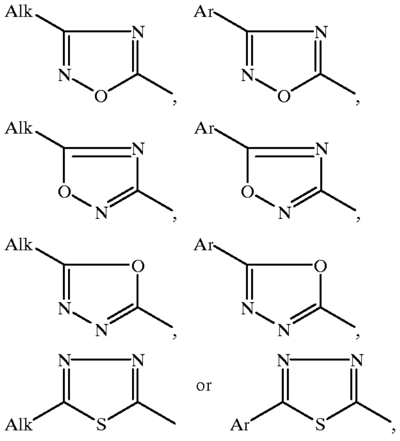

, , , , , , or , where

Alk is $C_1$–$C_8$-alkyl which may be interrupted by from 1 to 3 oxygen atoms in ether function or by 1 sulfur atom or 1 sulfonyl group and may be substituted by hydroxyl, $C_1$–$C_4$-alkanoyloxy, benzoyloxy, sulfato, halogen, cyano, carbamoyl, carboxyl, hydroxysulfonyl, phenoxy, phenyl or hydroxysulfonylphenyl, or is $C_5$–$C_8$-cycloalkyl, Ar is phenyl or naphthyl, and each of these radicals may be substituted by $C_1$–$C_4$-alkyl, phenyl-($C_1$–$C_4$)-alkyl, halogen, $C_1$–$C_4$-alkoxy, $C_1$–$C_4$-alkoxy-($C_1$–$C_4$)-alkyl, phenoxy, hydroxyl, carboxyl, $C_1$–$C_4$-alkanoylamino with or without interruption by 1 oxygen atom in ether function in the alkyl chain, benzoylamino, hydroxysulfonyl, pyrrolidinylsulfonyl, piperidinylsulfonyl, morpholinylsulfonyl or a radical of the formula $SO_2$—Alk, $SO_2$—$CH_2CH{=}CH_2$, $SO_2$—$CH{=}CH_2$, $SO_2$—$C_2H_4$—Q, $SO_2$—NHAlk, $SO_2$—$N(Alk)_2$, $SO_2$—G, $SO_2$—OG, $SO_2$—NHG or $SO_2$—N(Alk)G, Y is methylene or carbonyl, $Z^1$ is hydrogen or a radical of the formula Alk or Ar, $Z^2$ is hydrogen or hydroxysulfonyl, Q is hydroxyl or an alkali-detachable group, and G is phenyl which may be substituted by $C_1$–$C_4$-alkyl, carboxyl, hydroxysulfonyl or $C_1$–$C_4$-alkanoylamino or is naphthyl which may be substituted by hydroxysulfonyl, and at least one of the radicals $R^1$, $R^2$, $R^3$, $R^4$ or $R^5$ and at least one of the radicals $R^6$, $R^7$ or $R^8$ are not hydrogen, sulfonamides as their intermediates and also the use of the novel dyes for dyeing natural or synthetic substrates.

It is an object of the present invention to provide novel disazo-based acid dyes having advantageous application properties.

We have found that this object is achieved by the acid disazo dyes of the formula I defined at the beginning.

If $R^3$ and $R^2$ together are a radical of the formula CO—$NZ^1$—Y, this radical can be bonded to the ring positions of $R^2$ and $R^3$ via Y or CO, or vice versa.

Any alkyl appearing in the abovementioned formula I may be straight-chain or branched.

Any substituted alkyl appearing in the abovementioned formula generally contains 1 or 2 substituents.

Any alkyl appearing in the abovementioned formulae with interruption by oxygen atoms in ether function is preferably alkyl interrupted by 1 or 2 oxygen atoms in ether function.

Any substituted phenyl appearing in the abovementioned formulae generally contains from 1 to 3 substituents.

$R^3$, $R^5$, $R^6$, $R^7$, $R^8$ and Alk are each for example methyl, ethyl, propyl, isopropyl, butyl, isobutyl, sec-butyl, tert-butyl, fluorine, chlorine or bromine.

Alk may also be for example pentyl, isopentyl, neopentyl, tert-pentyl, hexyl, 2-methylpentyl, heptyl, 1-ethylpentyl, octyl, 2-ethylhexyl, isooctyl (the above designation isooctyl is a trivial name derived from the oxo process alcohols—cf. Ullmann's Encyclopedia of Industrial Chemistry, 5th Edition, Vol. A 1, pages 290 to 293, and Vol. A 10, pages 284 and 285), 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- or 4-butoxybutyl, 4,8-dioxadecyl, 3,6,9-trioxadecyl, 3,6,9-trioxaundecyl, 2-methylthioethyl, 2-ethylthioethyl, 2- or 3-methylthiopropyl, 2- or 3-ethylthiopropyl, 2- or 4-methylthiobutyl, 2- or 4-ethylthiobutyl, 2-methylsulfonylethyl, 2-ethylsulfonylethyl, 2- or 3-methylsulfonylpropyl, 2- or 3-ethylsulfonylpropyl, 2- or 4-methylsulfonylbutyl, 2- or 4-ethylsulfonylbutyl, chloromethyl, 2-chloroethyl, 2- or 3-chloropropyl, benzyl, 1- or 2-phenylethyl, 2-, 3- or 4-hydroxysulfonylbenzyl, 2-(2-,3- or 4-hydroxysulfonylphenyl)ethyl, 3-benzyloxypropyl, 2-hydroxyethyl, 2- or 3-hydroxypropyl, cyanomethyl, 2-cyanoethyl, 2- or 3-cyanopropyl, carbamoylmethyl, 2-carbamoylethyl, 2- or 3-carbamoylpropyl, 2-acetyloxyethyl, 2- or 3-acetyloxypropyl, 2-isobutyryloxyethyl, 2- or 3-isobutyryloxypropyl, carboxylmethyl, 2-carboxylethyl, 2- or 3-carboxylpropyl, hydroxysulfonylmethyl, 2-hydroxysulfonylethyl, 2- or 3-hydroxysulfonylpropyl, 2-sulfatoethyl or 2- or 3-sulfatopropyl.

Ar may also be for example phenyl, 2-, 3- or 4-methylphenyl, 2-, 3- or 4-ethylphenyl, 2-, 3- or 4-propylphenyl, 2-, 3- or 4-isopropylphenyl, 2-, 3- or 4-butylphenyl, 2,4-dimethylphenyl, 2-, 3- or 4-phenoxyphenyl, 2-, 3- or 4-methoxyphenyl, 2-, 3- or 4-ethoxyphenyl, 2-, 3- or 4-isobutoxyphenyl, 2,4-dimethoxyphenyl, 2-, 3- or 4-formylaminophenyl, 2-, 3- or 4-acetylaminophenyl, 2-, 3- or 4-propionylaminophenyl, 2-, 3- or 4-methoxyacetylaminophenyl, 2-, 3- or 4-chlorophenyl, 2-, 3- or 4-carboxyphenyl or 2-, 3- or 4-hydroxysulfonylphenyl, 2-, 3- or 4-benzoylaminophenyl, 2-, 3- or 4-pyrrolidinylsulfonylphenyl, 2-, 3- or 4-piperidinesulfonylphenyl, 2-, 3- or 4-morpholinylsulfonylphenyl, 2-, 3- or 4-methylsulfonylphenyl, 2-, 3- or 4-carboxymethylsulfonylphenyl, 2-, 3- or 4-vinylsulfonylphenyl, 2-, 3- or 4-(2-hydroxyethyl)sulfonylphenyl, 2-, 3- or 4-(2-sulfatoethyl)sulfonylphenyl, 2-, 3- or 4-ethylsulfamoylphenyl, 2-, 3- or 4-(2-hydroxyethyl)sulfamoylphenyl, 2-, 3- or 4-bis(2-hydroxyethyl)sulfamoylphenyl, naphth-1-yl, naphth-2-yl, 2-hydroxysulfonylnaphth-1-yl, 5-hydroxysulfonylnaphth-1-yl or 5-hydroxysulfonylnaphth-2-yl.

$Z^1$ is, as Alk may also be, for example cyclopentyl, cyclohexyl, cycloheptyl or cyclooctyl.

Q is hydroxyl or an alkali-detachable group. Such groups are for example chlorine, bromine, $C_1$–$C_4$-alkylsulfonyl, phenylsulfonyl, $OSO_3H$, $SSO_3H$, $OP(O)(OH)_2$, $C_1$–$C_4$-alkylsulfonyloxy, phenylsulfonyloxy, $C_1$–$C_4$-alkanoyloxy, $C_1$–$C_4$-dialkylamino, cyanoamino or a radical of the formula

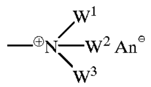,
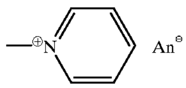,

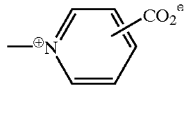
or
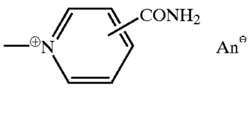, where $W^1$, $W^2$ and $W^3$ are each independently of the others $C_1$–$C_4$-alkyl or benzyl and $An^{\ominus}$ is in each case one equivalent of an anion. Suitable anions include for example fluoride, chloride, bromide, iodide, mono-, di- and trichloroacetate, methylsulfonate, phenylsulfonate or 2- or 4-methylphenylsulfonate.

$R^1$ and $R^4$ are each for example benzoyl, 2-, 3- or 4-methylbenzoyl, 2,3-, 2,4-, 2,5-, 2,6-, 3,4- or 3,5-dimethylbenzoyl, methoxycarbonyl, ethoxycarbonyl, propoxycarbonyl, isopropoxycarbonyl, butoxycarbonyl, methylsulfonyl, ethylsulfonyl, propylsulfonyl, isopropylsulfonyl or butylsulfonyl.

$R^1$ may also be for example 5-methyl-, 5-ethyl-, 5-propyl-, 5-butyl- or 5-phenyl-1,3,4-oxadiazol-2-yl, 3-methyl-, 3-ethyl-, 3-propyl-, 3-butyl- or 3-phenyl-1,2,4-oxadiazol-5-yl, phenylsulfonyl, 2-, 3- or 4-methylphenylsulfonyl or 2,3-, 2,4-, 2,5-, 2,6-, 3,4- or 3,5-dimethylphenylsulfonyl.

$R^3$, $R^6$, $R^7$ and $R^8$ are, as $R^1$ and $R^4$ may also be, for example phenoxysulfonyl or 2-, 3- or 4-methylphenoxysulfonyl.

$R^3$, $R^4$, $R^6$, $R^7$ and $R^8$ may each also be for example N-phenyl-N-methylsulfamoyl, N-phenyl-N-ethylsulfamoyl, N-phenyl-N-propylsulfamoyl, N-phenyl-N-butylsulfamoyl, phenylsulfamoyl or 2-, 3- or 4-methylphenylsulfamoyl.

$R^4$, $R^6$, $R^7$ and $R^8$ may each also be for example dimethylsulfamoyl, diethylsulfamoyl, dipropylsulfamoyl, dibutylsulfamoyl, N-methyl-N-ethylsulfamoyl, bis(2-hydroxyethyl)sulfamoyl, bis(carboxymethyl)sulfamoyl, bis(2-carboxyethyl)sulfamoyl, methylsulfamoyl, ethylsulfamoyl, propylsulfamoyl, isopropylsulfamoyl, butylsulfamoyl, 2-hydroxyethylsulfamoyl, carboxymethylsulfamoyl or 2-carboxyethylsulfamoyl.

$R^4$, $R^6$, $R^7$ and $R^8$ may each also be for example dimethylcarbamoyl, diethylcarbamoyl, dipropylcarbamoyl, dibutylcarbamoyl, N-methyl-N-ethylcarbamoyl, bis(2-hydroxyethyl)carbamoyl, bis(carboxymethyl)carbamoyl, bis(2-carboxyethyl)carbamoyl, N-phenyl-N-methylcarbamoyl, N-phenyl-N-ethylcarbamoyl, N-phenyl-N-propylcarbamoyl or N-phenyl-N-butylcarbamoyl.

$R^4$ may also be for example methylcarbamoyl, ethylcarbamoyl, propylcarbamoyl, isopropylcarbamoyl, butylcarbamoyl, 2-hydroxyethylcarbamoyl, carboxymethylcarbamoyl or 2-carboxyethylcarbamoyl.

$R^6$, $R^7$ and $R^8$ may each also be for example 2-hydroxyethylsulfonyl, 2-chloroethylsulfonyl, 2-sulfatoethylsulfonyl or 2-acetyloxyethylsulfonyl.

The radicals ($D^1$)

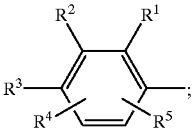

; and ($D^2$)

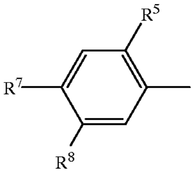

conform for example to the formulae

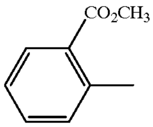

, ($D^1$)

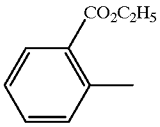

, ($D^1$)

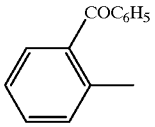

, ($D^1$)

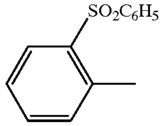

, ($D^1$)

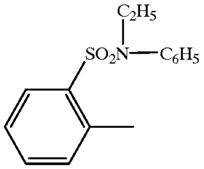

, ($D^1$)

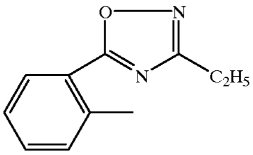

, ($D^1$)

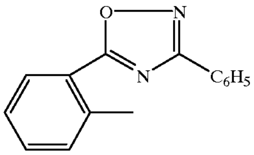

, ($D^1$)

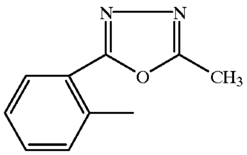

, ($D^1$)

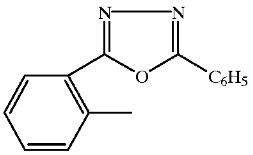

, ($D^1$)

-continued

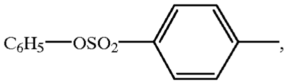

($D^1$)

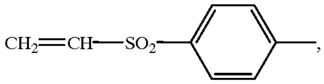

($D^2$)

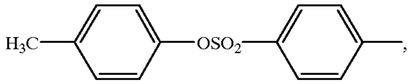

($D^1$)

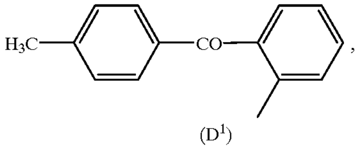

($D^1$)

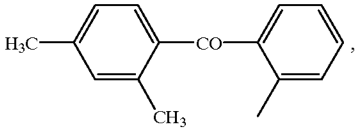

($D^1$)

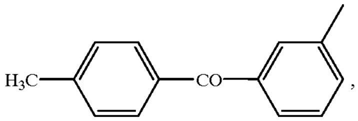

($D^1$)

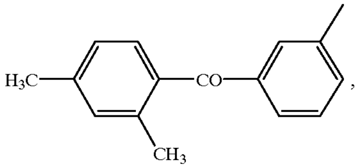

($D^1$)

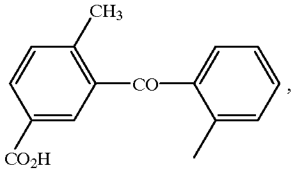

($D^1$)

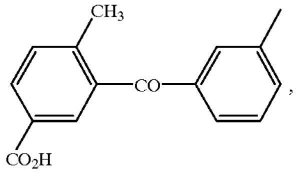

($D^1$)

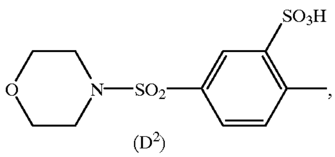

($D^2$)

-continued

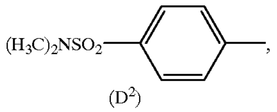

(D2)

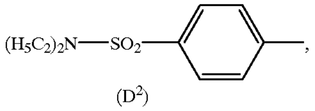

(D2)

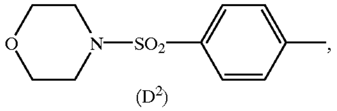

(D2)

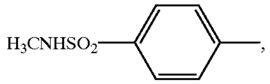

(D2)

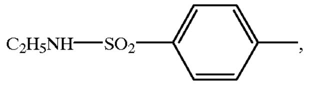

(D2)

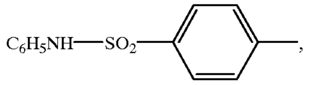

(D1, D2)

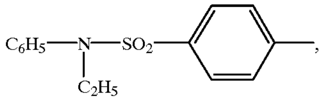

(D1, D2)

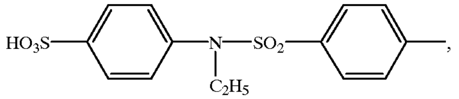

(D1, D2)

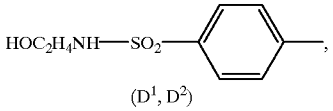

(D1, D2)

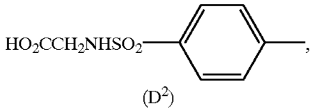

(D2)

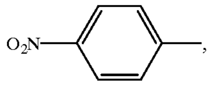

(D2)

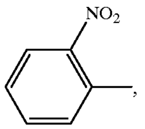

(D2)

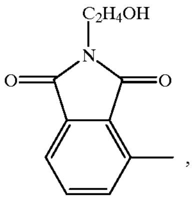

(D1)

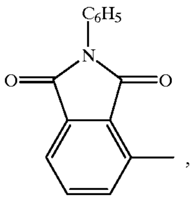

(D1)

-continued

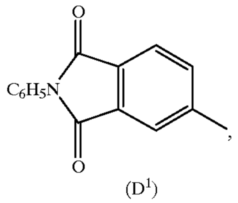

(D1)

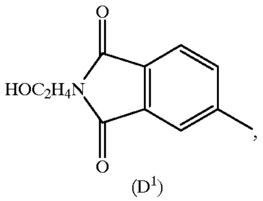

(D1)

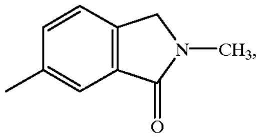

(D1)

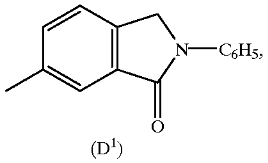

(D1)

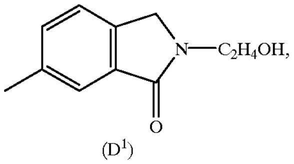

(D1)

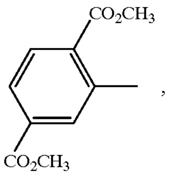

(D1)

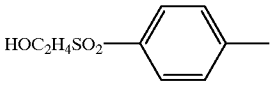

or (D2)

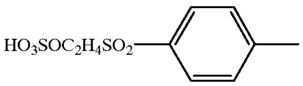

(D2)

Since the disazo dyes of the formula I contain a plurality of hydroxysulfonyl groups and optionally also carboxyl groups, their salts are likewise encompassed by the invention.

Suitable salts are metal or ammonium salts. Metal salts are in particular the lithium, sodium or potassium salts. Ammonium salts for the purposes of the present invention are those salts with either unsubstituted or substituted ammonium cations. Substituted ammonium cations are for example monoalkyl-, dialkyl-, trialkyl-, tetraalkyl- or benzyltrialkyl-ammonium cations or those cations derived from nitrogenous five- or six-membered saturated heterocycles, such as pyrrolidinium, piperidinium, morpholinium or piperazinium cations or their N-monoalkyl- or N,N-dialkyl-substituted products. Alkyl is here in general to be understood as meaning straight-chain or branched $C_1$–$C_{20}$-alkyl which may be substituted by from 1 to 3 hydroxyl groups and/or interrupted by from 1 to 4 oxygen atoms in ether function.

Preference is given to disazo dyes of the formula I containing 3, 4 or 5, in particular 3 or 4, hydroxysulfonyl groups.

Preference is further given to disazo dyes of the formula I containing 1 or 2 carboxyl groups.

Preference is further given to disazo dyes of the formula I containing 2 hydroxysulfonyl groups, 2 hydroxyl groups and optionally 1 carboxyl group.

Preference is further given to disazo dyes of the formula I where Alk is $C_1$–$C_6$-alkyl which may be interrupted by 1 or 2 oxygen atoms in ether function or by 1 sulfonyl group and may be substituted by hydroxyl, $C_1$–$C_4$-alkanoyloxy, sulfato, chlorine, cyano, carboxyl, hydroxysulfonyl, phenyl or hydroxysulfonylphenyl.

Preference is further given to disazo dyes of the formula I where Ar is phenyl which may be substituted by $C_1$–$C_4$-alkyl, $C_1$–$C_4$-alkoxy, carboxyl, $C_1$–$C_4$-alkanoylamino, methoxyacetylamino, hydroxysulfonyl or a radical of the formula $SO_2$—CH═$CH_2$, $SO_2$—$C_2H_4$—Q, $SO_2$—NHAlk, $SO_2$—N$(Alk)_2$, $SO_2$—G, $SO_2$—OG, $SO_2$—NHG or $SO_2$—N(Alk)G.

Preference is further given to disazo dyes of the formula II (II)

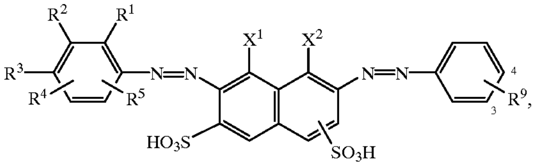

where $R^9$ is a radical of the formula $SO_2$—CH═$CH_2$, $SO_2$—$CH_2$CH═$CH_2$, $SO_2$—$C_2H_4$Q, pyrrolidinylsulfonyl, piperidinylsulfonyl, morpholidinylsulfonyl or a radical of the formula $SO_2$—N$(Alk)_2$, $SO_2$—NHAlk, $SO_2$—N(Ar)Alk or $SO_2$—NHAr, $R^1$, $R^2$, $R^3$, $R^4$, $R^5$, $X^1$ and $X^2$ are each as defined above, and $R^9$ is in the 3- or 4-position.

Particular preference is given to disazo dyes containing a radical of the formula $SO_2$—CH═$CH_2$, $SO_2$—$CH_2$CH═$CH_2$ or $SO_2$—$C_2H_4$—Q, especially those dyes which contain a radical of the formula $SO_2$—$C_2H_4$—$Q^1$, where $Q^1$ is an alkali-detachable group.

Emphasis is given to dyes of the general formula III (III)

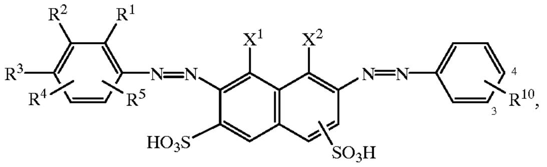

where $R^{10}$ is a radical of the formula $SO_2$—CH═$CH_2$, $SO_2$—$CH_2$CH═$CH_2$ or $SO_2$—$C_2H_4$—Q, $R^1$, $R^2$, $R^3$, $R^4$, $R^5$, $X^1$ and $X^2$ are each as defined above, and $R^{10}$ is in the 3- or preferably 4-position.

Particular preference is further given to disazo dyes of the formula I where $R^6$, $R^7$ or $R^8$ is a radical of the formula $SO_2$—N$(Alk)_2$, $SO_2$—NHAlk, $SO_2$—N(Ar)Alk, $SO_2$—NHAr or pyrrolidinylsulfonyl, piperidinylsulfonyl or morpholinylsulfonyl. Disazo dyes of the formula I where $R^3$ and/or $R^7$ is a radical of the formula $SO_2$—N(Ar)Alk or $SO_2$—NHAr are of particular importance. Emphasis is given to the dyes of the general formulae IV and V (IV)

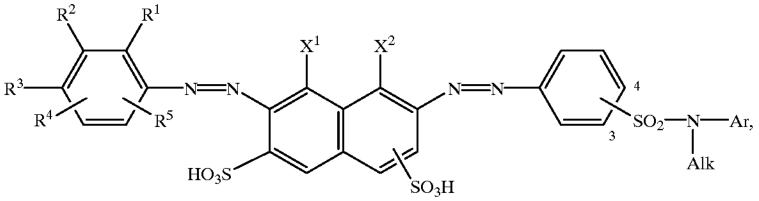

(V)

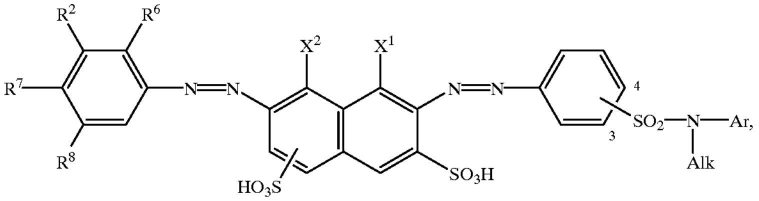

where $R^1$, $R^2$, $R^3$, $R^4$, $R^5$ $R^6$, $R^7$, $R^8$, $X^1$, $X^2$, Alk and Ar are each as defined above and the sulfonamide group is in the 3-position or preferably in the 4-position.

Particular preference is given to dyes of the formula I where $R^3$ and/or $R^7$ are each a radical of the formula $SO_2$—N(Ar)Alk, where Ar contains a radical of the formula $SO_2$—$C_2H_4$—Q, $SO_2$—CH═$CH_2$ or $SO_2$—$CH_2$CH═$CH_2$. Preference is further given to dyes of the formulae IV and V where Ar is a phenyl or naphthyl group which is substituted by a radical of the formula $SO_2—CH_2—CH_2—Q$, $SO_2—CH{=}CH_2$ or $SO_2—CH_2—CH{=}CH_2$. Emphasis is given in particular to dyes of the formula IVa (IVa)

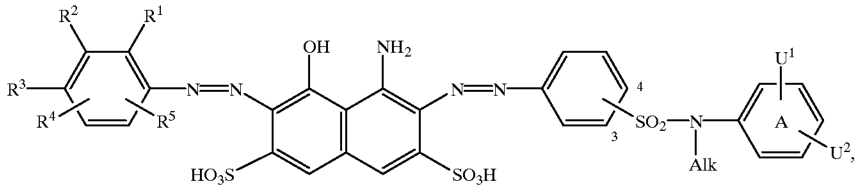

where $R^1$, $R^2$, $R^3$, $R^4$ and $R^5$ are each as defined above, the ring A may be benzofused, Alk is $C_1$–$C_8$-alkyl with or without interruption by from 1 to 3 oxygen atoms in ether function or by 1 sulfur atom or 1 sulfonyl group and with or without substitution by hydroxyl, $C_1$–$C_4$-alkanoyloxy, benzoyloxy, sulfato, halogen, cyano, carbamoyl, carboxyl, hydroxysulfonyl, phenyl or hydroxysulfonylphenyl, or is $C_5$–$C_8$-cycloalkyl, $U^1$ is hydrogen, $C_1$–$C_4$-alkyl, unsubstituted or $C_1$–$C_4$-alkoxy- or phenyl-substituted, or halogen, and $U^2$ is a radical of the formula $SO_2—CH{=}CH_2$ or $SO_2—C_2H_4—Q$, where Q is hydroxyl or an alkali-detachable group, and the sulfonamide radical is in the 3- or 4-position.

Particular preference is further given to dyes of the formula IVb (IVb)

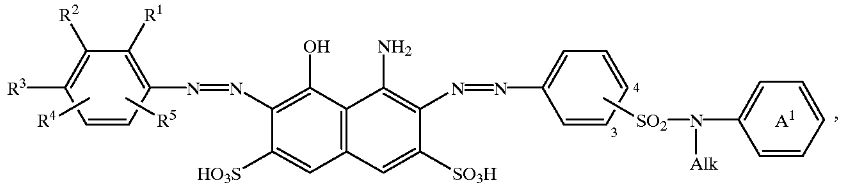

where $R^1$, $R^2$, $R^3$, $R^4$ and $R^5$ are each as defined above, the ring $A^1$ may be benzofused and may be substituted by hydroxysulfonyl, carboxyl, $C_1$–$C_4$-alkyl, chlorine or $C_1$–$C_4$-alkoxy, Alk is $C_1$–$C_8$-alkyl with or without interruption by from 1 to 3 oxygen atoms in ether function or by 1 sulfur atom or 1 sulfonyl group and with or without substitution by hydroxyl, $C_1$–$C_4$-alkanoyloxy, benzoyloxy, sulfato, halogen, cyano, carbamoyl, carboxyl, hydroxysulfonyl, phenyl or hydroxysulfonylphenyl, or is $C_5$–$C_8$-cycloalkyl, and the sulfonamide radical is in the 3- or 4-position. Preference is given especially to dyes of formula IVb where the ring A is mono- or disubstituted by carboxyl or hydroxysulfonyl.

Preference is further given to disazo dyes of the formulae Ia to In (Ia)
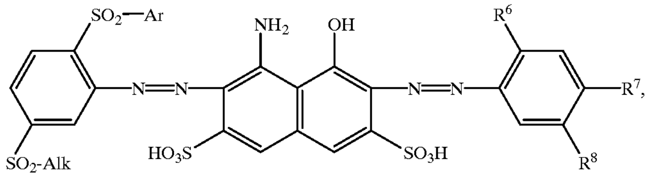
(Ib)
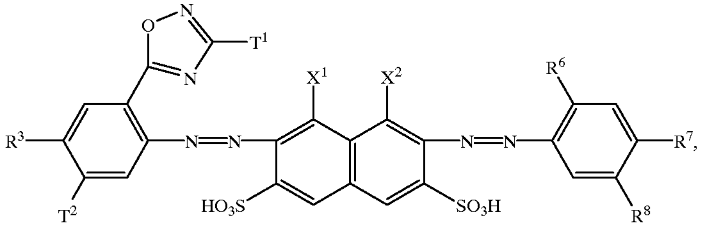
(Ic)
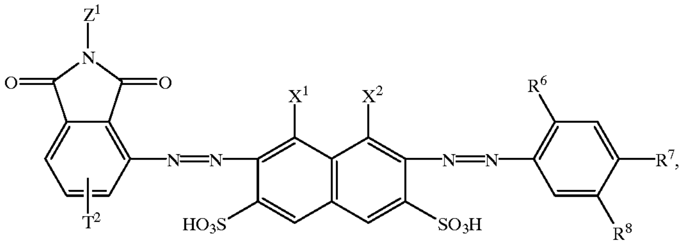
(Id)
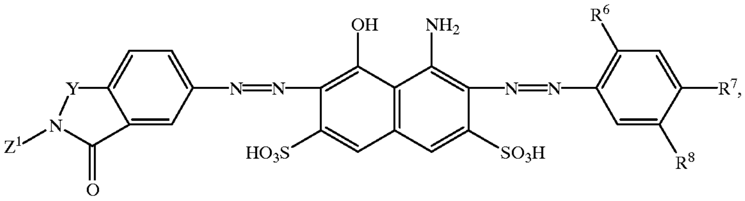
(Ie)
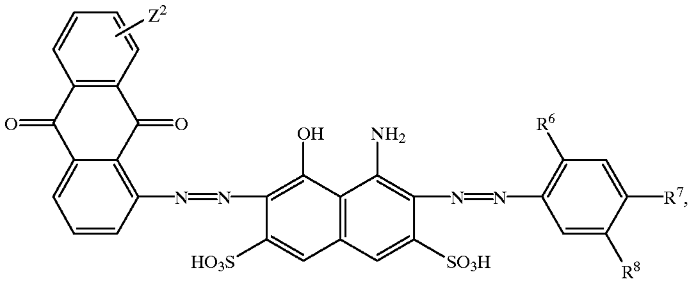
(If)
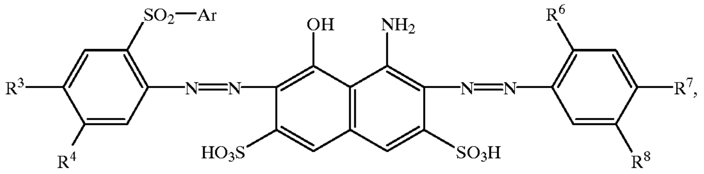
(Ig)
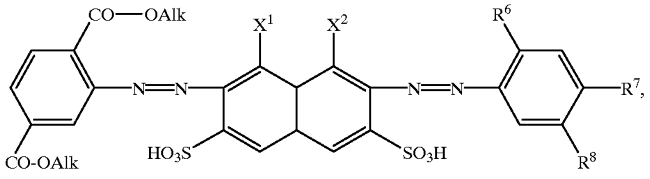

-continued (Ih)

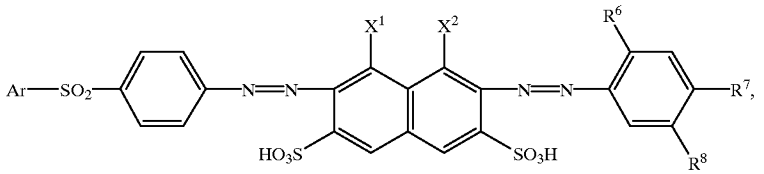

(Ij)

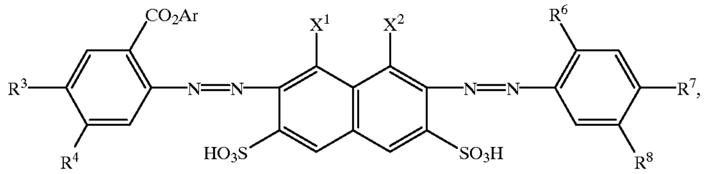

(Ik)

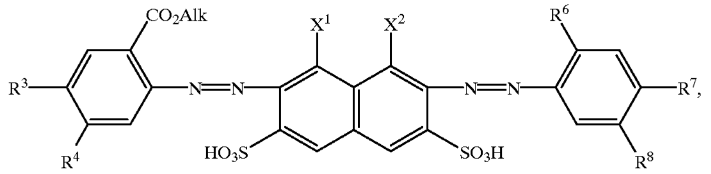

(Im)

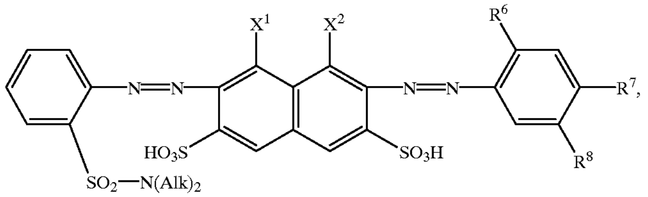

(In)

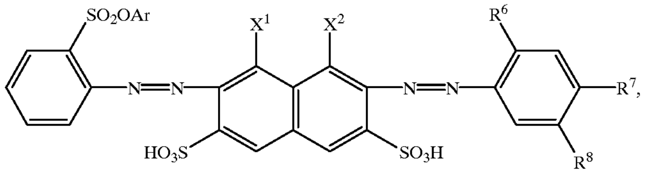

where $T^1$ is Alk or Ar, $T^2$ is hydrogen or hydroxysulfonyl, and $X^1$, $X^2$, $R^3$, $R^4$, $R^6$, $R^7$, $R^8$, Y, $Z^1$, Alk and Ar are each as defined above.

Preference is further given to disazo dyes of the formulae I and also Ia to In where $R^6$ and $R^8$ are each hydrogen and $R^7$ is a radical $R^9$ which is as defined above, and in particular a radical of the formula $SO_2$—N(Ar)Alk, where Ar and Alk are each as defined above.

Preference is further given to disazo dyes of the formulae I and also Ia to In containing a radical of the formula $SO_2$—CH═$CH_2$ or in particular $SO_2$—$C_2H_4$—Q where Q is as given above and denotes in particular sulfato, chlorine or acetyloxy.

Preference is further given to disazo dyes of the formula I where $R^1$, $R^6$, $R^7$ or $R^8$ is an oxadiazole radical and especially of the formulae II, III, IV, IVa and IVb where $R^1$ is an oxadiazole radical.

Particular preference is given to disazo dyes of the formulae Ia, Ib (including in particular those where $X^1$=OH and $X^2$=$NH_2$), If, Ih, Ij, Ik, Im and In.

Of particular importance are mixtures of dyes of the formula Ic where $X^1$ is hydroxyl and $X^2$ is amino and Id where Y is carbonyl. Of these, particularly suitable mixtures are those where $R^6$ and $R^8$ are each hydrogen and $R^7$ is a radical of the formula $SO_2$—N(Ar)Alk where Ar and Alk are each as defined above.

Particular preference is further given to mixtures of dyes Ic and Id where the dyes of the formulae Ic and Id are present in a weight ratio of from 30:70 to 70:30.

In addition, preference is given to disazo dyes of the formula I in which the substituents are selected from a combination of the above-recited preferred substituents.

The novel disazo dyes of the formula I are obtainable in a conventional manner.

For example, they can be obtained by diazotizing an aniline of the formula VI (VI)

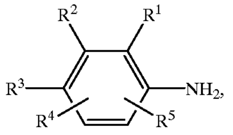

where $R^1$, $R^2$, $R^3$, $R^4$ and $R^5$ are each as defined above, in a conventional manner and coupling the resulting diazonium salt with a naphthalene of the formula VII (VII)

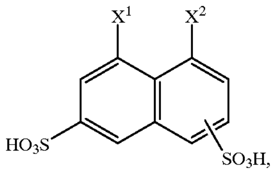

where $X^1$ and $X^2$ are each as defined above.

The resulting monoazo dye of the formula VIII (VIII)

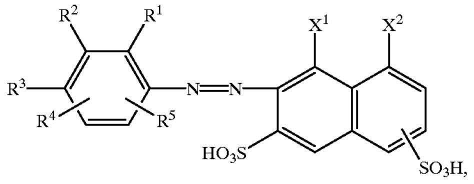

where $R^1$, $R^2$, $R^3$, $R^4$, $R^5$, $X^1$ and $X^2$ are each as defined above, can then be coupled with a diazonium salt derived from an aniline of the formula IX (IX)

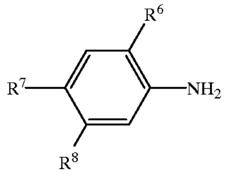

where $R^6$, $R^7$ and $R^8$ are each as defined above.

It will be appreciated that the dyes can also be obtained by the reverse sequence, by diazotizing $D^2$—$NH_2$ and coupling with the naphthalene of the formula VII and then diazotizing $D^1$—$NH_2$ and coupling with the resulting dye.

The dyes of the formula I according to the invention are advantageously useful for dyeing natural or synthetic substrates, in particular wool, leather or polyamide.

The dyeings obtained have black and blue to navy shades and good lightfastness and also good wetfastness properties.

The novel dyes can be applied alone and mixed with one another or else mixed with other dyes.

The present invention further encompasses a process for dyeing wool at a pH of from 3 to 7 by using disazo dyes containing an $SO_2$—$C_2H_4$—$Q^1$ radical. The prior art azo class reactive dyes require special dyeing processes for wool. It has now been found that the novel reactive dyes, especially those of the formula III where $R^{10}$ is a radical of the formula $SO_2$—$C_2H_4$—$Q^1$, lead to excellent dyeing results by conventional wool-dyeing methods under acidic conditions.

The present invention further provides sulfonamides of the formula X (X)

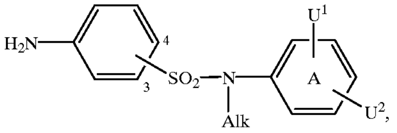

where the ring A may be benzo-fused,

Alk is $C_1$–$C_8$-alkyl which may be interrupted by from 1 to 3 oxygen atoms in ether function or by 1 sulfur atom or 1 sulfonyl group and may be substituted by hydroxyl, $C_1$–$C_4$-alkanoyloxy, benzoyloxy, sulfato, halogen, cyano, carbamoyl, carboxyl, hydroxysulfonyl, phenyl or hydroxysulfonylphenyl, or is $C_5$–$C_8$-cycloalkyl, $U^1$ is hydrogen, $C_1$–$C_4$-alkyl which may be substituted by $C_1$–$C_4$-alkoxy or phenyl, or is halogen, and $U^2$ is a radical of the formula $SO_2$—CH=$CH_2$ or $SO_2$—$C_2H_4$—Q, where Q is hydroxyl or an alkali-detachable group and the sulfonamide is in the 3- or 4-position.

The present invention further provides sulfonamides of the formula XI (XI)

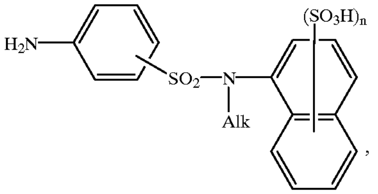

where n is 1 or 2,

Alk is $C_1$–$C_8$-alkyl which may be interrupted by from 1 to 3 oxygen atoms in ether function or by 1 sulfur atom or 1 sulfonyl group and may be substituted by hydroxyl, $C_1$–$C_4$-alkanoyloxy, benzoyloxy, sulfato, halogen, cyano, carbamoyl, carboxyl, hydroxysulfonyl, phenyl or hydroxysulfonylphenyl, or is $C_5$–C8-cycloalkyl and the sulfonamide is in the 3- or 4-position.

As regards exemplification of the substituents Alk, $U^1$ and $U^2$, the observations made above refer.

The novel sulfonamides of the formula X are obtainable in a conventional manner.

For example, they can be obtained by reacting an aniline-sulfonic acid of the formula XII (XII)

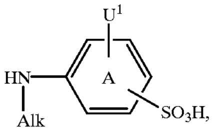

where the ring A, Alk and $U^1$ are each as defined above, with 4-acetylaminobenzenesulfonyl chloride and converting the resulting sulfonamide, for example with thionyl chloride or chlorosulfonic acid, into the corresponding sulfonyl chloride of the formula XIII (XIII)

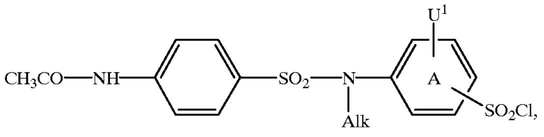

where the ring A, Alk and $U^1$ are each as defined above. Reducing the sulfonyl chloride group gives the sulfinic acid, which, for example by reaction with ethylene oxide, can be made to yield the compound of the formula XIV (XIV)

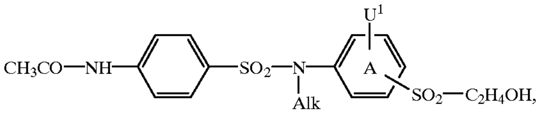

where the ring A, Alk and $U^1$ are each as defined above.

The sulfonamides of the formula X are obtained by customary deacetylation and/or esterification reactions.

The novel sulfonamides of the formula XI are likewise obtainable in a conventional manner.

For example, they can be obtained by reacting a naphthalenesulfonic acid of the formula XV (XV)

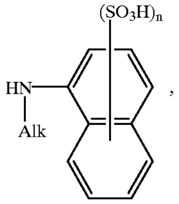

where n and Alk are each as defined above, with 4-acetylaminobenzenesulfonyl chloride and deacetylating the resulting sulfonamide in a conventional manner.

The sulfonamides of the formulae X and XI are useful intermediates for dye synthesis, especially for synthesizing the disazo dyes of the formula I.

The Examples which follow illustrate the invention.

EXAMPLE 1

46.8 g of the red dye of the formula

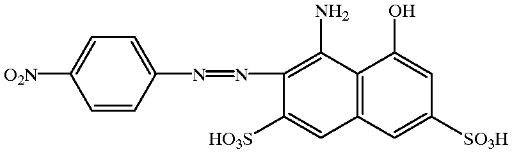

were dissolved in 200 ml of water at pH 7 (sodium hydroxide solution) and at room temperature. To the solution was added, simultaneously with sodium bicarbonate, the suspension of a diazonium salt prepared as follows:

35.8 g of the diazo component of the formula

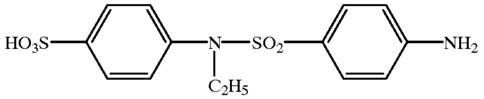

were dissolved in 200 ml of water at pH 11 and then admixed with 31 ml of 23% strength by weight aqueous sodium nitrite solution. The solution was then stirred out onto 100 ml of 18.5% strength by weight hydrochloric acid cooled with ice to 0° C. The mixture was subsequently stirred at from 0 to 5° C. for 1 h, and excess nitrous acid was then destroyed.

The reaction mixture was subsequently stirred at pH 6.5–7 for 2 h. Thereafter the mixture was spray-dried.

This gave 89.5 g of the dye of the formula

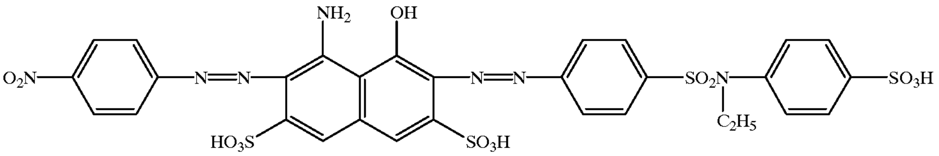

The black powder still comprised about 35 g of sodium chloride and 4 g of water. The dye forms a blue solution in water and dyes wool in a navy shade having excellent lightfastness.

The absorption spectrum in water has a maximum at 600 nm (pH about 4).

EXAMPLE 2 a) 24 g of 2-aminodiphenyl sulfone were stirred overnight with 110 ml of 30% strength by weight hydrochloric acid and 0.1 g of an acidic wetting agent. A little ice was then added to cool down to 0° C., and 31.5 ml of 23% strength by weight aqueous sodium nitrite solution were added dropwise. The diazotization was complete after a further two hours of stirring. Excess nitrous acid was destroyed with sulfamic acid.

The resulting diazonium salt solution was admixed over 90 min of very thorough stirring with 31.9 g of 1-amino-8-hydroxy-naphthalene-3,6-disulfonic acid dissolved in 200 ml of water at pH 5.8. This gave a suspension of the red dye of the formula

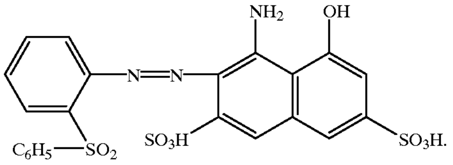

b) 33 g of the diazo component of the formula

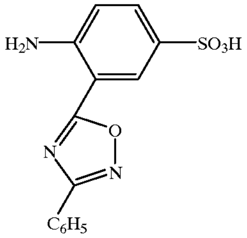

were dissolved in 450 ml of water and 1 g of an alkaline wetting agent at 50° C. and at pH 11 (sodium hydroxide solution). To the solution were added 35 ml of 23% strength by weight aqueous sodium nitrite solution, and the mixture was then poured onto a mixture of 300 ml of water and 40 ml of concentrated hydrochloric acid. The mixture was subsequently stirred at from 40 to 45° C. for 4 h. Excess nitrous acid was then destroyed.

c) The reaction mixtures described in a) and b) were then combined and the pH of the mixture was adjusted to 6–7.5 with dilute sodium hydroxide solution. The mixture was subsequently stirred for 1 h, adjusted to pH 9 and stirred overnight. The resulting blue suspension was heated to 70° C. and the dye of the formula

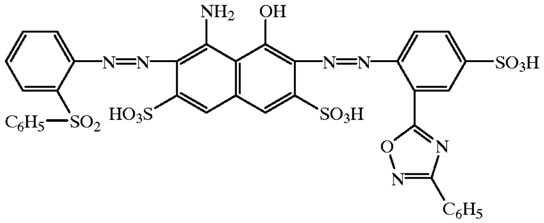

was precipitated with concentrated hydrochloric acid and filtered off with suction. Drying left 88 g of a black powder which dyes wool and polycaprolactam fabric in a navy to black shade ($\lambda_{max}$ in water: 582 nm; shoulder at 626 nm).

EXAMPLE 3 a) 38.0 g of the diazo component of the formula

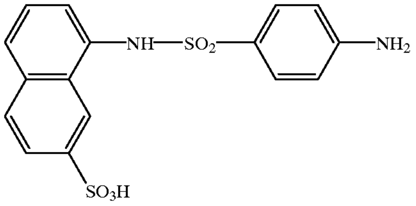

were added to 100 ml of 18.5% strength by weight hydrochloric acid a little at a time and stirred in overnight at room temperature. The mixture was then cooled down to 0° C. with ice and admixed with 31.5 ml of 23% by weight aqueous sodium nitrite solution. Excess nitrous acid was destroyed after stirring for one hour.

b) 31.9 g of 1-amino-8-hydroxynaphthalene-3,6-disulfonic acid were dissolved in 600 ml of water at pH 6 (sodium hydroxide solution). This solution was added with very thorough stirring to the diazonium salt suspension described under a), which had been diluted with 600 ml of water beforehand. The coupling mixture was stirred overnight at from 20 to 25° C. The pH of the mixture was then adjusted to 4 with sodium acetate.

c) 24.5 g of the diazo component of the formula

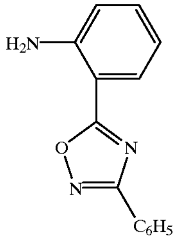

were stirred for 1 h at from 30 to 60° C. with 30.5 g of concentrated hydrochloric acid and 300 ml of water. The mixture was then admixed with 0.7 g of an acidic wetting agent and thereafter 35 ml of 23% strength by weight aqueous sodium nitrite solution were added dropwise over 10 min, and subsequently stirred at 30° C. for 2 h. Excess nitrous acid was then destroyed and the diazonium salt solution was poured into the coupling mixture described under b). The pH of the 2nd coupling reaction was raised to 6–6.5 with sodium bicarbonate and the coupling was completed by stirring overnight.

The dye of the formula

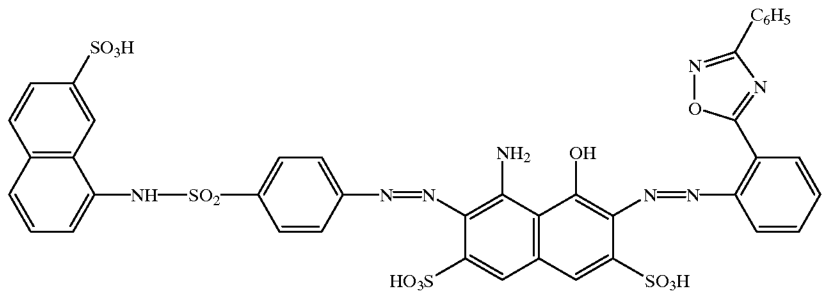

was precipitated with hydrochloric acid. Filtering off with suction and drying left 104.5 g of a black powder which gives a blue solution in water ($\lambda_{max}$: 577 nm) and dyes polycaprolactam and wool in a navy shade having good fastness properties.

EXAMPLE 4

33 g of the diazo component of the formula

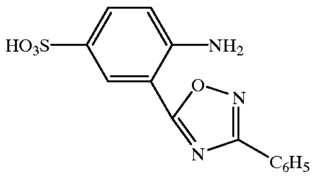

were dissolved in 450 ml of water at 80° C. and pH 11 (sodium hydroxide solution). The solution was admixed with 0.5 g of an acidic wetting agent and 35 ml of 23% strength by weight sodium nitrite solution. The suspension obtained was stirred out onto a mixture of 300 ml of water and 40 ml of concentrated hydrochloric acid. The mixture was subsequently stirred at from 35 to 40° C. for 4 h. Excess nitrous acid was then destroyed and the pH of the suspension was raised to 1.6 with sodium bicarbonate. Thereafter 31.9 g of 1-amino-8-hydroxynaphthalene-3,6-disulfonic acid, dissolved in 150 ml of water at pH 5.8 - 6, were added dropwise over 1.5 h. The temperature was 30–35° C. The reaction mixture was stirred overnight at pH 2 and was then mixed with a diazonium salt solution prepared as follows:

24.5 g of the diazo component of the formula

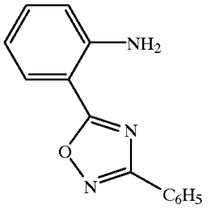

were diazotized similarly to Example 3.

The coupling with the above-described red intermediate of the formula

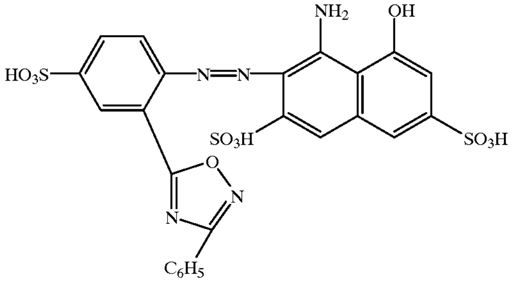

was carried out by gradually raising the pH of the mixture to 7.5 with dilute sodium hydroxide solution, subsequently stirring it at pH 7.5 for 30 min and then adjusting it with sodium hydroxide solution to pH 9.

The dye of the formula

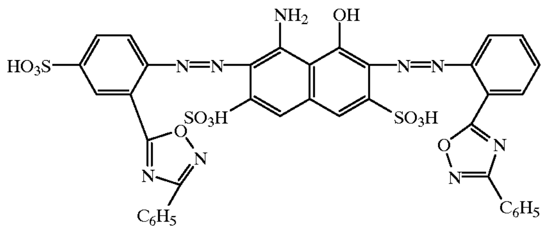

was precipitated by acidifying the reaction mixture to pH 0.5 and additionally adding sodium chloride. Filtering off with suction drying left 144 g of a black powder still comprising about 50 g of salt.

The dye dissolved in water at about pH 4 has a UV-VIS maximum at 575 nm. It dyes wool, polyamide and leather in a fast blue to navy shade.

EXAMPLE 5

61.1 g of the red dye of the formula

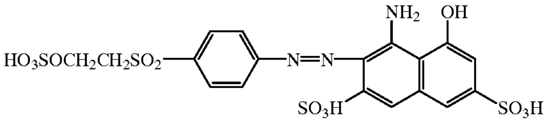

were dissolved at room temperature in 500 ml water at pH 6–7 (sodium bicarbonate). 22.2 g of 4-aminophthalic N-(3-hydroxypropyl)imide were then diazotized by dissolving in 33 ml of concentrated hydrochloric acid and water, cooling with ice to −3° C. and adding 31 ml of 23% strength by weight aqueous sodium nitrite solution. After subsequent stirring at 0–5° C. for 20 min excess nitrous acid was destroyed with sulfamic acid. The resulting diazonium salt solution was added over 30 min to the above-prepared solution in such a way that the pH of the reaction mixture could be held continuously within the range from 6 to 7.8 with sodium bicarbonate. The resulting blue dye solution was spray-dried at pH 6.5. This gave a black powder of the dye of the formula

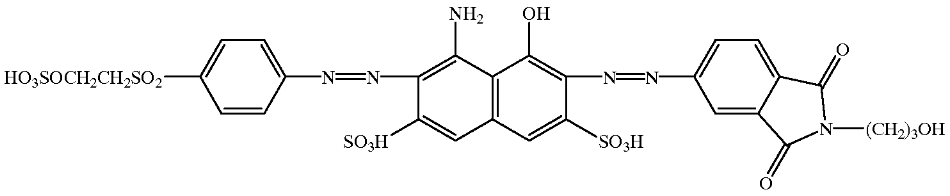

It gives a blue solution in water and dyes wool and polyamide in a bright blue to bluish black shade having excellent wetfastness properties.

The absorption maximum in water at about pH 4 is 590 nm.

EXAMPLE 6

37.5 g of the diazo component of the formula

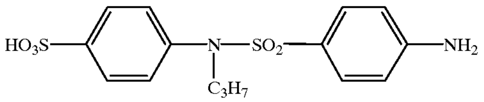

were dissolved in 250 ml of water at pH 10 (sodium hydroxide solution) and thereafter admixed with 31.5 ml of 23% strength by weight aqueous sodium nitrite solution. The mixture was stirred out onto 100 ml of the 18.5% strength by weight hydrochloric acid which had been cooled down to −2° C. with ice in such a way that the temperature was ≦5° C. Initially this produced a solution, from which the diazonium salt separated as a precipitate. After 60 min of stirring at 0–5° C. excess nitrous acid was destroyed. A freshly prepared aqueous solution of 38.5 g of 83.2% by weight 1-amino-8-hydroxynaphthalene-3,6-disulfonic acid was then added dropwise over 1.5 h and the temperature of the reaction mixture was raised to 22° C. Stirring overnight gave a thick suspension of the dye of the formula

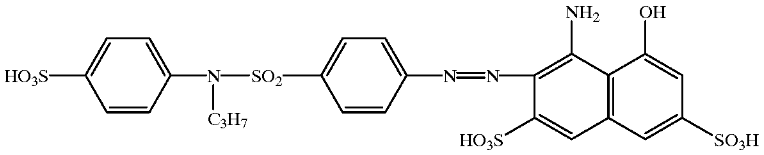

(This dye dissolves on high dilution in water with a red color, the solution having an absorption maximum at 517 nm at pH 3–4 and an absorption maximum at 549 nm at pH 10.)

The mixture was then neutralized with sodium hydroxide solution and admixed with the diazonium salt of 1-aminoanthraquinone, which had been diazotized in a conventional manner in sulfuric acid with nitrosylsulfuric acid and had been isolated in crystalline form following precipitation with ice. At pH 5–8 the diazonium salt was coupled to form the blue dye of the formula

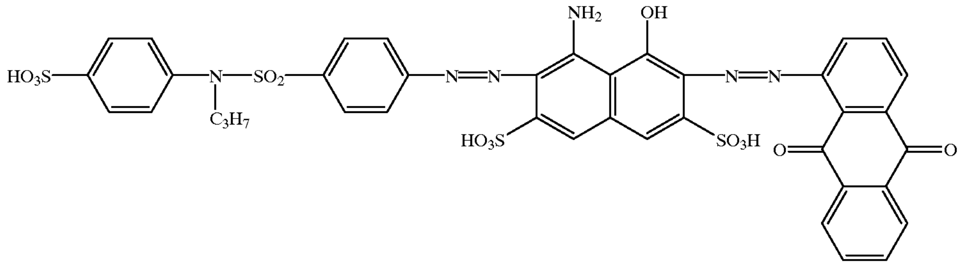

Titrating the reaction mixture, precipitating the dye with potassium chloride, filtering off with suction, washing with aqueous potassium chloride solution and drying left 165 g of a black powder having a dye content of about 61% as potassium salt.

The dye gives a blue solution in water ($\lambda_{max}$: 604 nm and 400 nm at pH ~4) and dyes wool in a strong dark blue shade having excellent fastness properties.

EXAMPLE 7

43.5 g of the diazo component of the formula

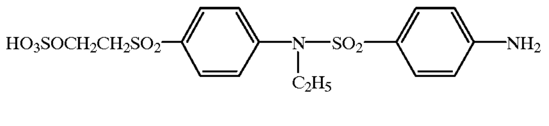

were dissolved in 400 ml of water under weakly acidic conditions (sodium bicarbonate). The mixture was then cooled down to 0° C., and 27 ml of 30% strength by weight hydrochloric acid were added, followed by 31.5 ml of 23% strength of aqueous sodium nitrite solution. The mixture was subsequently stirred at 5° C. for 2 h. Excess nitrous acid was then destroyed and the mixture was stirred out onto a freshly prepared precipitation of 38.5 g of 83.2% strength by weight 1-amino-8-hydroxynaphthalene-3,6-disulfonic acid of pH<1. The reaction mixture was stirred overnight at room temperature. This gave the red dye of the formula

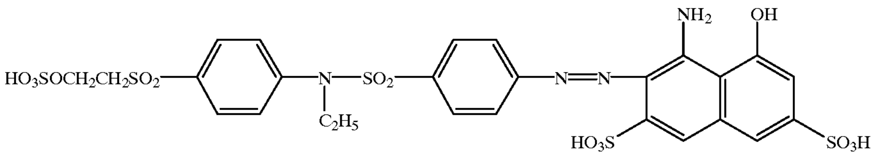

The absorption maximum of an aqueous solution (pH 3–4) has a maximum at 518 nm, and the maximum at pH 7.9 is at 546 nm.

A mixture of 10.3 g of 3-aminophthalic N-($_2$-hydroxyethyl)imide and 10.3 g of 4-aminophthalic N-(2-hydroxyethyl)imide dissolved in 35 ml of concentrated hydrochloric acid and 75 ml of water at 0–5° C. was then diazotized in a conventional manner with sodium nitrite. Following the destruction of excess nitrous acid the diazonium salt solution was added to the above-described red coupling mixture. The mixture was then neutralized by stirring with sodium bicarbonate.

The result obtained was a deep blue solution of the dyes of the formulae

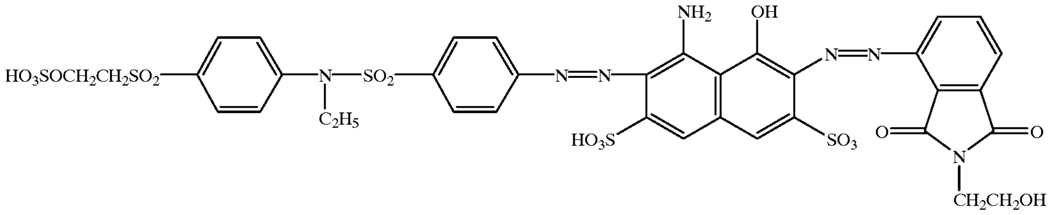
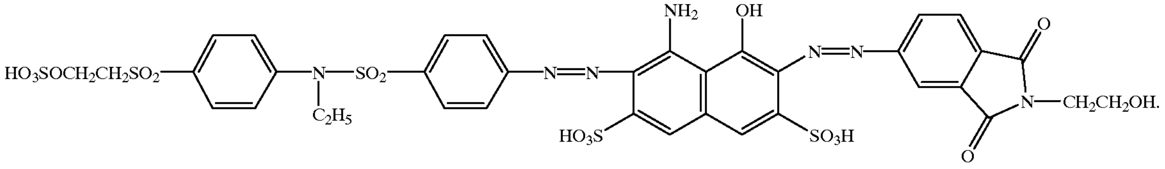
The dye mixture dyes wool in a navy shade having good light- and wetfastness properties.
The dyes listed in the tables below are obtained in a similar manner.
TABLE 1
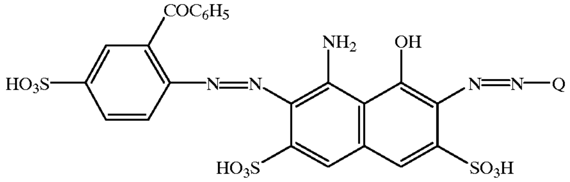
| Ex. No. | Q | Hue on wool |
|---|---|---|
| 8 | 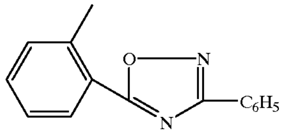 | blue |
| 9 | 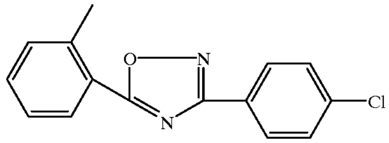 | blue |
| 10 | 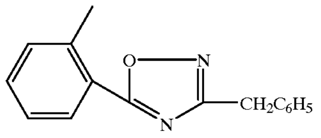 | blue |
| 11 | 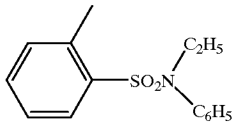 | blue |
TABLE 1-continued
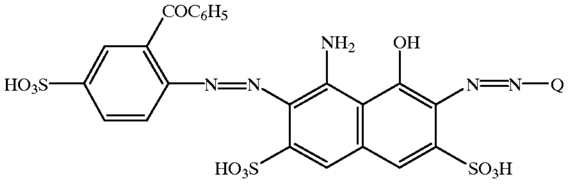
| Ex. No. | Q | Hue on wool |
|---|---|---|
| 12 | 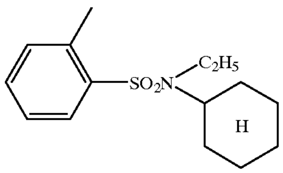 | blue |
| 13 | 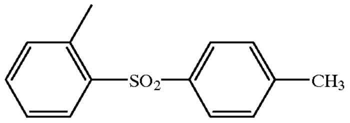 | blue |
| 14 | 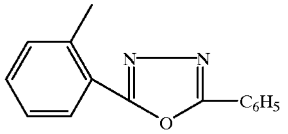 | blue |
| 15 | 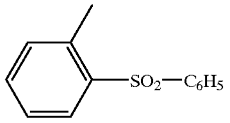 | blue |
| 16 | 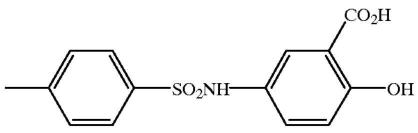 | blue |

TABLE 1-continued
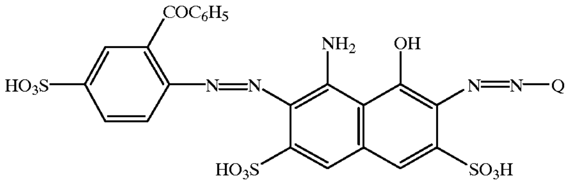
| Ex. No. | Q | Hue on wool |
|---|---|---|
| 17 | 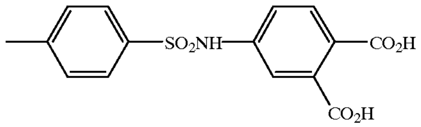 | blue |
| 18 | 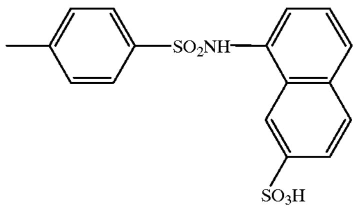 | blue |
TABLE 1-continued
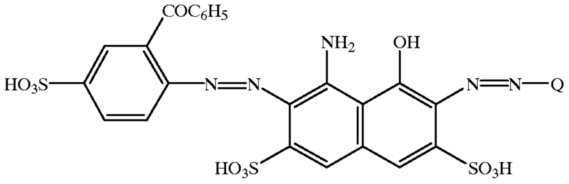
| Ex. No. | Q | Hue on wool |
|---|---|---|
| 19 | 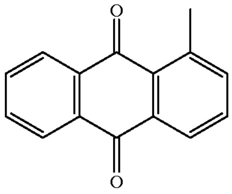 | blue |
TABLE 2
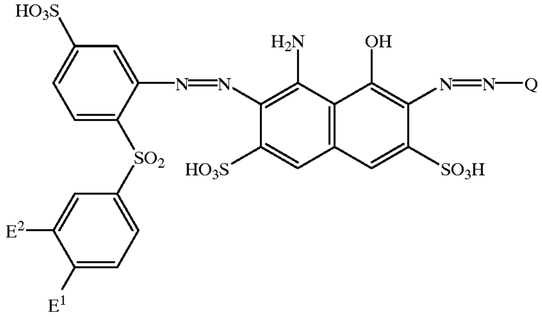
| Ex. No. | Q | $E^1$ | $E^2$ | Hue on wool |
|---|---|---|---|---|
| 20 | 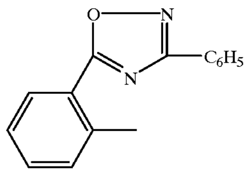 | H | H | bluish black |
| 21 | 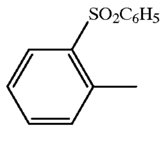 | H | H | bluish black |

TABLE 2-continued
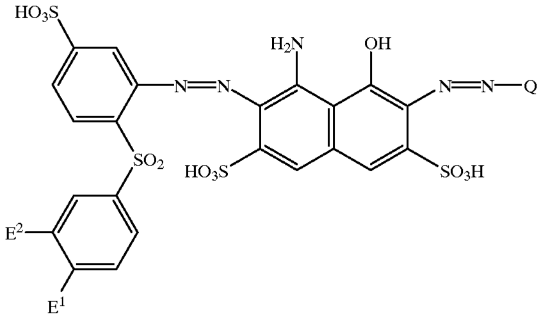
| Ex. No. | Q | $E^1$ | $E^2$ | Hue on wool |
|---|---|---|---|---|
| 22 | 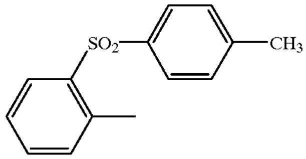 | H | H | bluish black |
| 23 | 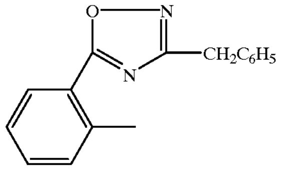 | H | H | bluish black |
| 24 | 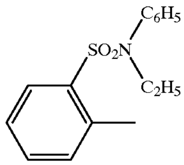 | H | H | bluish black |
| 25 | 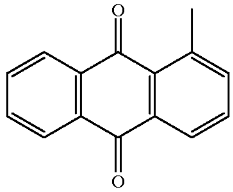 | H | H | bluish black |
| 26 | 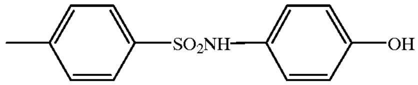 | H | H | bluish black |
| 27 | 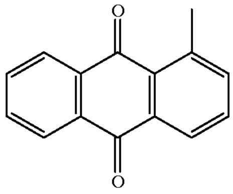 | $NHCOCH_3$ | H | bluish black |

TABLE 2-continued
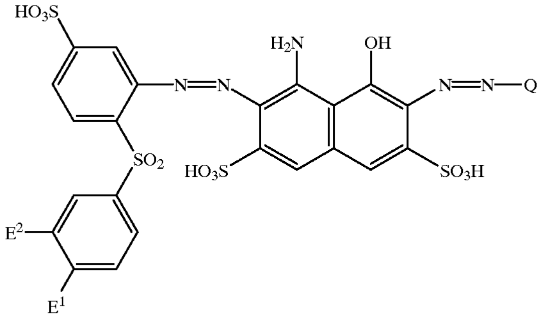
| Ex. No. | Q | $E^1$ | $E^2$ | Hue on wool |
|---|---|---|---|---|
| 28 | 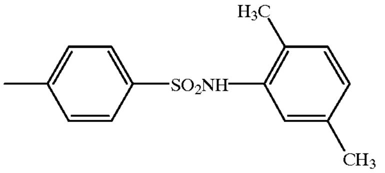 | H | H | bluish black |
| 29 | 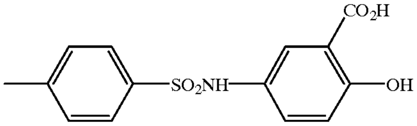 | H | H | bluish black |
| 30 | 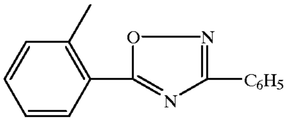 | $CH_3$ | H | bluish black |
| 31 | 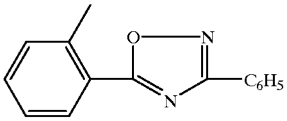 | $CH_3$ | $CH_3$ | bluish black |
TABLE 3
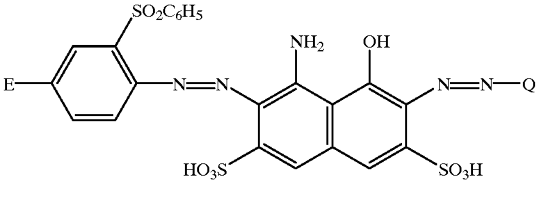
| Ex. No. | Q | E | Hue on wool |
|---|---|---|---|
| 32 | 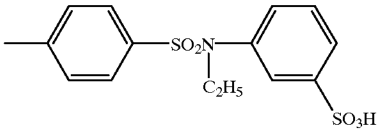 | H | navy |

TABLE 3-continued
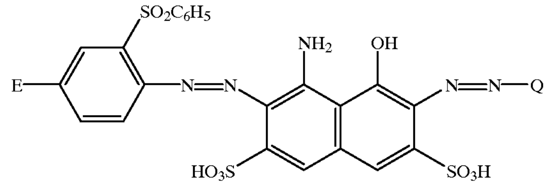
| Ex. No. | Q | E | Hue on wool |
|---|---|---|---|
| 33 | 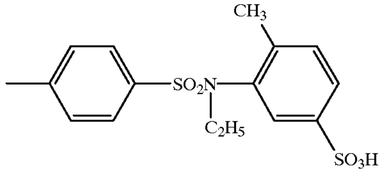 | H | navy |
| 34 | 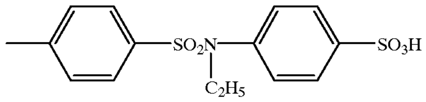 | H | navy |
| 35 | 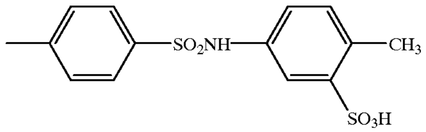 | H | navy |
| 36 | 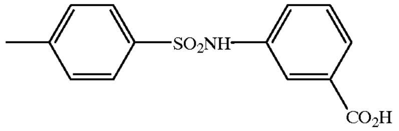 | H | navy |
| 37 | 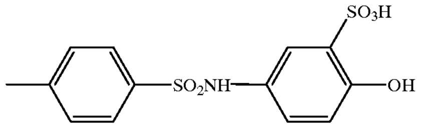 | H | navy |
| 38 | 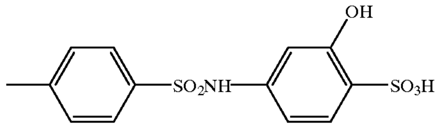 | H | navy |
| 39 | 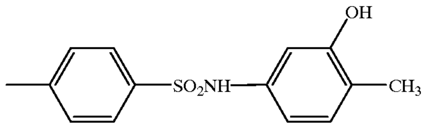 | H | navy |
| 40 | 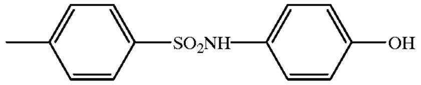 | H | navy |
| 41 | 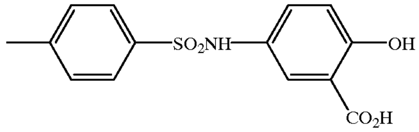 | H | navy |

TABLE 3-continued
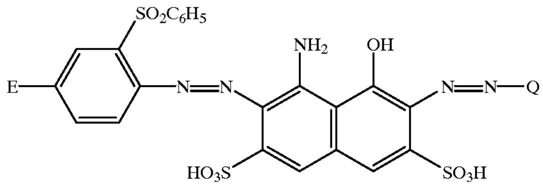
| Ex. No. | Q | E | Hue on wool |
| --- | --- | --- | --- |
| 42 | 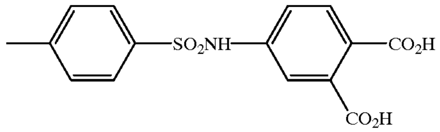 | H | navy |
| 43 | 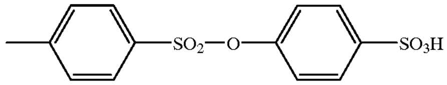 | H | navy |
| 44 | 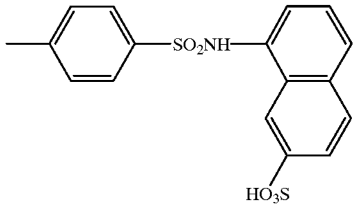 | H | navy |
| 45 | 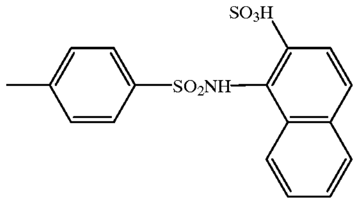 | H | navy |
| 46 | 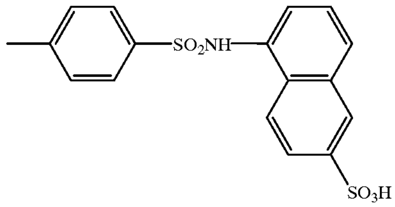 | H | navy |
| 47 | 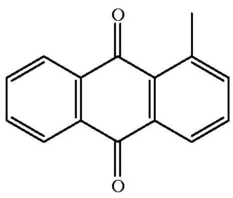 | H | navy |

TABLE 3-continued
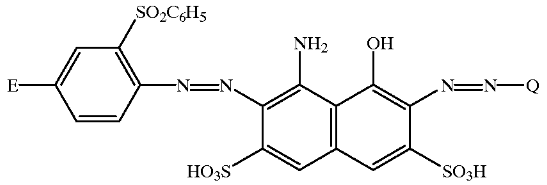
| Ex. No. | Q | E | Hue on wool |
|---|---|---|---|
| 48 | 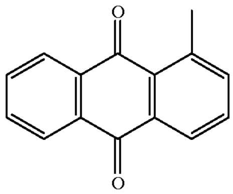 | $CH_3$ | navy |
| 49 | 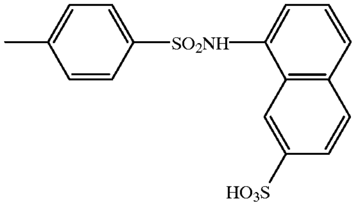 | $CH_3$ | navy |
| 50 | 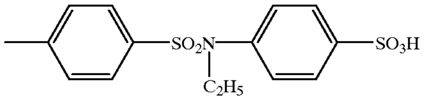 | $CH_3$ | navy |
TABLE 4
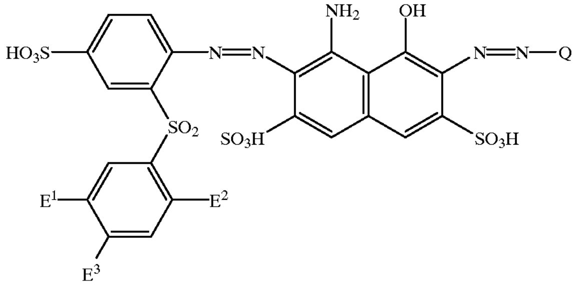
| Ex. No. | $E^1$ | $E^2$ | $E^3$ | Q | Hue on wool |
|---|---|---|---|---|---|
| 51 | H | $CH_3$ | $CH_3$ | 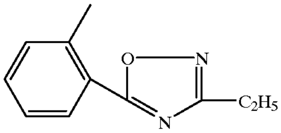 | bluish black |
| 52 | H | H | H | 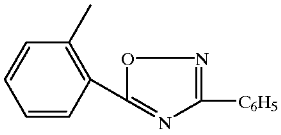 | bluish black |

TABLE 4-continued
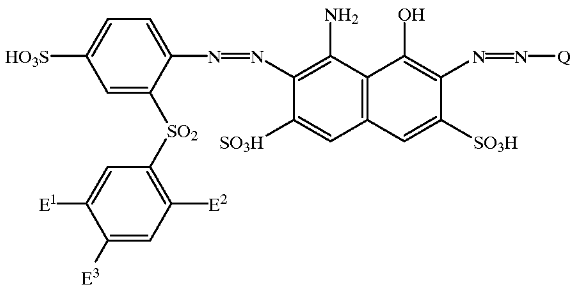
| Ex. No. | E$^1$ | E$^2$ | E$^3$ | Q | Hue on wool |
|---|---|---|---|---|---|
| 53 | H | $CH_3$ | $CH_3$ | 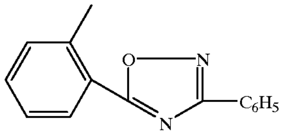 | bluish black |
| 54 | H | H | $CH_3$ | 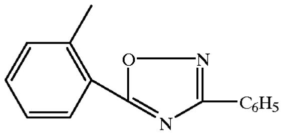 | bluish black |
| 55 | $CH_3$ | $CH_3$ | H | 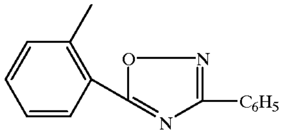 | bluish black |
| 56 | H | H | H | 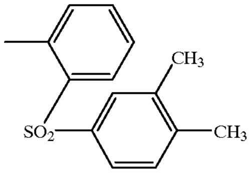 | bluish black |
| 57 | H | H | H | 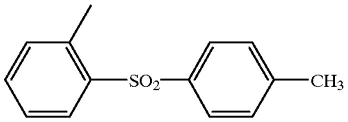 | bluish black |
| 58 | H | H | H | 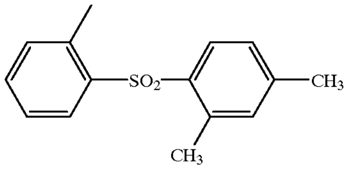 | bluish black |
| 59 | H | H | H | 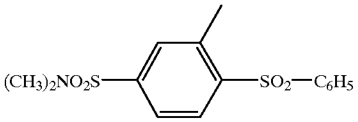 | bluish black |

TABLE 4-continued
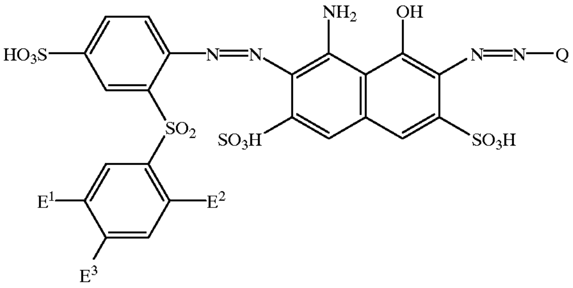
| Ex. No. | $E^1$ | $E^2$ | $E^3$ | Q | Hue on wool |
|---|---|---|---|---|---|
| 60 | H | H | H | 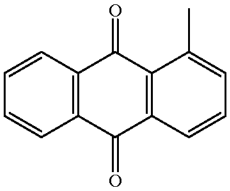 | bluish black |
| 61 | $NHCOCH_3$ | H | $OCH_3$ | 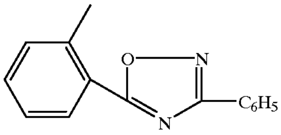 | bluish black |
| 62 | $NHCOCH_3$ | H | $OCH_3$ | 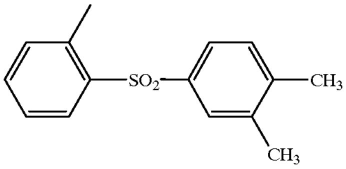 | bluish black |
| 63 | H | H | H | 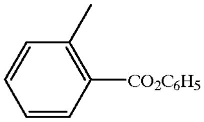 | bluish black |
| 64 | H | H | H | 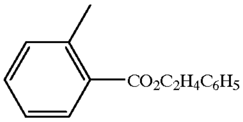 | bluish black |
| 65 | H | H | $CH_3$ | 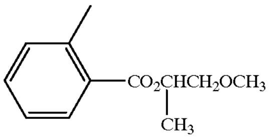 | bluish black |
| 66 | H | H | $CH_3$ | 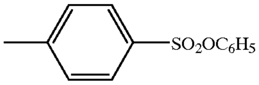 | bluish black |
| 67 | H | H | $CH_3$ | 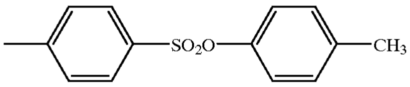 | bluish black |

TABLE 4-continued
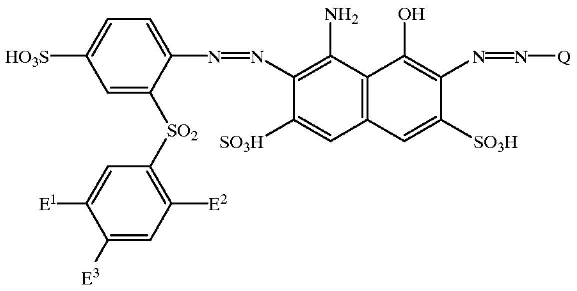
| Ex. No. | $E^1$ | $E^2$ | $E^3$ | Q | Hue on wool |
|---|---|---|---|---|---|
| 68 | H | H | H | 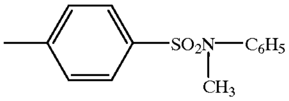 | bluish black |
| 69 | H | H | $CH_3$ | 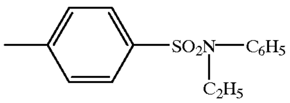 | bluish black |
| 70 | $CH_3$ | H | $CH_3$ | 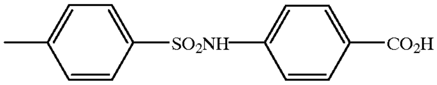 | bluish black |
| 71 | $CO_2H$ | H | H | 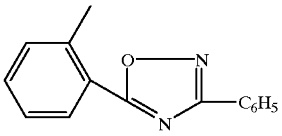 | bluish black |
| 72 | H | $CH_3$ | H | 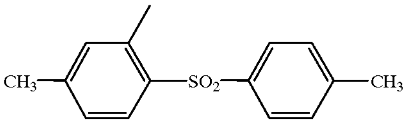 | bluish black |
| 73 | H | $CH_3$ | H | 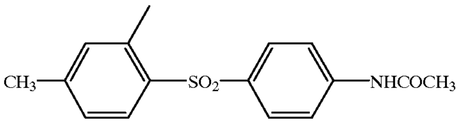 | bluish black |
| 74 | H | H | H | 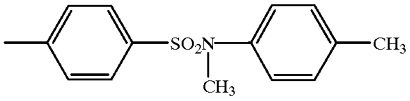 | bluish black |

TABLE 5

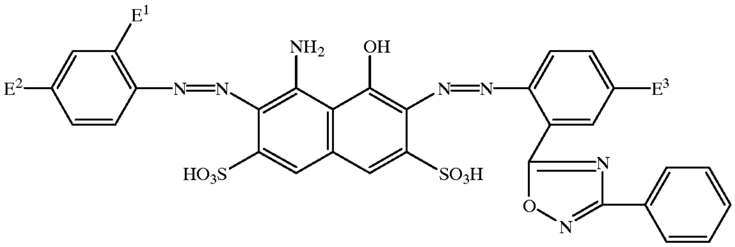

| Ex. No. | $E^1$ | $E^2$ | $E^3$ | Hue on wool |
|---|---|---|---|---|
| 75 | H | 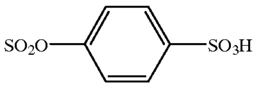 | H | reddish blue |
| 76 | Cl | 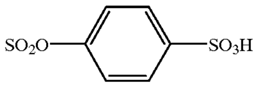 | H | reddish blue |
| 77 | CN | 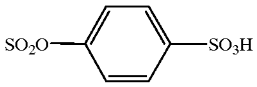 | H | dark blue |
| 78 | $CO_2CH_3$ | $SO_3H$ | H | reddish blue |
| 79 | $CO_2C_2H_5$ | $SO_3H$ | H | reddish blue |
| 80 | CN | $SO_3H$ | H | reddish blue |
| 81 | Br | 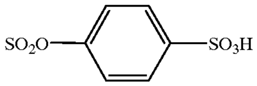 | H | reddish blue |
| 82 | H | $SO_2CH_2CH_2OCOCH_3$ | $SO_3H$ | reddish blue |
| 83 | H | $SO_2CH_2CH_2OH$ | $SO_3H$ | reddish blue |
| 84 | H | $SO_2CH_2CH_2OCHO$ | $SO_3H$ | reddish blue |
| 85 | H | $SO_2CH{=}CH_2$ | $SO_3H$ | reddish blue |
| 86 | H | $SO_2CH_2CH_2Cl$ | $SO_3H$ | reddish blue |
| 87 | H | $SO_2CH_2CH{=}CH_2$ | $SO_3H$ | reddish blue |
| 88 | H | $SO_2C_2H_5$ | $SO_3H$ | reddish blue |
| 89 | H | $SO_2C_6H_5$ | $SO_3H$ | reddish blue |
| 90 | $SO_3H$ | $SO_2C_6H_5$ | H | reddish blue |
| 91 | $SO_3H$ | $SO_2N(C_2H_5)_2$ | H | reddish blue |
| 92 | $SO_3H$ | 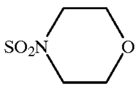 | H | reddish blue |
| 93 | $COC_6H_5$ | Cl | $SO_3H$ | reddish blue |

TABLE 6

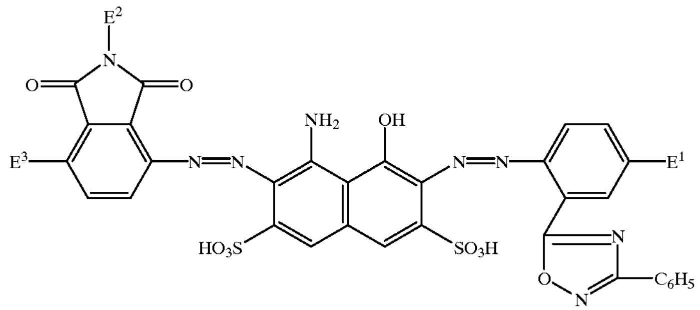

| Ex. No. | $E^1$ | $E^2$ | $E^3$ | Hue on wool |
|---|---|---|---|---|
| 94 | $SO_3H$ | $CH_2CH_2OH$ | H | blue |
| 95 | $SO_3H$ | $CH_2CH_2OCH_3$ | H | blue |
| 96 | $SO_3H$ | $CH_2CH_2CH_2OCH_3$ | H | blue |
| 97 | $SO_3H$ | $CH_3$ | H | blue |
| 98 | $SO_3H$ | $C_2H_5$ | H | blue |
| 99 | H | 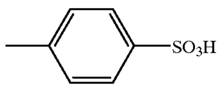 | H | blue |
| 100 | H | 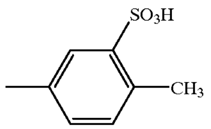 | H | blue |
| 101 | $SO_3H$ | $C_4H_8OH(n)$ | H | blue |
| 102 | $SO_3H$ | $CH_2CH_2CH_2OCH_2CH_2OCH_3$ | H | blue |
| 103 | H | 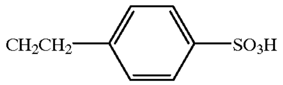 | H | blue |
| 104 | H | $CH_2CH_2OCH_2CH_2OH$ | H | blue |
| 105 | H | $CH_2CH_2SO_2CH_2CH_2OSO_3H$ | H | blue |
| 106 | H | $CH_2CH_2SO_2CH_2CH_2OCOCH_3$ | H | blue |
| 107 | $SO_3H$ | $CH_2CH_2SO_2CH_2CH_2OSO_3H$ | H | blue |
| 108 | $SO_3H$ | $C_2H_5$ | Cl | blue |
| 109 | $SO_3H$ | $C_2H_4OH$ | Cl | blue |
| 110 | H | $CH_2CO_2H$ | H | blue |
| 111 | H | 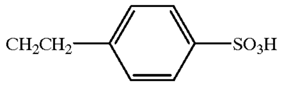 | H | blue |

TABLE 7
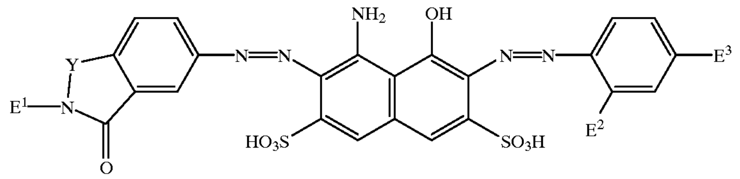
| Ex. No. | $E^3$ | Y | $E^1$ | $E^2$ | Hue on wool |
|---|---|---|---|---|---|
| 112 | $SO_3H$ | $CH_2$ | $CH_2CH_2OCH_3$ | 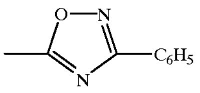 | reddish blue |
| 113 | $SO_3H$ | CO | $CH_2CH_2OCH_3$ | 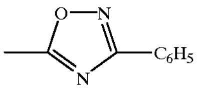 | reddish blue |
| 114 | H | CO | 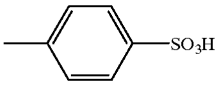 | 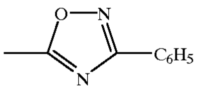 | reddish blue |
| 115 | H | CO | 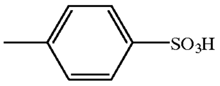 | 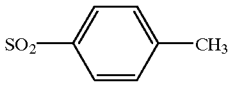 | reddish blue |
| 116 | $SO_3H$ | $CH_2$ | $CH_2CH_2CH_2OCH_3$ | 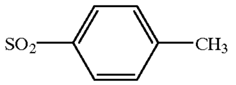 | reddish blue |
| 117 | $SO_3H$ | $CH_2$ | $C_2H_5$ | 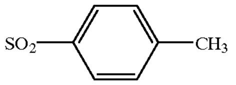 | dark blue |
| 118 | $SO_3H$ | CO | $CH_2CH_2OC_4H_9(n)$ | 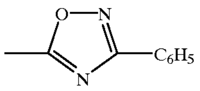 | reddish blue |
| 119 | $SO_3H$ | CO | $CH_2CH_2C_6H_5$ | 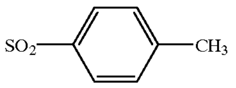 | dark blue |
| 120 | $SO_3H$ | CO | $CH_2C_6H_5$ | 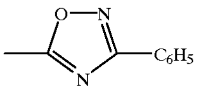 | reddish blue |
| 121 | $SO_3H$ | CO | $CH_2C_6H_5$ | 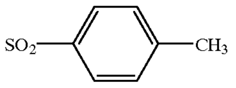 | dark blue |
| 122 | $SO_3H$ | $CH_2$ | $C_4H_9$ | 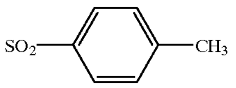 | dark blue |
| 123 | $CH_3$ | CO | 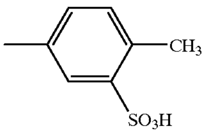 | 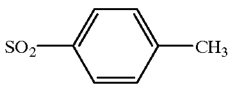 | dark blue |

TABLE 7-continued

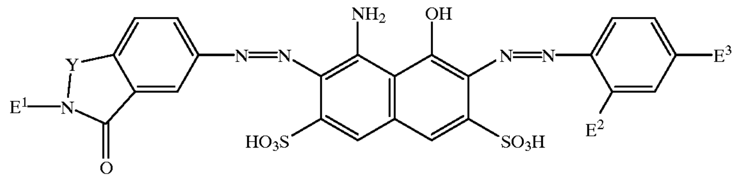

| Ex. No. | $E^3$ | Y | $E^1$ | $E^2$ | Hue on wool |
|---|---|---|---|---|---|
| 124 | $CH_3$ | CO | 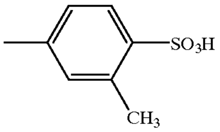 | 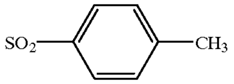 | dark blue |
| 125 | H | $CH_2$ | $CH_2CH_2OH$ | 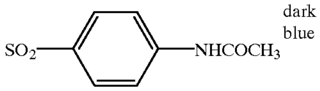 | dark blue |
| 126 | H | CO | $CH_2CH_2OCH_2CH_2OH$ | 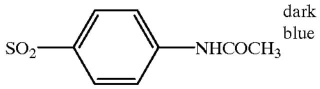 | dark blue |
| 127 | H | $CH_2$ | 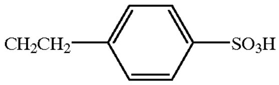 | 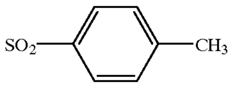 | blue |

TABLE 8

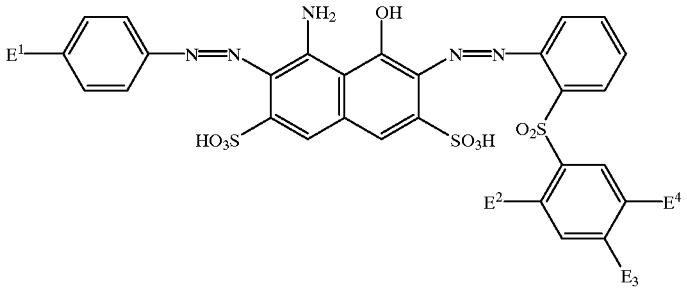

| Ex. No. | $E^1$ | $E^2$ | $E^3$ | $E^4$ | Hue on wool |
|---|---|---|---|---|---|
| 128 | $NO_2$ | H | $CH_3$ | H | grayish blue |
| 129 | $NO_2$ | H | $CH_3$ | $CH_3$ | grayish blue |
| 130 | $NO_2$ | $CH_3$ | $CH_3$ | H | grayish blue |
| 131 | $NO_2$ | $CH_3$ | $OCH_3$ | H | grayish blue |
| 132 | $NO_2$ | H | $OCH_3$ | H | grayish blue |
| 133 | $NO_2$ | H | $OC_2H_5$ | H | grayish blue |
| 134 | $NO_2$ | H | $OC_4H_9$ | H | grayish blue |
| 135 | $NO_2$ | $CH_3$ | H | $CH_3$ | grayish blue |
| 136 | $NO_2$ | H | $C_2H_5$ | H | grayish blue |
| 137 | $NO_2$ | H | $OCH_3$ | $NHCOCH_3$ | grayish blue |
| 138 | $SO_2O—C_6H_5$ | H | $OCH_3$ | H | grayish blue |
| 139 | $SO_2C_2H_4OH$ | H | $CH_3$ | $CH_3$ | grayish blue |
| 140 | $SO_2CH_2CH{=}CH_2$ | H | $OCH_3$ | H | grayish blue |
| 141 | $SO_2CH{=}CH_2$ | H | $CH_3$ | $CH_3$ | grayish blue |
| 142 | $SO_2CH_2CH_2OCOCH_3$ | H | $CH_3$ | $CH_3$ | grayish blue |
| 143 | $SO_2N(CH_3)_2$ | H | $OCH_3$ | H | grayish blue |
| 144 | $SO_2CH{=}CH_2$ | H | $NHCOCH_3$ | H | grayish blue |
| 145 | $SO_2CH_2CH_2OH$ | H | $NHCOCH_3$ | H | grayish blue |

TABLE 9
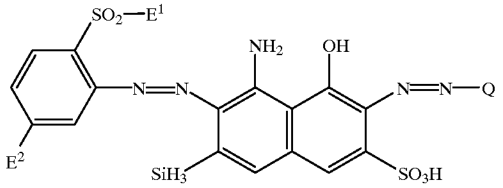
| Ex. No. | $E^1$ | $E^2$ | Q | Hue on wool |
|---|---|---|---|---|
| 146 | $CH_2CH_2OSO_3H$ | H | 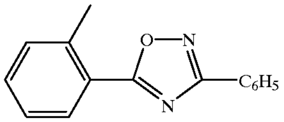 | reddish blue |
| 147 | $CH_2CH_2OCOCH_3$ | H | 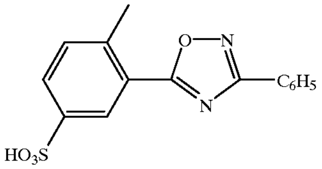 | reddish blue |
| 148 | $C_2H_5$ | H | 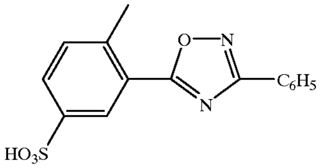 | reddish blue |
| 149 | $CH_2CH_2OCHO$ | $SO_2N(CH_3)_2$ | 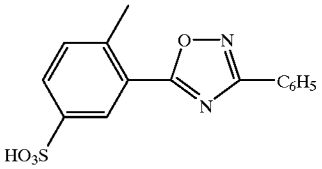 | reddish blue |
| 150 | $CH_2CH_2OCOCH_3$ | $SO_2N(CH_3)_2$ | 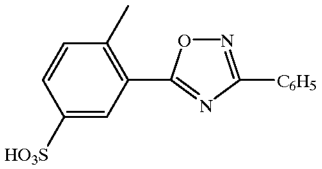 | reddish blue |
| 151 | $CH_3$ | $SO_2NHCH_2CH_2OH$ | 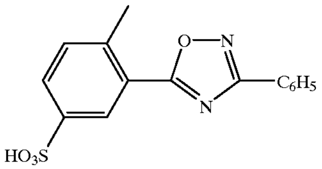 | reddish blue |
| 152 | $CH_2CH_2OH$ | H | 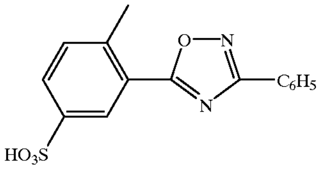 | reddish blue |

TABLE 9-continued
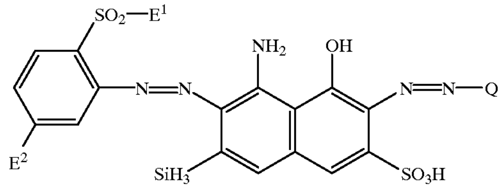
| Ex. No. | $E^1$ | $E^2$ | Q | Hue on wool |
|---|---|---|---|---|
| 153 | $CH_2CH_2OH$ | H | 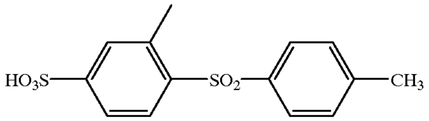 | reddish blue |
| 154 | $CH_2CH_2OH$ | H | 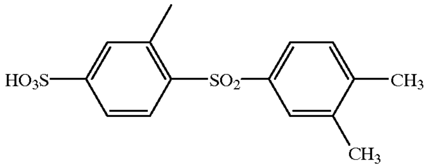 | reddish blue |
| 155 | $CH_2CH_2OH$ | $SO_2N(CH_3)_2$ | 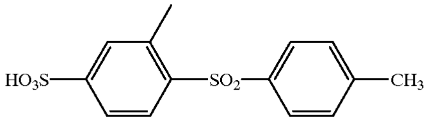 | reddish blue |
| 156 | $CH_2CH_2OH$ | $SO_2N(CH_3)_2$ | 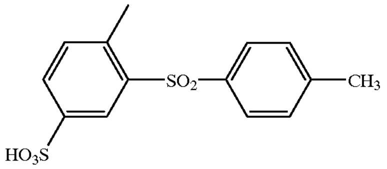 | reddish blue |
| 157 | $CH_3$ | $SO_2N(C_2H_5)_2$ | 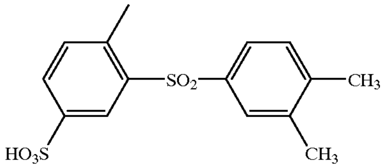 | reddish blue |
| 158 | $C_2H_5$ | H | 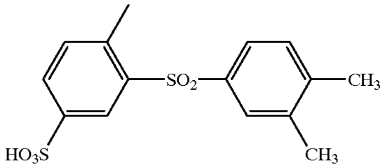 | reddish blue |
| 159 | $C_2H_5$ | $SO_2N(CH_3)_2$ | 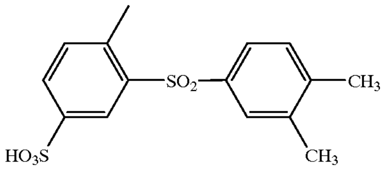 | reddish blue |

TABLE 9-continued
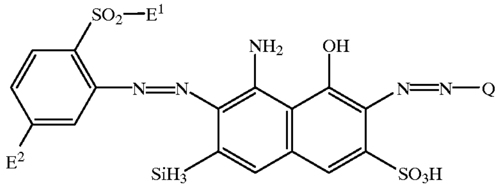
| Ex. No. | $E^1$ | $E^2$ | Q | Hue on wool |
|---|---|---|---|---|
| 160 | $CH_2CH_2OSO_3H$ | H | 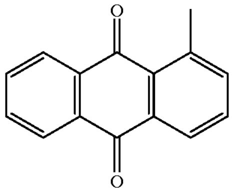 | reddish blue |
| 161 | $CH_3$ | $SO_3H$ | 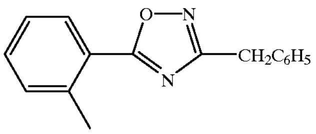 | reddish blue |
| 162 | $C_2H_5$ | $SO_3H$ | 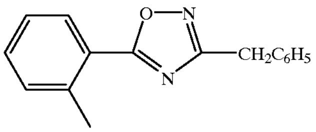 | reddish blue |
| 163 | $C_2H_5$ | $SO_3H$ | 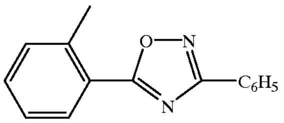 | reddish blue |
| 164 | OH | 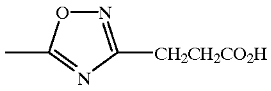 | 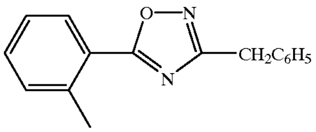 | reddish blue |
TABLE 10
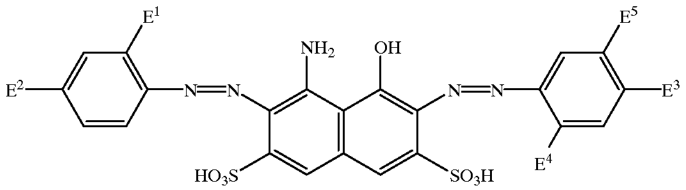
| Ex. No. | $E^1$ | $E^2$ | $E^3$ | $E^4$ | $E^5$ | Hue on wool |
|---|---|---|---|---|---|---|
| 165 | $CO_2CH_3$ | $SO_2OC_6H_5$ | H | 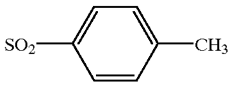 | $SO_3H$ | bluish black |

TABLE 10-continued

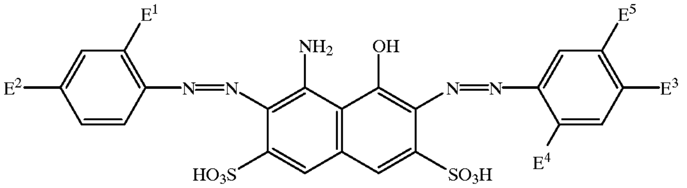

| Ex. No. | $E^1$ | $E^2$ | $E^3$ | $E^4$ | $E^5$ | Hue on wool |
|---|---|---|---|---|---|---|
| 166 | $CO_2CH_3$ | $SO_3H$ | H | 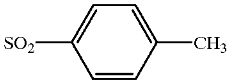 | H | bluish black |
| 167 | $CO_2CH_3$ | $SO_3H$ | H | 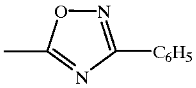 | H | reddish blue |
| 168 | $CO_2CH_3$ | $SO_3H$ | H | 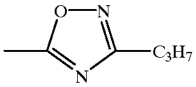 | H | reddish blue |
| 169 | $CO_2CH_3$ | 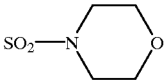 | $SO_3H$ | 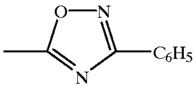 | H | reddish blue |
| 170 | $CO_2CH_3$ | $SO_2N(CH_3)_2$ | $SO_3H$ | 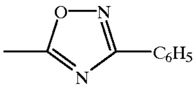 | H | reddish blue |
| 171 | $CO_2CH_3$ | $SO_2N(C_2H_5)_2$ | H | 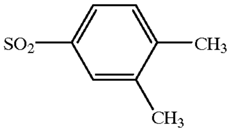 | $SO_3H$ | bluish black |
| 172 | CN | $SO_2N(CH_3)_2$ | $SO_3H$ | 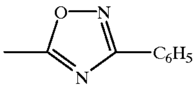 | H | reddish blue |
| 173 | Br | $SO_2N(CH_3)_2$ | $SO_3H$ | 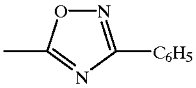 | H | reddish blue |
| 174 | 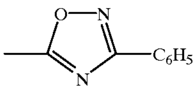 | $SO_2N(C_2H_4OH)_2$ | $SO_3H$ | 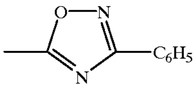 | H | reddish blue |
| 175 | 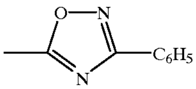 | 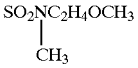 | $SO_3H$ | 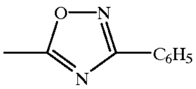 | H | reddish blue |
| 176 | 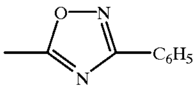 | 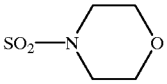 | $SO_3H$ | 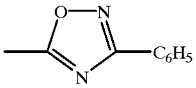 | H | reddish blue |

TABLE 10-continued

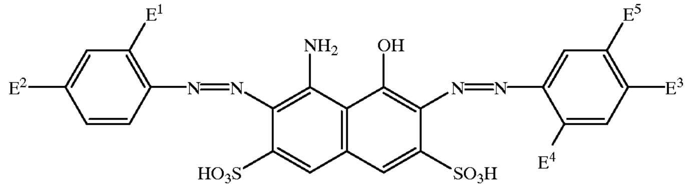

| Ex. No. | $E^1$ | $E^2$ | $E^3$ | $E^4$ | $E^5$ | Hue on wool |
|---|---|---|---|---|---|---|
| 177 | $CO_2CH_3$ | $SO_3H$ | $CH_3$ | 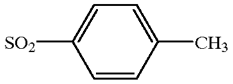 | H | bluish black |
| 178 | $CO_2CH_3$ | $SO_3H$ | H | 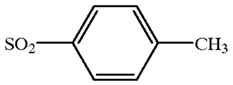 | $CH_3$ | bluish black |
| 179 | H | 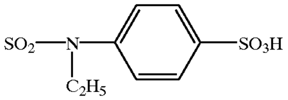 | H | 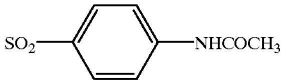 | $SO_3H$ | dark blue |

TABLE 11

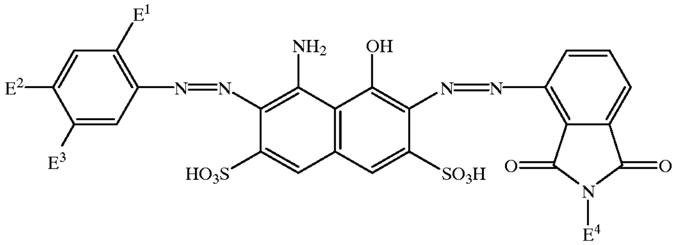

| Ex. No. | $E^1$ | $E^2$ | $E^3$ | $E^4$ | Hue on wool |
|---|---|---|---|---|---|
| 180 | H | $NO_2$ | H | $CH_2CH_2OH$ | reddish blue |
| 181 | H | $NO_2$ | H | $CH_2CH_2CH_2OH$ | reddish blue |
| 182 | H | $NO_2$ | H | $CH_2C_6H_5$ | reddish blue |
| 183 | H | $NO_2$ | H | $(CH_2)_2OCH_3$ | reddish blue |
| 184 | H | $NO_2$ | H | $(CH_2)_3OCH_3$ | reddish blue |
| 185 | H | $NO_2$ | H | $(CH_2)_3O(CH_2)_2OCH_3$ | reddish blue |
| 186 | H | $NO_2$ | H | 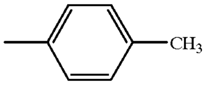 | reddish blue |
| 187 | H | $NO_2$ | H | 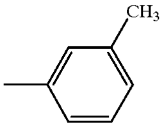 | reddish blue |
| 188 | H | $NO_2$ | H | 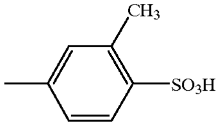 | reddish blue |

TABLE 11-continued

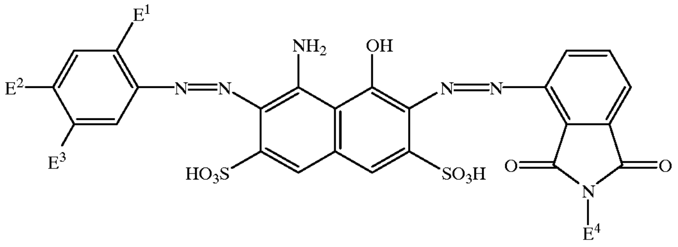

| Ex. No. | $E^1$ | $E^2$ | $E^3$ | $E^4$ | |
|---|---|---|---|---|---|
| 189 | $SO_2C_6H_5$ | H | H | 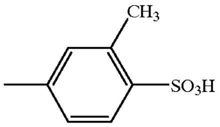 | reddish blue |
| 190 | 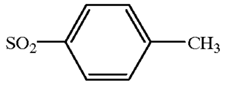 | H | H | 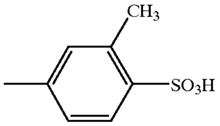 | reddish blue |
| 191 | $SO_2C_6H_5$ | $CH_3$ | H | 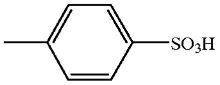 | reddish blue |
| 192 | 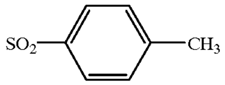 | $SO_3H$ | H | $C_4H_9$ | reddish blue |
| 193 | $SO_2C_6H_5$ | H | $SO_3H$ | $C_4H_9$ | reddish blue |
| 194 | 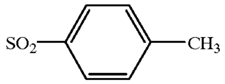 | H | $SO_3H$ | $C_4H_9$ | reddish blue |
| 195 | $SO_2C_6H_5$ | H | $SO_2CH_2CO_2H$ | $C_2H_4OH$ | reddish blue |
| 196 | $SO_2C_6H_5$ | H | $SO_2CH_2CO_2H$ | $CH_2C_6H_5$ | reddish blue |
| 197 | $SO_2C_6H_5$ | H | $SO_2CH_3$ | $CH_2C_6H_5$ | reddish blue |
| 198 | 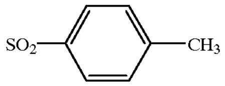 | H | $SO_2CH_2CO_2H$ | $CH_2C_6H_5$ | reddish blue |
| 199 | H | $SO_2—O—C_6H_5$ | H | 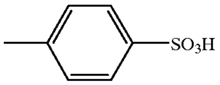 | reddish blue |
| 200 | H | $SO_2—O—C_6H_5$ | H | 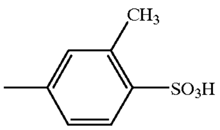 | reddish blue |
| 201 | H | 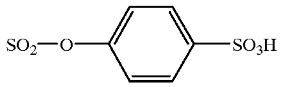 | H | $C_2H_4OH$ | reddish blue |

TABLE 11-continued

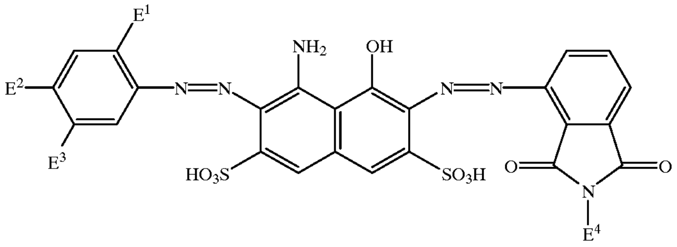

| Ex. No. | $E^1$ | $E^2$ | $E^3$ | $E^4$ | |
|---|---|---|---|---|---|
| 202 | H | 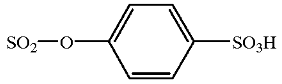 | H | $C_4H_9$ | reddish blue |
| 203 | H | 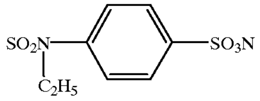 | H | $CH_2CH_2C_6H_5$ | reddish blue |
| 204 | H | 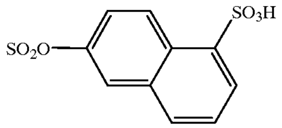 | H | $C_4H_9$ | reddish blue |
| 205 | H | $SO_2N(C_2H_4OH)_2$ | H | $CH_2C_6H_5$ | reddish blue |
| 206 | H | $SO_2N(C_2H_4OCH_3)_2$ | H | $CH_2C_6H_5$ | reddish blue |
| 207 | H | $SO_2N(C_2H_4OCH_3)_2$ | H | $CH_2C_6H_5$ | reddish blue |
| 208 | $SO_3H$ | $SO_2N(C_2H_5)_2$ | H | $CH_2CH_2C_6H_5$ | reddish blue |
| 209 | $SO_3H$ | $SO_2N(C_2H_5)$ 2 | H | $CH_2C_6H_5$ | reddish blue |
| 210 | $SO_3H$ | 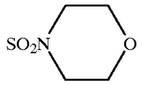 | H | $CH_2C_6H_5$ | reddish blue |
| 211 | $SO_3H$ | 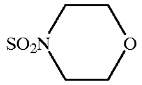 | H | $CH_2CH_2C_6H_5$ | reddish blue |
| 212 | H | 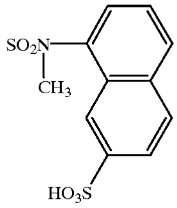 | H | $C_2H_5$ | reddish blue |
| 213 | H | 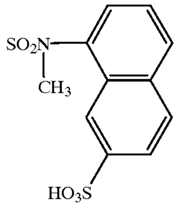 | H | $CH_2CH_2C_6H_5$ | reddish blue |

TABLE 11-continued

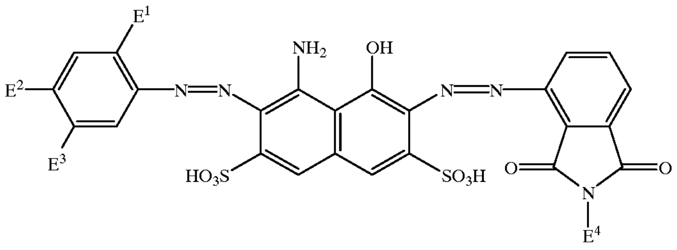

| Ex. No. | $E^1$ | $E^2$ | $E^3$ | $E^4$ | |
|---|---|---|---|---|---|
| 214 | H | 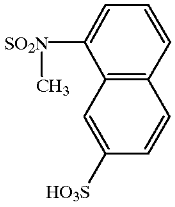 | H | $CH_2C_6H_5$ | reddish blue |
| 215 | H | 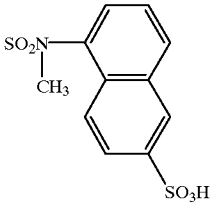 | H | $C_4H_9$ | reddish blue |
| | | | | | Hue on wool/ $\lambda_{max}$ [nm] at pH 4 |
| 216 | $SO_2OC_6H_5$ | H | H | $CH_2C_6H_5$ | reddish blue |
| 217 | $SO_2OC_6H_5$ | H | H | 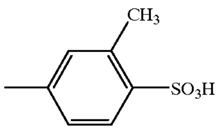 | reddish blue |
| 218 | $CH_3$ | H | 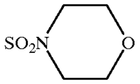 | 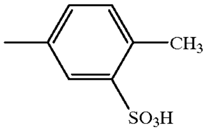 | reddish blue |
| 219 | H | $SO_2CH_2CH_2OSO_3H$ | H | $CH_2CH_2C_6H_5$ | 392 and 593 |
| 220 | H | $SO_2CH_2CH_2OSO_3H$ | H | $CH_2CH_2CH_2OC_2H_5$ | 392 and 594 |
| 221 | H | $SO_2CH_2CH_2OSO_3H$ | H | $CH_2C_6H_5$ | 392 and 593 |
| 222 | H | $SO_2CH_2CH_2OSO_3H$ | H | $CH_2CH_2CH_2OCH_3$ | 392 and 594 |
| 223 | H | $SO_2CH_2CH_2Cl$ | H | $CH_2CH_2OC_4H_9$ | 392 and 594 |
| 224 | H | $SO_2CH_2CH_2OCOCH_3$ | H | $CH_2CH_2OCH_2C_6H_5$ | 392 and 593 |
| 225 | H | $SO_2CH_2CH_2OSO_3H$ | H | 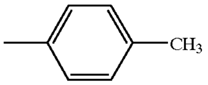 | 393 and 591 |
| 226 | H | $SO_2CH_2CH_2OSO_3H$ | H | 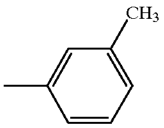 | 393 and 591 |

TABLE 11-continued

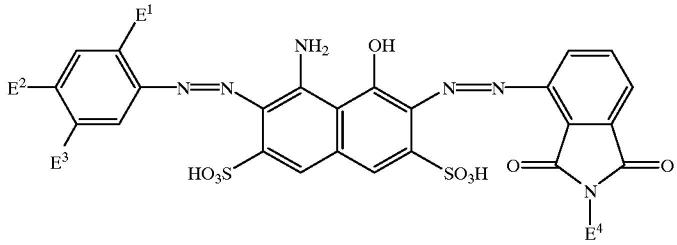

| Ex. No. | $E^1$ | $E^2$ | $E^3$ | $E^4$ | |
|---|---|---|---|---|---|
| 227 | H | $SO_2CH{=}CH_2$ | H | 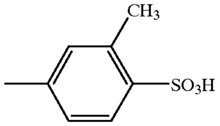 | 394 and 595 |
| 228 | H | $SO_2CH_2CH_2OCOCH_3$ | H | 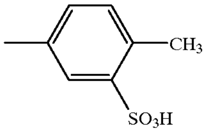 | reddish blue |
| 229 | H | $SO_2CH_2CH_2Cl$ | H | 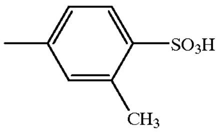 | reddish blue |
| 230 | $SO_3H$ | $SO_2CH_2CH_2OSO_3H$ | H | $C_4H_9$ | reddish blue |
| 231 | $SO_3H$ | $SO_2CH_2CH_2OSO_3H$ | H | 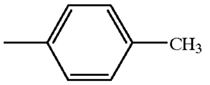 | reddish blue |
| 232 | $SO_2CH_2CH_2OSO_3H$ | H | H | $CH_2CH_2OH$ | reddish blue |
| 233 | H | H | $SO_2CH_2CH_2OSO_3H$ | $CH_2C_6H_5$ | reddish blue |
| 234 | H | $NO_2$ | H | $(CH_2)_5CO_2H$ | reddish blue |
| 235 | H | $SO_2CH_2CH_2OSO_3H$ | H | 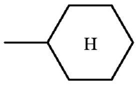 | reddish blue |

TABLE 12

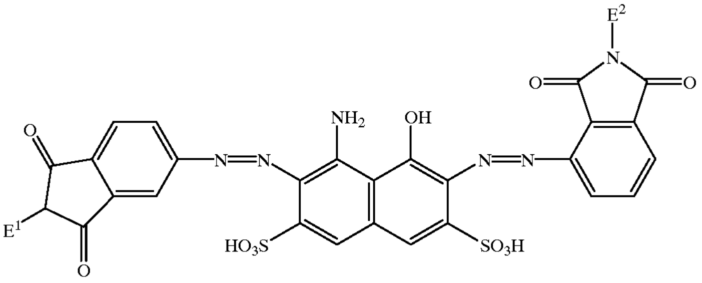

| Ex. No. | $E^1$ | $E^2$ | Hue on wool |
|---|---|---|---|
| 236 | $CH_2CH{=}CH_2$ | $CH_2CH_2OC_4H_9$ | reddish blue |

TABLE 12-continued
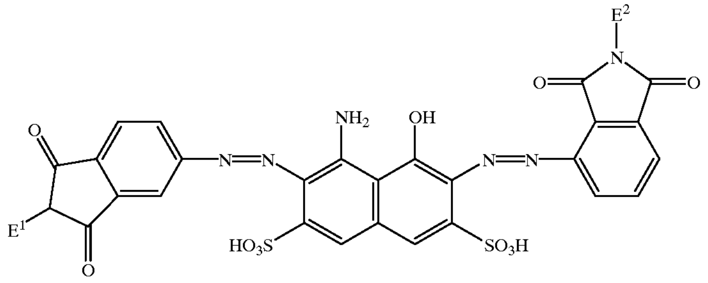
| Ex. No. | $E^1$ | $E^2$ | Hue on wool |
|---|---|---|---|
| 237 | 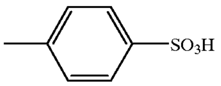 | $CH_2CH_2C_6H_5$ | reddish blue |
| 238 | 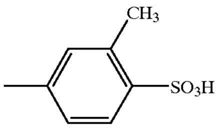 | $CH_2CH_2C_6H_5$ | reddish blue |
| 239 | 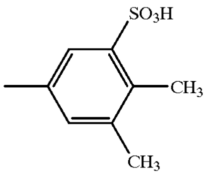 | $CH_2CH_2C_6H_5$ | reddish blue |
| 240 | 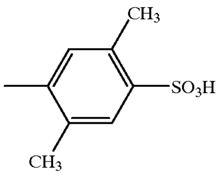 | $CH_2CH_2C_6H_5$ | reddish blue |
| 241 | 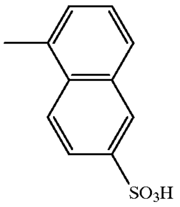 | $CH_2CH_2C_6H_5$ | reddish blue |
| 242 | 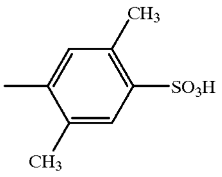 | $CH_2C_6H_5$ | reddish blue |
| 243 | $C_2H_4OH$ | 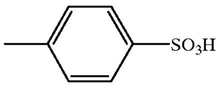 | reddish blue |
| 244 | $C_3H_6OH$ | 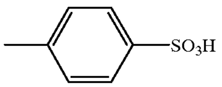 | reddish blue |

TABLE 12-continued
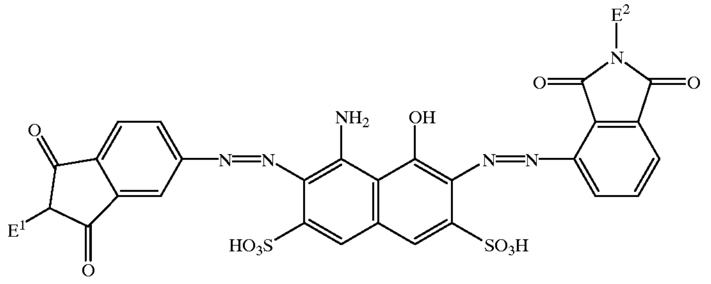
| Ex. No. | $E^1$ | $E^2$ | Hue on wool |
|---|---|---|---|
| 245 | $C_4H_8OH$ | 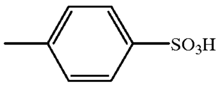 | reddish blue |
| 246 | $CH_2C_6H_5$ | 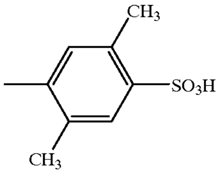 | reddish blue |
| 247 | $C_2H_4OH$ | 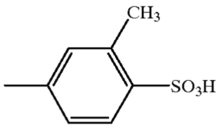 | reddish blue |
| 248 | 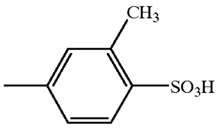 | $C_4H_9$ | reddish blue |
TABLE 13
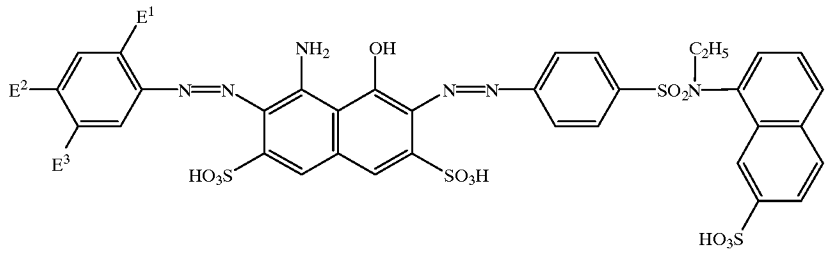
| Ex. No. | $E^1$ | $E^2$ | $E^3$ | Hue on wool |
|---|---|---|---|---|
| 249 | 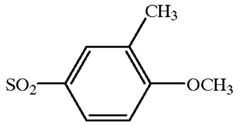 | H | H | reddish blue |
| 250 | 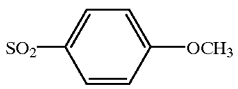 | H | H | reddish blue |

TABLE 13-continued
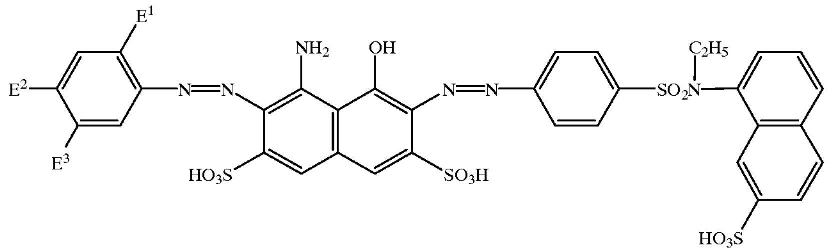
| Ex. No. | $E^1$ | $E^2$ | $E^3$ | Hue on wool |
|---|---|---|---|---|
| 251 | 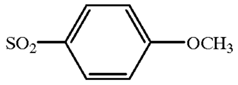 | H | $SO_2CH_3$ | blue |
| 252 | 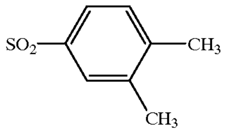 | H | $SO_2CH_2CO_2H$ | blue |
| 253 | $SO_2OC_6H_5$ | H | H | reddish blue |
| 254 | $SO_2OC_6H_5$ | $CH_3$ | H | reddish blue |
| 255 | $SO_2OC_6H_5$ | H | H | reddish blue |
| 256 | H | 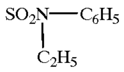 | H | blue |
| 257 | H | 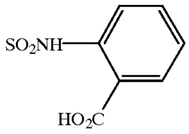 | H | blue |
| 258 | H | H | 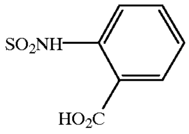 | blue |
| 259 | H | H | $SO_2OC_6H_5$ | blue |
| 260 | Cl | H | $SO_2OC_6H_5$ | blue |
| 261 | H | $CH_3$ | $SO_2OC_6H_5$ | blue |

TABLE 14

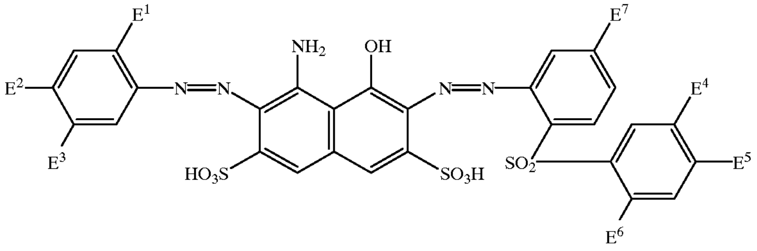

| Ex. No. | $E^1$ | $E^2$ | $E^3$ | $E^4$ | $E^5$ | $E^6$ | $E^7$ | Hue on wool |
|---|---|---|---|---|---|---|---|---|
| 262 | H | 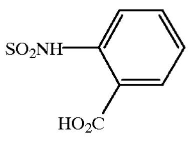 | H | H | $CH_3$ | H | $SO_3H$ | bluish black |
| 263 | H | 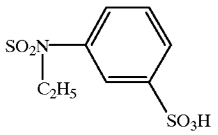 | H | H | $CH_3$ | H | H | bluish black |
| 264 | H | $CH_3$ | 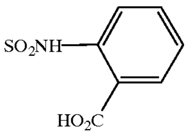 | H | $CH_3$ | H | $SO_3H$ | bluish black |
| 265 | H | $CH_3$ | 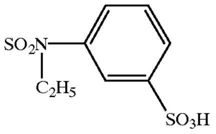 | H | $CH_3$ | H | H | dark blue |
| 266 | H | $CH_3$ | 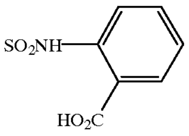 | $CH_3$ | $CH_3$ | H | $SO_3H$ | bluish black |
| 267 | Cl | H | $SO_2O—C_6H_5$ | $CH_3$ | $OCH_3$ | H | $SO_3H$ | bluish black |
| 268 | H | H | $SO_2O—C_6H_5$ | $CH_3$ | H | $CH_3$ | $SO_3H$ | bluish black |
| 269 | H | 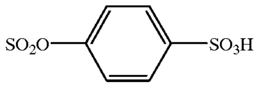 | H | $CH_3$ | $CH_3$ | H | H | bluish black |
| 270 | H | H | 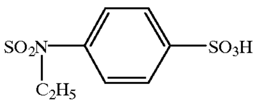 | $CH_3$ | $CH_3$ | H | H | dark blue |
| 271 | H | 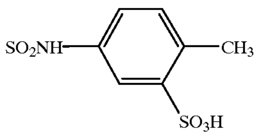 | H | $CH_3$ | $CH_3$ | H | H | dark blue |

TABLE 15
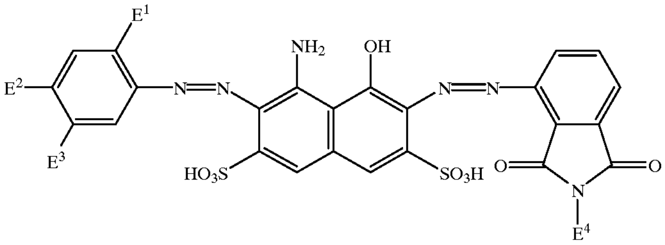
| Ex. No. | E[1] | E[2] | E[3] | E[4] | Hue on wool |
|---|---|---|---|---|---|
| 272 | H | 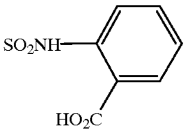 | H | 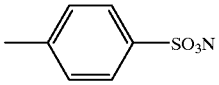 | blue |
| 273 | H | $CH_3$ | 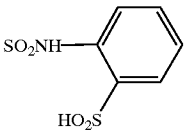 | $CH_2C_6H_5$ | blue |
| 274 | H | 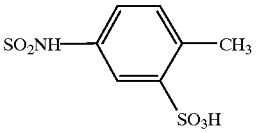 | H | $CH_2C_6H_5$ | blue |
| 275 | H | 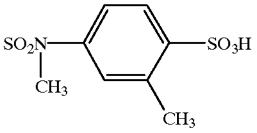 | H | $CH_2C_6H_5$ | blue |
| 276 | H | $CH_3$ | 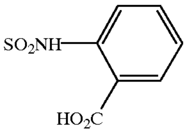 | 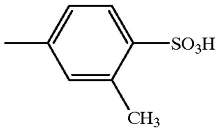 | blue |
| 277 | H | H | 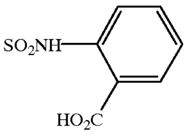 | 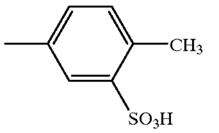 | blue |
| 278 | Cl | H | 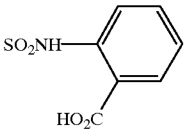 | 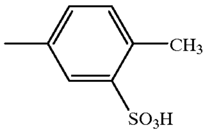 | blue |
| 279 | H | H | 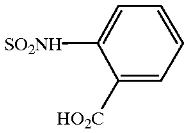 | 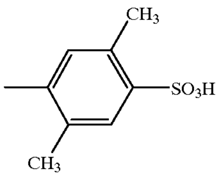 | blue |

TABLE 15-continued
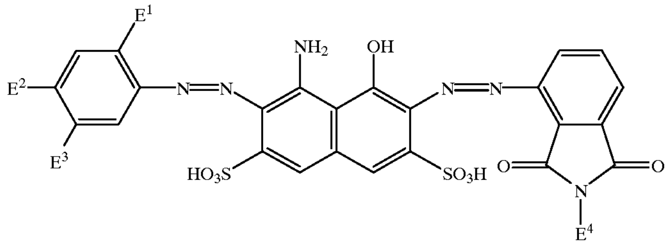
| Ex. No. | E¹ | E² | E³ | E⁴ | Hue on wool |
|---|---|---|---|---|---|
| 280 | H | 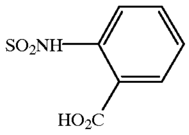 | H | 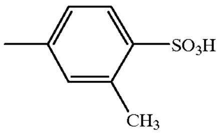 | blue |
| 281 | H | 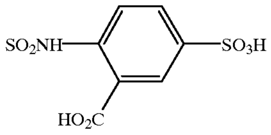 | H | $C_4H_9$ | blue |
| 282 | H | 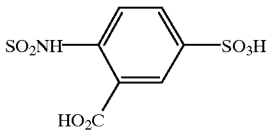 | H | $C_3H_6OCH_3$ | blue |
TABLE 16
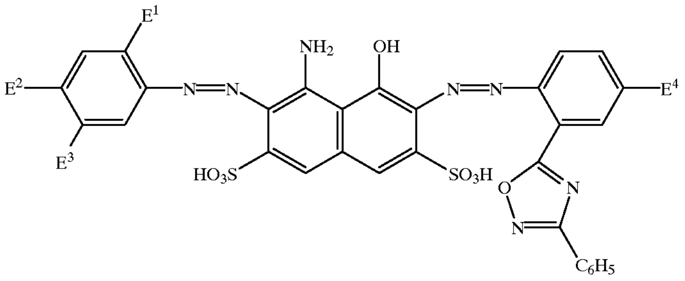
| Ex. No. | E¹ | E² | E³ | E⁴ | Hue on wool |
|---|---|---|---|---|---|
| 283 | H | 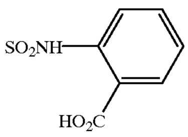 | H | $SO_3H$ | reddish blue |
| 284 | $CH_3$ | $CH_3$ | 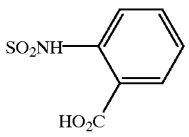 | $SO_3H$ | reddish blue |

TABLE 16-continued
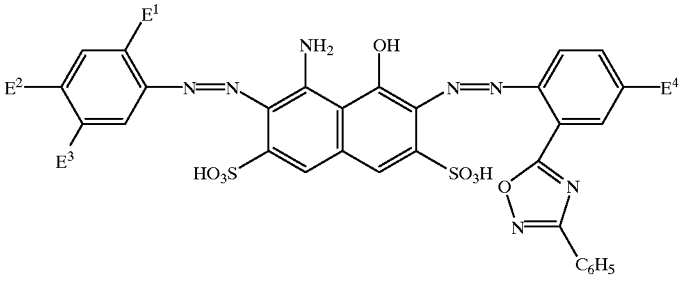
| Ex. No. | $E^1$ | $E^2$ | $E^3$ | $E^4$ | Hue on wool |
|---|---|---|---|---|---|
| 285 | $CH_3$ | H | 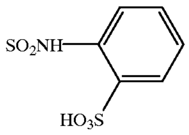 | H | reddish blue |
| 286 | H | H | 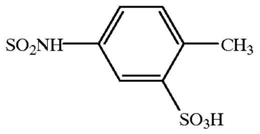 | H | reddish blue |
| 287 | H | H | 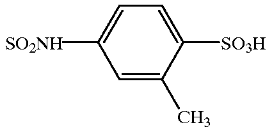 | H | reddish blue |
| 288 | H | H | 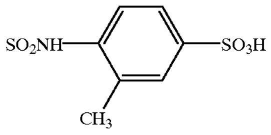 | H | reddish blue |
| 289 | $CH_3$ | 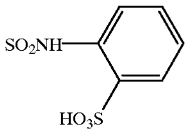 | H | H | reddish blue |
| 290 | H | 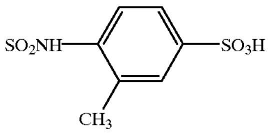 | H | H | reddish blue |
| 291 | H | 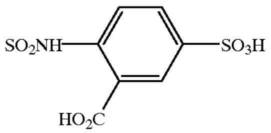 | H | H | reddish blue |
| 292 | H | 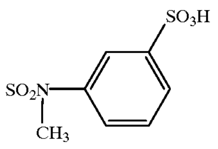 | H | H | reddish blue |

TABLE 16-continued
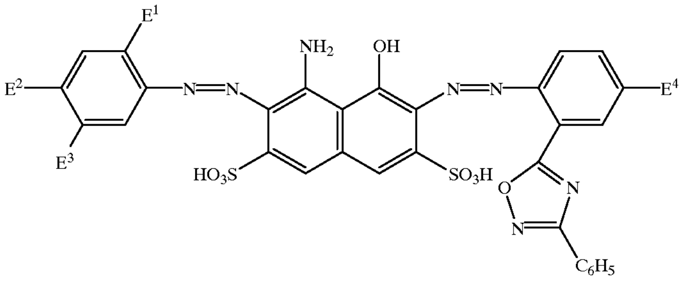
| Ex. No. | $E^1$ | $E^2$ | $E^3$ | $E^4$ | Hue on wool |
|---|---|---|---|---|---|
| 293 | H | 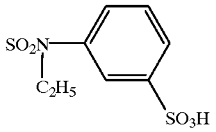 | H | H | reddish blue |
| 294 | H | 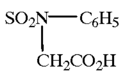 | H | H | reddish blue |
TABLE 17
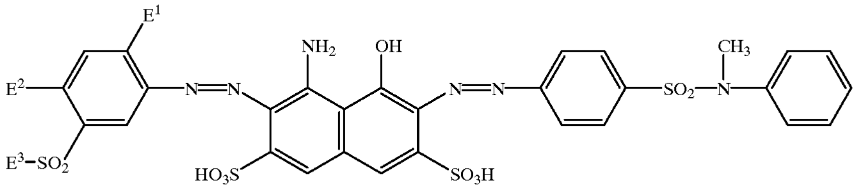
| Ex. No. | $E^1$ | $E^2$ | $E^3$ | Hue on wool |
|---|---|---|---|---|
| 295 | H | $CH_3$ | 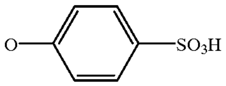 | blue |
| 296 | Cl | H | 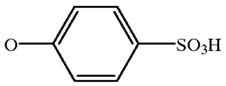 | blue |
| 297 | H | H | 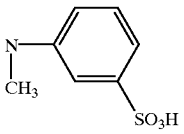 | blue |
| 298 | H | H | 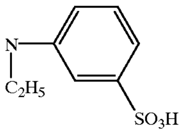 | blue |

TABLE 17-continued
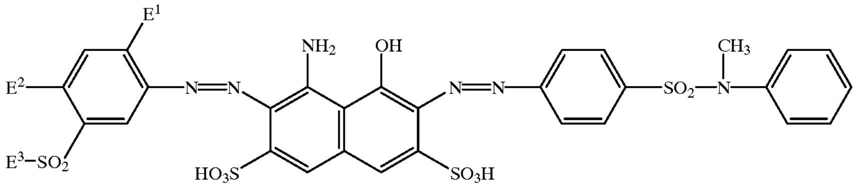
| Ex. No. | $E^1$ | $E^2$ | $E^3$ | Hue on wool |
|---|---|---|---|---|
| 299 | H | $CH_3$ | 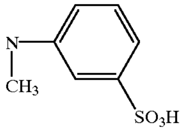 | blue |
| 300 | H | H | 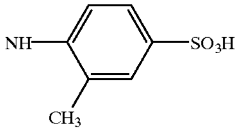 | blue |
| 301 | H | H | 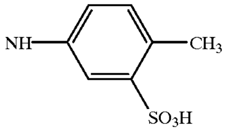 | blue |
| 302 | H | H | 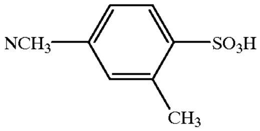 | blue |
| 303 | H | H | 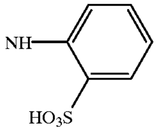 | blue |
| 304 | H | H | 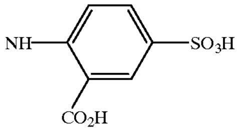 | blue |
| 305 | H | H | 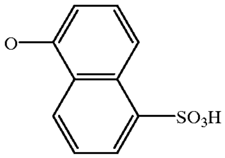 | blue |

TABLE 18
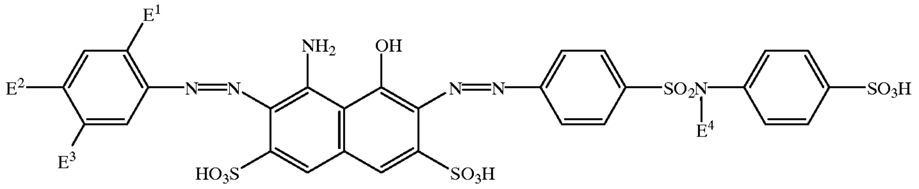
| Ex. No. | $E^1$ | $E^2$ | $E^3$ | $E^4$ | Hue on wool |
|---|---|---|---|---|---|
| 306 | H | $NO_2$ | H | $C_4H_9$ | blue |
| 307 | H | $C_6H_5SO_2$ | H | $C_2H_5$ | blue |
| 308 | H | 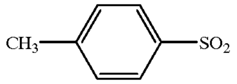 | H | $C_2H_5$ | blue |
| 309 | H | 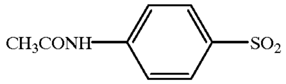 | H | $C_2H_5$ | blue |
| 310 | 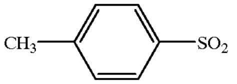 | H | $(C_2H_5)_2N—SO_2$ | $C_2H_5$ | bluish black |
| 311 | 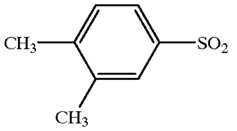 | H | $(C_2H_5)_2N—SO_2$ | $C_2H_5$ | bluish black |
| 312 | H | $CH_2═CH—SO_2$ | H | $C_2H_5$ | blue |
| 313 | H | $HOCH_2CH_2—SO_2$ | H | $C_2H_5$ | blue |
| 314 | H | $CH_3CO_2C_2H_4—SO_2$ | H | $C_2H_5$ | blue |
| 315 | H | $ClCH_2CH_2—SO_2$ | H | $CH_3$ | blue |
| 316 | H | $CH_2═CH—SO_2$ | H | $CH_3$ | blue |
| 317 | 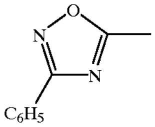 | H | H | $CH_3$ | blue |
| 318 | H | 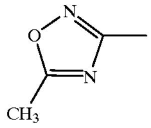 | H | $C_2H_5$ | blue |
| 319 | H | H | 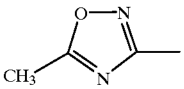 | $C_2H_5$ | blue |
| 320 | H | 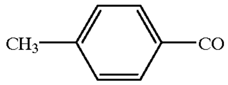 | H | $C_2H_5$ | blue |
| 321 | H | 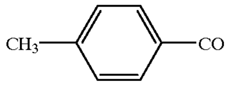 | H | $C_2H_5$ | blue |
| 322 | H | $C_2H_5O_2C$ | H | $C_2H_5$ | blue |

TABLE 18-continued

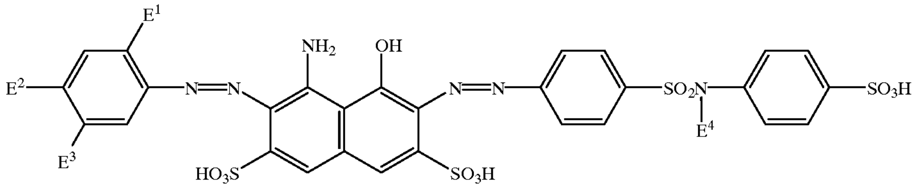

| Ex. No. | $E^1$ | $E^2$ | $E^3$ | $E^4$ | Hue on wool |
|---|---|---|---|---|---|
| 323 | H | | 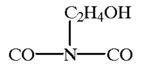 | $C_2H_5$ | blue |
| 324 | H | | 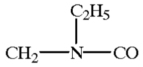 | $C_2H_5$ | blue |
| 325 | H | | 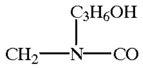 | $C_2H_5$ | blue |
| 326 | 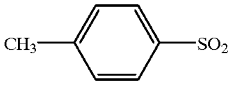 | H | $SO_2CH_2CO_2H$ | $CH_3$ | bluish black |
| 327 | 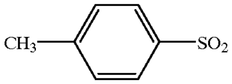 | H | $SO_2CH_2CO_2H$ | $C_2H_5$ | bluish black |
| 328 | 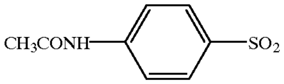 | H | $SO_2CH_2CO_2H$ | $CH_3$ | bluish black |
| 329 | 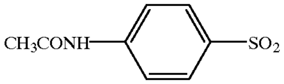 | H | $SO_2CH_2CO_2H$ | $CH_3$ | bluish black |
| 330 | $C_6H_5$—$SO_2$ | H | 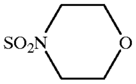 | $CH_3$ | bluish black |
| 331 | $C_6H_5$—$SO_2$ | H | 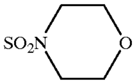 | $C_2H_5$ | bluish black |
| 332 | 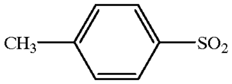 | H | 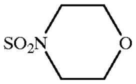 | $C_2H_5$ | bluish black |
| 333 | 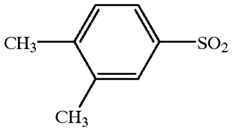 | H | 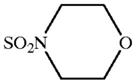 | $CH_3$ | bluish black |
| 334 | $CO_2CH_3$ | H | $CO_2CH_3$ | $CH_3$ | blue |
| 335 | $CO_2CH_3$ | H | $CO_2CH_3$ | $C_2H_5$ | blue |
| 336 | $CO_2C_2H_5$ | H | $CO_2C_2H_5$ | $CH_3$ | blue |
| 337 | $CO_2C_2H_5$ | H | $CO_2C_2H_5$ | $C_2H_5$ | blue |
| 338 | $CO_2CH_3$ | H | $CO_2C_3H_7$ | $CH_3$ | blue |
| 339 | $CO_2CH_3$ | H | $CO_2C_6H_5$ | $CH_3$ | blue |

TABLE 18-continued

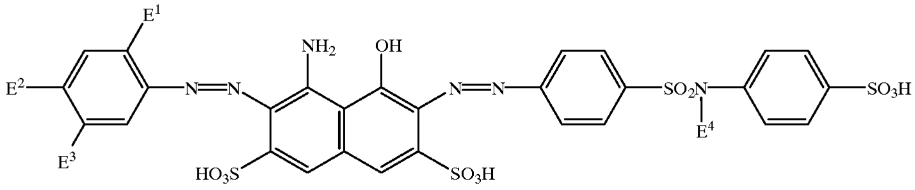

| Ex. No. | $E^1$ | $E^2$ | $E^3$ | $E^4$ | Hue on wool |
|---|---|---|---|---|---|
| 340 | $CO_2CH_3$ | H | $CO_2C_6H_5$ | $CH_3$ | blue |

TABLE 19

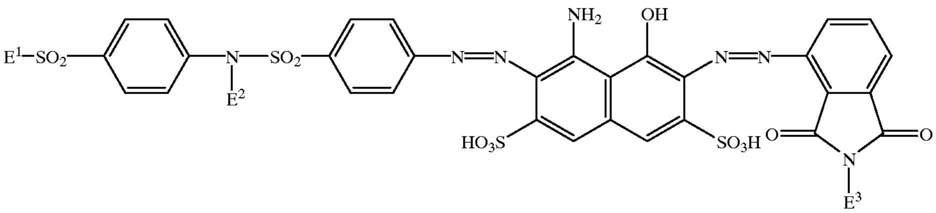

| Ex. No. | $E^1$ | $E^2$ | $E^3$ | Hue on wool |
|---|---|---|---|---|
| 341 | $HO_3SOCH_2CH_2$ | $CH_3$ | $CH_2C_6H_5$ | reddish blue |
| 342 | $HO_3SOCH_2CH_2$ | $C_2H_5$ | $CH_2C_6H_5$ | reddish blue |
| 343 | $HO_3SOCH_2CH_2$ | $CH_3$ | $CH_2CH_2C_6H_5$ | reddish blue |
| 344 | $HO_3SOCH_2CH_2$ | $CH_3$ | $CH_2CH_2OCH_3$ | reddish blue |
| 345 | $HO_3SOCH_2CH_2$ | $CH_3$ | $(CH_2)_3OCH_3$ | reddish blue |
| 346 | $HO_3SOCH_2CH_2$ | $C_2H_5$ | $(CH_2)_3OCH_2C_6H_5$ | reddish blue |
| 347 | $HO_3SOCH_2CH_2$ | $CH_3$ | $C_6H_5$ | reddish blue |
| 348 | $HO_3SOCH_2CH_2$ | $CH_3$ | 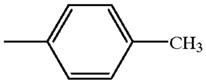 | reddish blue |
| 349 | $HOCH_2CH_2$ | $CH_3$ | 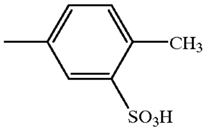 | blue |
| 350 | $H_2C{=}CH$ | $C_2H_5$ | 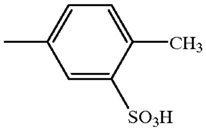 | blue |
| 351 | $HOCH_2CH_2$ | $C_2H_5$ | 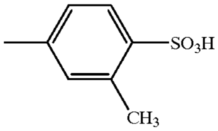 | blue |
| 352 | 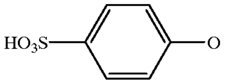 | $CH_3$ | $CH_2C_6H_5$ | reddish blue |

TABLE 19-continued

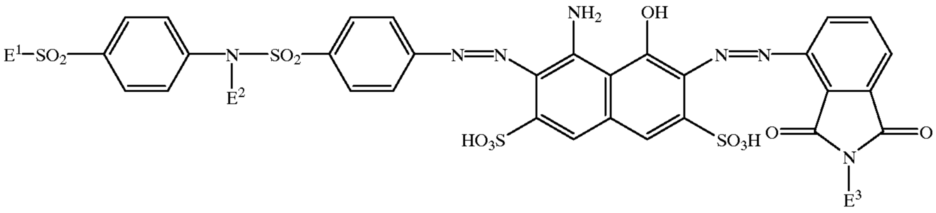

| Ex. No. | $E^1$ | $E^2$ | $E^3$ | Hue on wool |
|---|---|---|---|---|
| 353 | $HOC_2H_4$ | $CH_3$ | 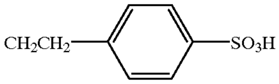 | reddish blue |
| 354 | $HOC_2H_4$ | $C_2H_5$ | 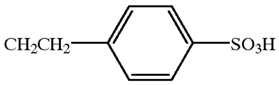 | reddish blue |
| 355 | $HO_2CCH_2$ | $C_2H_5$ | 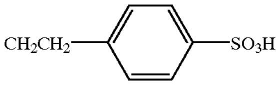 | reddish blue |
| 356 | $HO_3SOCH_2CH_2$ | $C_2H_5$ | $CH_2CO_2H$ | reddish blue |

TABLE 20

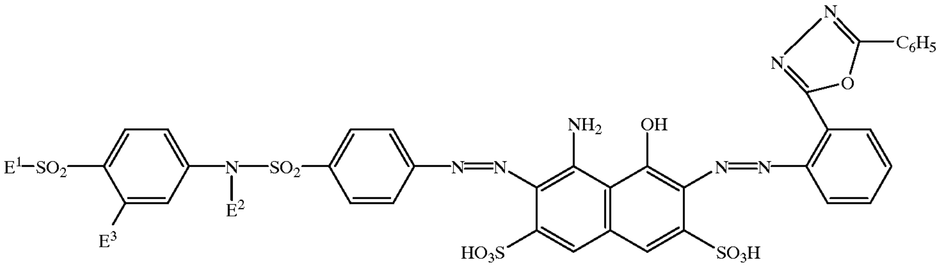

| Ex. No. | $E^1$ | $E^2$ | $E^3$ | Hue on wool |
|---|---|---|---|---|
| 357 | $HO_3SOCH_2CH_2$ | $CH_3$ | H | reddish blue |
| 358 | $HO_3SOCH_2CH_2$ | $C_2H_5$ | H | reddish blue |
| 359 | $HO_3SOCH_2CH_2$ | $C_3H_7$ | H | reddish blue |
| 360 | 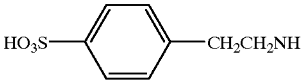 | $CH_3$ | H | reddish blue |
| 361 | 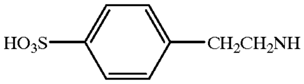 | $C_2H_5$ | H | reddish blue |
| 362 | 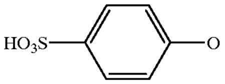 | $CH_3$ | H | reddish blue |
| 363 | 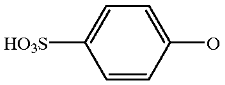 | $C_2H_5$ | H | reddish blue |

TABLE 20-continued

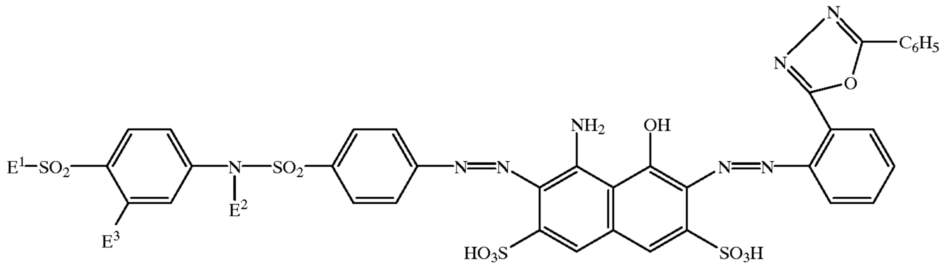

| Ex. No. | $E^1$ | $E^2$ | $E^3$ | Hue on wool |
|---|---|---|---|---|
| 364 | $HO_2CCH_2$ | $CH_3$ | H | reddish blue |
| 365 | $(HOCH_2CH_2)_2N$ | $CH_3$ | H | reddish blue |
| 366 | $HOCH_2CH_2NH$ | $CH_3$ | H | reddish blue |
| 367 | $HOCH_2CH_2NH$ | $C_2H_5$ | H | reddish blue |
| 368 | $HO_2CCH_2NH$ | $C_2H_5$ | H | reddish blue |
| 369 | $HO_2CCH_2CH_2NH$ | $CH_3$ | H | reddish blue |
| 370 | $HO_2CCH_2CH_2NH$ | $C_2H_5$ | H | reddish blue |
| 371 | $HO_3SOCH_2CH_2$ | $CH_3$ | $CH_3$ | reddish blue |

TABLE 21

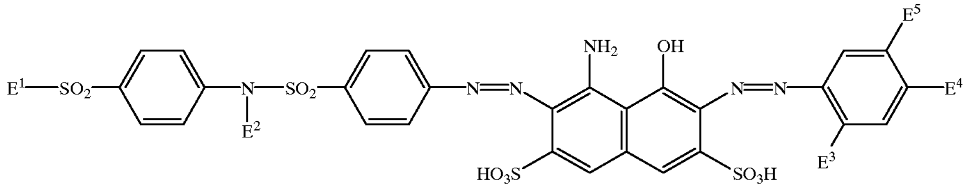

| Ex. No. | $E^1$ | $E^2$ | $E^3$ | $E^4$ | $E^5$ | Hue on wool |
|---|---|---|---|---|---|---|
| 372 | $HO_2CCH_2$ | $CH_3$ | 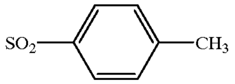 | H | $SO_3H$ | bluish black |
| 372 | $HO_2CCH_2$ | $C_2H_5$ | 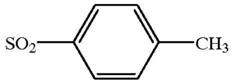 | H | $SO_3H$ | bluish black |
| 374 | $HOCH_2CH_2$ | $C_2H_5$ | 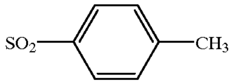 | H | $SO_3H$ | bluish black |
| 375 | $HO_3SOCH_2CH_2$ | $CH_3$ | 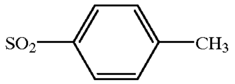 | H | H | blue |
| 376 | $HO_3SOCH_2CH_2$ | $C_2H_5$ | 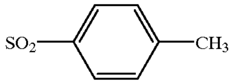 | H | H | blue |
| 377 | $HO_3SOCH_2CH_2$ | $CH_3$ | 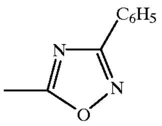 | H | H | reddish blue |

TABLE 21-continued

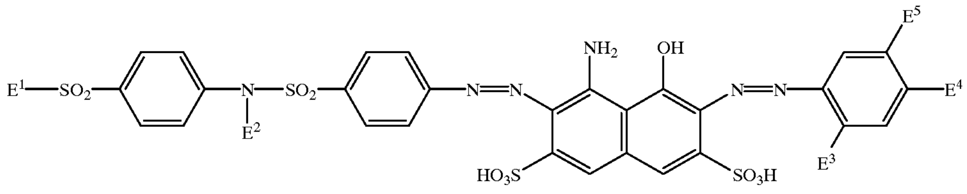

| Ex. No. | $E^1$ | $E^2$ | $E^3$ | $E^4$ | $E^5$ | Hue on wool |
|---|---|---|---|---|---|---|
| 378 | $HO_3SOCH_2CH_2$ | $C_2H_5$ | 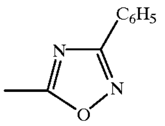 | H | H | reddish blue |
| 379 | $HO_3SOCH_2CH_2$ | $C_2H_5$ | 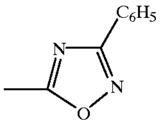 | $SO_2N(C_2H_4OCH_3)_2$ | H | reddish blue |
| 380 | $HO_3SOCH_2CH_2$ | $C_2H_5$ | $COC_6H_5$ | H | H | reddish blue |
| 381 | $HO_3SOCH_2CH_2$ | $C_2H_5$ | $COC_6H_5$ | Cl | H | reddish blue |
| 382 | $CH_2{=}CH$ | $CH_3$ | $SO_2C_6H_5$ | H | $SO_3H$ | bluish black |
| 383 | $CH_2{=}CH$ | $C_2H_5$ | $SO_2C_6H_5$ | H | $SO_3H$ | bluish black |
| 384 | 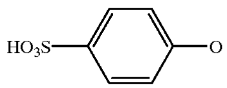 | $C_2H_5$ | $SO_2C_6H_5$ | H | H | blue |
| 385 | $(HOC_2H_4)_2N$ | $CH_3$ | 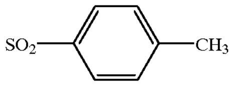 | H | $SO_3H$ | bluish black |
| 386 | $CH_2{=}CHCH_2$ | $CH_3$ | 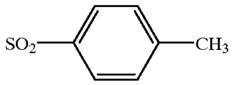 | H | $SO_3H$ | bluish black |
| 387 | $CH_2{=}CHCH_2$ | $C_2H_5$ | 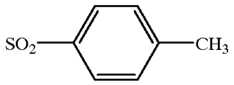 | H | $SO_3H$ | bluish black |
| 388 | $HO_3SOCH_2CH_2$ | $C_2H_5$ | $CO_2C_6H_5$ | H | H | blue |
| 389 | $HO_3SOCH_2CH_2$ | $C_2H_5$ | $CO_2CH_2CH_2C_6H_5$ | H | H | blue |
| 390 | $HO_3SOCH_2CH_2$ | $C_2H_5$ | $CO_2CH_2CH_2OC_6H_5$ | H | H | blue |
| 391 | $HO_3SOCH_2CH_2$ | $C_2H_5$ | $CO_2CH_3$ | H | H | blue |
| 392 | 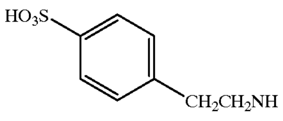 | $C_2H_5$ | 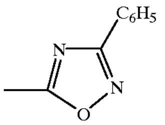 | H | H | reddish blue |

TABLE 22

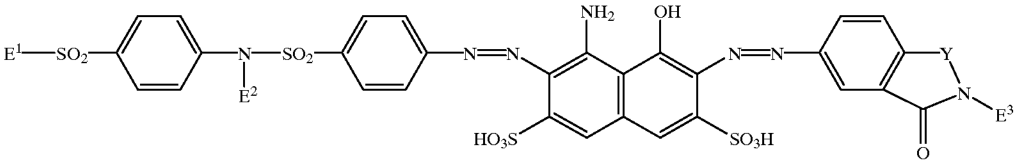

| Ex. No. | $E^1$ | $E^2$ | $E^3$ | Y | Hue on wool |
|---|---|---|---|---|---|
| 393 | $HOCH_2CH_2NH$ | $CH_3$ | $CH_2C_6H_5$ | CO | blue |
| 394 | $(HOCH_2CH_2)_2N$ | $CH_3$ | $CH_2C_6H_5$ | CO | blue |
| 395 | 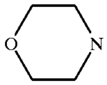 | $CH_3$ | 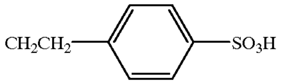 | CO | blue |
| 396 | 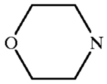 | $C_2H_5$ | 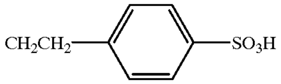 | CO | blue |
| 397 | $HOCH_2CH_2$ | $C_2H_5$ | 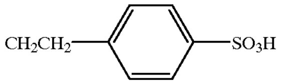 | CO | blue |
| 398 | $CH_2{=}CHCH_2$ | $C_2H_5$ | 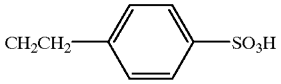 | CO | blue |
| 399 | $CH_2{=}CHCH_2$ | $C_2H_5$ | 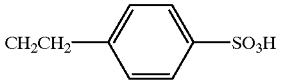 | $CH_2$ | blue |
| 400 | $HO_3SOCH_2CH_2$ | $CH_3$ | $CH_2CH_2OCH_3$ | $CH_2$ | blue |
| 401 | $HO_3SOCH_2CH_2$ | $C_2H_5$ | $CH_2CH_2CH_2OCH_2C_6H_5$ | $CH_2$ | blue |
| 402 | $HO_3SOCH_2CH_2$ | $C_2H_5$ | $C_2H_5$ | CO | blue |
| 403 | $HO_3SOCH_2CH_2$ | $C_2H_5$ | $CH_2C_6H_5$ | CO | blue |
| 404 | $HO_2CCH_2$ | $CH_3$ | $CH_2CH_2C_6H_5$ | CO | blue |
| 405 | $HO_2CCH_2$ | $C_2H_5$ | 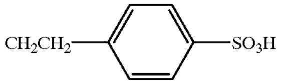 | $CH_2$ | blue |
| 406 | $HO_2CCH_2$ | $CH_3$ | 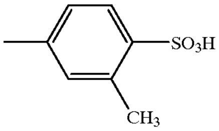 | $CH_2$ | blue |
| 407 | $HO_2CCH_2$ | $CH_3$ | 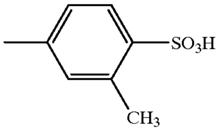 | CO | blue |
| 408 | $HO_2CCH_2$ | $C_2H_5$ | 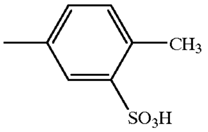 | CO | blue |

TABLE 22-continued

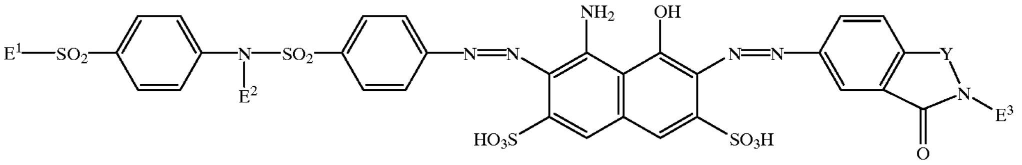

| Ex. No. | $E^1$ | $E^2$ | $E^3$ | Y | Hue on wool |
|---|---|---|---|---|---|
| 409 | 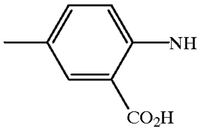 | $CH_3$ | 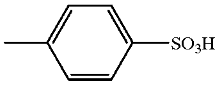 | CO | blue |
| 410 | $HOCH_2CH_2$ | $C_2H_5$ | 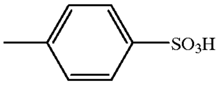 | CO | blue |
| 411 | $HOCH_2CH_2$ | $C_2H_5$ | 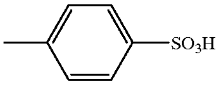 | $CH_2$ | blue |
| 412 | $H_2C{=}CH$ | $C_2H_5$ | 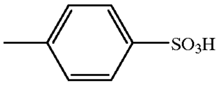 | $CH_2$ | blue |

EXAMPLE 413 a) 16.9 g of the diazo component of formula

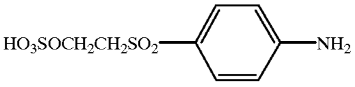

were dissolved in 30 ml of water at pH 3.5 using 5.9 g of sodium bicarbonate, and the solution was then cooled down with ice to 0° C. and admixed with 12.6 ml of 36% strength hydrochloric acid. The suspension was then diazotized with 18.3 ml of 3.33 N aqueous sodium nitrite solution. The resulting diazonium salt mixture was mixed with a freshly precipitated suspension of 20.5 g of 1-amino-8-hydroxynaphthalene-3,6-disulfonic acid monosodium salt (pH about 1) after excess nitrous acid had been destroyed. The mixture was coupled overnight to obtain a suspension of the red dye of the formula

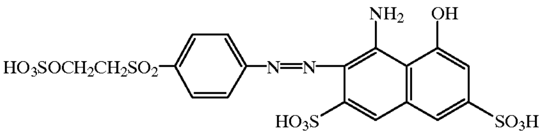

b) The suspension obtained was adjusted to pH 10 at room temperature and the resulting solution was stirred at pH 10 for 3.5 h. The pH was then adjusted to 7, 0.06 mol of the conventionally prepared diazonium salt of diethyl 2-aminoterephthalate was added in the form of a solution, and the mixture was subsequently stirred for 3 h at pH 6–7. The resulting blue dye was precipitated with sodium chloride at pH 6–6.5 and isolated in a conventional manner.

Drying left 50 g of the dye of the formula

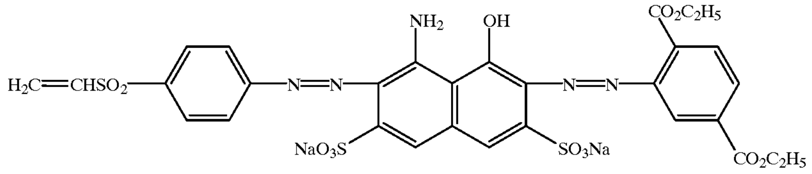

which still comprised a total of 16 g of sodium chloride and water of crystallization. The dye forms a blue solution in water with absorption maxima in the visible region at 396 and 582 nm and a shoulder at 625 nm.

Dark blue to bluish black dyeings are obtained on wool according to the customary dyeing methods for anionic wool dyes. The buildup capacity and also the wet- and lightfastness properties on wool are excellent.

EXAMPLE 414

The dye described in Example 413 a) as a suspension was neutralized. Then 0.06 mol of the diazonium salt solution of diethyl 2-aminoterephthalate was added while the pH of the coupling solution was maintained at from 5.5 to 7.0 using sodium bicarbonate. The ready-prepared coupling mixture was spray-dried at pH 6.5, affording the dye of the formula

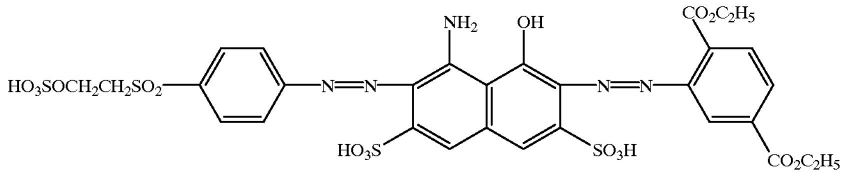

as a bluish black powder (together with the salts formed in the course of the reaction) in the form of the sodium salt. The powder forms a blue solution in water ($\lambda_{max}$ in water: 397 and 585 nm, shoulder at 626 nm) and dyes wool according to the dyeing processes customary for wool dyes (acetic acid to formic acid medium) in a blue to bluish black shade having excellent light- and wetfastness properties.

EXAMPLE 415 a) The dye described in 413 a) as a suspension was neutralized.

Then 0.06 mol of the diazonium salt of 4-aminodiphenyl sulfone (diazotized in water in a conventional manner with hydrochloric acid and sodium nitrite) was added and the pH of the coupling mixture was maintained at 5–7. The mixture was subsequently stirred for 1 h at pH 6.5 and thereafter spray-dried, affording a black powder comprising 51 g of the dye of the formula

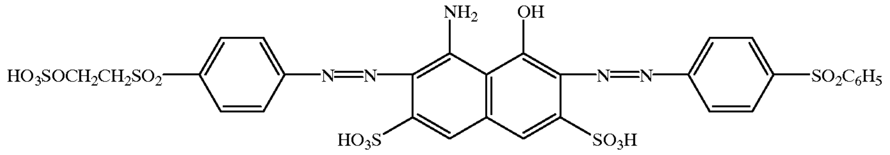

in the form of the sodium salt ($\lambda_{max}$ in water: 600 nm, at pH 4–6). The dye dyes wool in a deep bluish black shade having excellent wetfastness properties and good lightfastness.

b) However, on adjusting the blue reaction solution to pH 10 and subsequently stirring it at room temperature for 4 h, the resulting novel dye of the formula

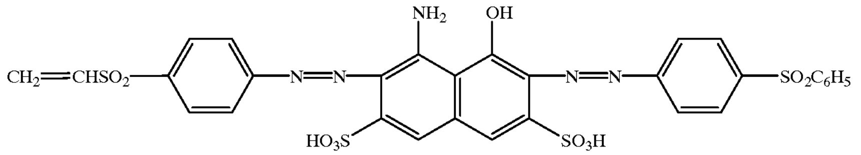

was readily precipitated with sodium chloride at pH 6.5. This dye dyes wool according to the customary dyeing processes (acetic-formic acid medium) in a dark blue to black shade having excellent wetfastness properties, similarly to the dye described under a). Blue dyeings are obtained on leather ($\lambda_{max}$ in water: at pH ~4 to 5: 392 and 596 nm)

EXAMPLE 416

The dye described in Example 413 a) as a suspension was neutralized at room temperature. Then 0.06 mol of the diazonium salt of the formula

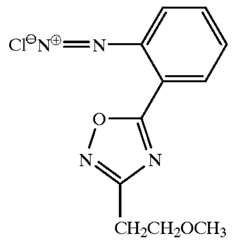

was added in the form of an aqueous solution and the pH of the coupling reaction was held within the range from 5.5 to 7.5 using sodium bicarbonate, affording a solution of the dye of the formula

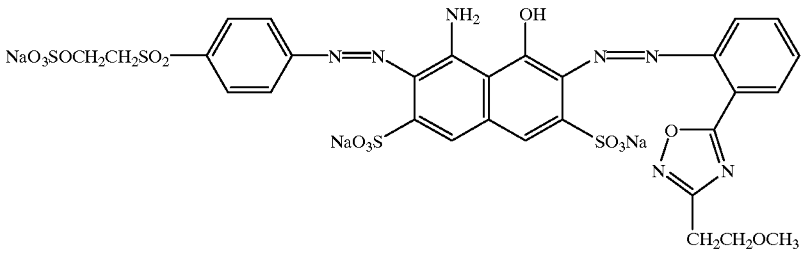

Spray drying at a pH from about 6 to 6.5 gave a black powder which forms a blue solution in water. The absorption spectrum in the visible region had maxima at 394 nm and 584 nm and also a shoulder at about 620 nm.

Adjusting the dye solution to pH 10 and stirring at room temperature for 4 h yielded the novel dye of the formula

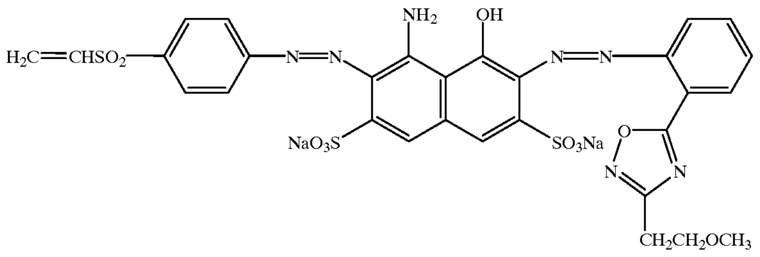

($\lambda_{max}$ in water at pH 4–6: 581 nm, shoulder at about 618 nm). This dye could be precipitated with sodium chloride at pH 6–7.5 and isolated in a conventional manner.

Both dyes dye wool in a dark blue to navy shade having excellent wet- and lightfastness properties. The exhaustion capacity is good.

EXAMPLE 417 a) 29.6 g of the diazo component of the formula

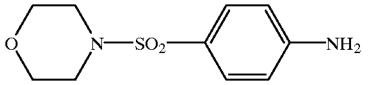

were dissolved using 72 ml of 18.5% strength by weight hydrochloric acid. Ice was added, followed at 0–7° C. by 37.5 ml of 23% strength aqueous sodium nitrite solution. The mixture was subsequently stirred at 0–7° C. for 30 min, excess nitrous acid was destroyed, and then 46 g of an aqueous solution, adjusted to pH 6, of 1-amino-8-hydroxynaphthalene-3,6-disulfonic acid were added dropwise over 1.5 h with very thorough stirring, and the mixture was subsequently stirred overnight, affording the red dye of the formula

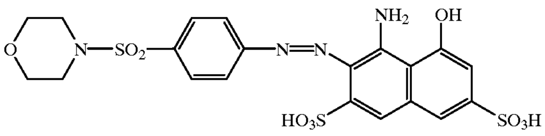

as a thick suspension. The dye gives a red solution in water and has an absorption maximum at 518 nm in the visible spectrum.

b) Then a diazonium salt solution was added, which had been prepared as follows: 17.7 g of the diazo component of the formula

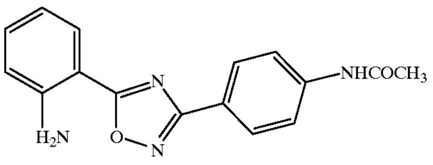

were diazotized with water, dilute hydrochloric acid and sodium nitrite and also a little glacial acetic acid in a conventional manner at from 10 to 20° C. The reaction mixture was neutralized with dilute sodium hydroxide solution, affording the dye of the formula

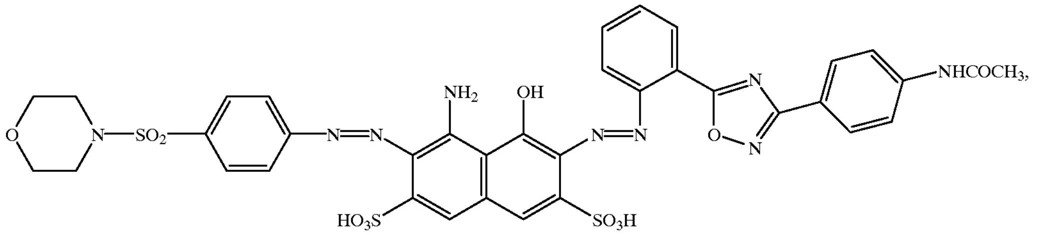
which was precipitated with sodium chloride and then isolated in a conventional manner. The black powder dissolves in water with a reddish blue color ($\lambda_{max}$: 570 nm, shoulder at 625 nm) and dyes wool (acetic- to formic-acid medium) in a deep reddish blue shade having very good lightfastness.
The dyes listed in the table which follows are obtained in a similar manner.

TABLE 23
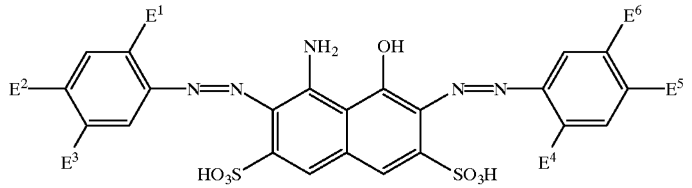
| Ex. No. | $E^1$ | $E^2$ | $E^3$ | $E^4$ | $E^5$ | $E^6$ | Hue on wool |
|---|---|---|---|---|---|---|---|
| 418 | H | $C_6H_5SO_2$ | $SO_3H$ | $CO_2CH_3$ | H | $CO_2CH_2CH_3$ | reddish blue |
| 419 | H | 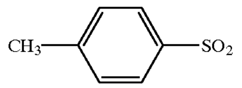 | $SO_3H$ | $CO_2CH_3$ | H | $CO_2CH_2CH_3$ | reddish blue |
| 420 | H | 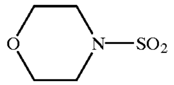 | H | $CO_2CH_3$ | H | $CO_2CH_2CH_3$ | reddish blue |
| 421 | $CH_3$ | 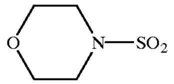 | $CH_3$ | $CO_2CH_3$ | H | $CO_2CH_2CH_3$ | reddish blue |
| 422 | H | 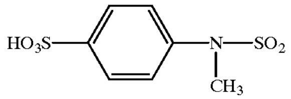 | H | $CO_2CH_3$ | H | $CO_2CH_2CH_3$ | reddish blue |
| 423 | H | 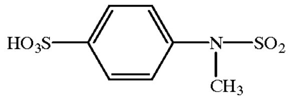 | H | $CO_2C_2H_5$ | H | $CO_2CH_2CH_3$ | reddish blue |
| 424 | H | 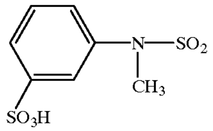 | H | $CO_2CH_3$ | H | $CO_2CH_2CH_3$ | reddish blue |

TABLE 23-continued
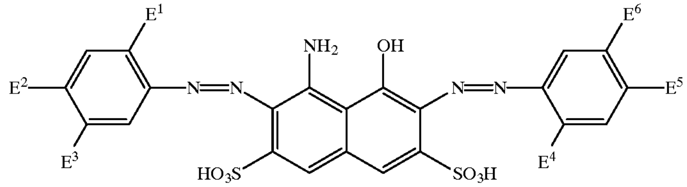
| Ex. No. | $E^1$ | $E^2$ | $E^3$ | $E^4$ | $E^5$ | $E^6$ | Hue on wool |
|---|---|---|---|---|---|---|---|
| 425 | H | 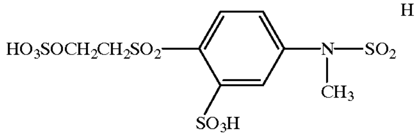 | H | $CO_2CH_3$ | H | $CO_2CH_2CH_3$ | reddish blue |
| 426 | H | 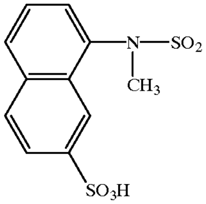 | H | $CO_2CH_3$ | H | $CO_2CH_3$ | blue |
| 427 | H | 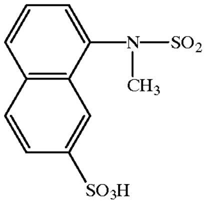 | H | $CO_2C_2H_5$ | H | $CO_2C_2H_5$ | blue |
| 428 | H | $C_6H_5OSO_2$ | H | $CO_2CH_3$ | H | $CO_2CH_3$ | blue |
| 429 | H | $C_6H_5OSO_2$ | H | $CO_2C_3H_7$ | H | $CO_2CH_3$ | blue |
| 430 | H | $C_6H_5OSO_2$ | H | $CO_2CH_3$ | H | $CO_2C_3H_7$ | blue |
| 431 | H | 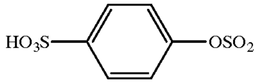 | H | $CO_2CH_3$ | H | $CO_2CH_3$ | blue |

TABLE 23-continued
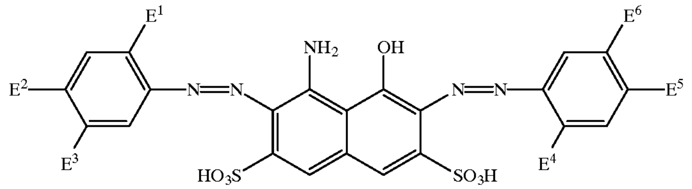
| Ex. No. | $E^1$ | $E^2$ | $E^3$ | $E^4$ | $E^5$ | $E^6$ | Hue on wool |
|---|---|---|---|---|---|---|---|
| 432 | $CH_3$ | 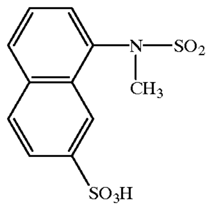 | H | $CO_2CH_3$ | H | $CO_2CH_3$ | blue |
| 433 | H | 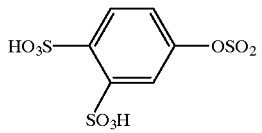 | H | $CO_2CH_3$ | H | $CO_2CH_3$ | reddish blue |
| 434 | $C_6H_5SO_2$ | H | H | $CO_2CH_3$ | H | $CO_2CH_3$ | blue |
| 435 | $C_6H_5SO_2$ | $SO_3H$ | H | $CO_2CH_3$ | H | $CO_2CH_3$ | blue |
| 436 | $C_6H_5SO_2$ | H | $SO_3H$ | $CO_2CH_3$ | H | $CO_2CH_3$ | dark blue |
| 437 | $C_6H_5SO_2$ | $SO_3H$ | H | $CO_2C_2H_5$ | H | $CO_2C_2H_5$ | dark blue |
| 438 | 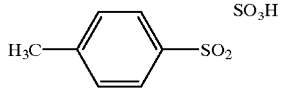 | $SO_3H$ | H | $CO_2CH_3$ | H | $CO_2CH_3$ | dark blue |
| 439 | 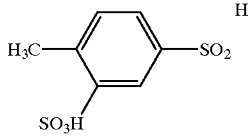 | H | H | $CO_2C_2H_5$ | H | $CO_2C_2H_5$ | dark blue |

TABLE 23-continued
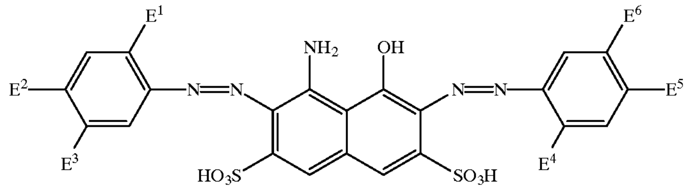
| Ex. No. | E¹ | E² | E³ | E⁴ | E⁵ | E⁶ | Hue on wool |
|---|---|---|---|---|---|---|---|
| 440 | 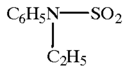 | H | H | $CO_2CH_3$ | H | $CO_2CH_3$ | dark blue |
| 441 | $C_6H_5CO$ | Cl | H | $CO_2CH_3$ | H | $CO_2CH_3$ | blue |
| 442 | $CO_2CH_3$ | H | $CO_2CH_3$ | 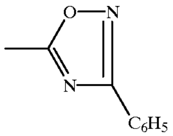 | $SO_3H$ | H | reddish blue |
| 443 | $CO_2CH_3$ | H | $CO_2CH_3$ | 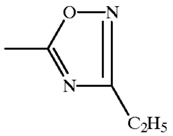 | H | H | reddish blue |
| 444 | $CO_3CH_3$ | H | $CO_2CH_3$ | 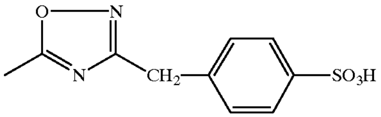 | H | H | reddish blue |
| 445 | H | 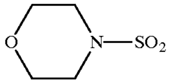 | H | 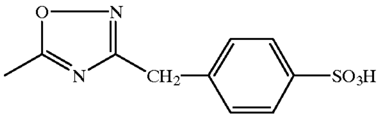 | H | H | reddish blue |

TABLE 23-continued
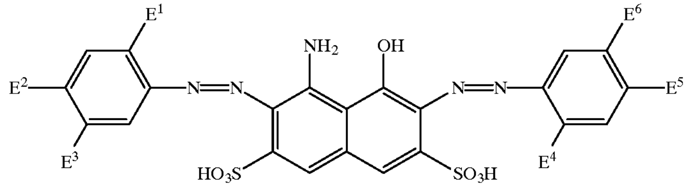
| Ex. No. | $E^1$ | $E^2$ | $E^3$ | $E^4$ | $E^5$ | $E^6$ | Hue on wool |
|---|---|---|---|---|---|---|---|
| 446 | H | $(CH_3)_2N—SO_2$ | H | 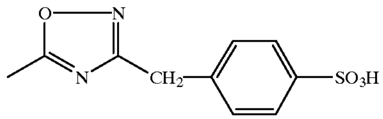 | H | H | reddish blue |
| 447 | H | 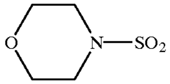 | H | 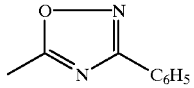 | $SO_3H$ | H | navy |
| 448 | $CH_3$ | 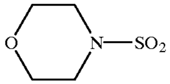 | H | 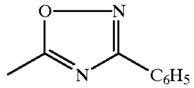 | $SO_3H$ | H | navy |
| 449 | H | $(C_2H_5)_2N—SO_2$ | H | 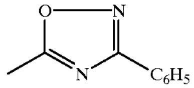 | H | $SO_3H$ | navy |
| 450 | H | 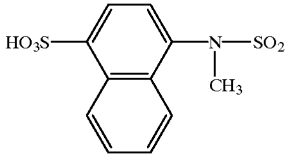 | H | 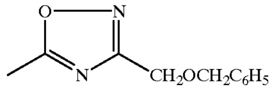 | H | H | blue |
| 451 | H | 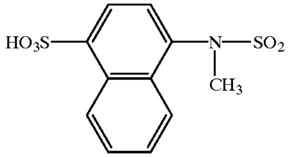 | H | 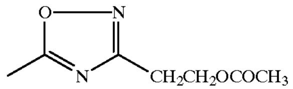 | H | H | reddish blue |

TABLE 23-continued
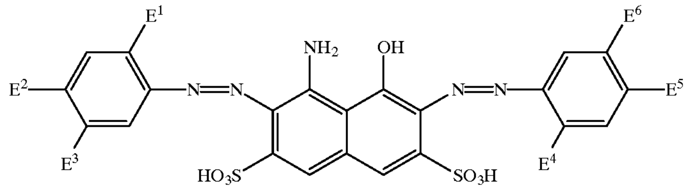
| Ex. No. | $E^1$ | $E^2$ | $E^3$ | $E^4$ | $E^5$ | $E^6$ | Hue on wool |
|---|---|---|---|---|---|---|---|
| 452 | H | $C_6H_5OSO_2$ | H | 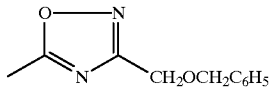 | H | H | reddish blue |
| 453 | H | $CH_2{=}CHSO_2$ | H | 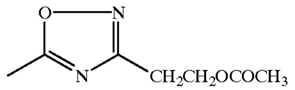 | H | H | navy |
| 454 | H | $CH_2{=}CHSO_2$ | H | 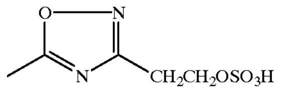 | H | H | navy |
| 455 | H | $CH_2{=}CHCH_2SO_2$ | H | 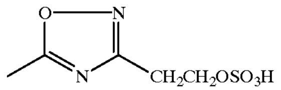 | H | H | navy |
| 456 | H | $CH_2{=}CHSO_2$ | H | 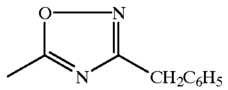 | H | H | navy |
| 457 | H | $CH_2{=}CHSO_2$ | H | 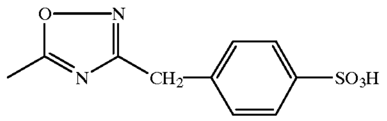 | H | H | navy |

TABLE 23-continued
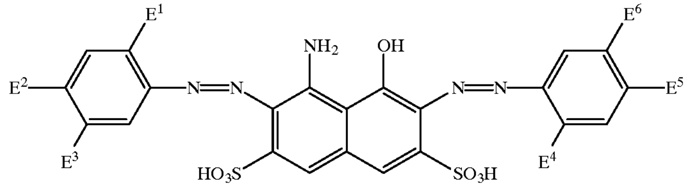
| Ex. No. | E¹ | E² | E³ | E⁴ | E⁵ | E⁶ | Hue on wool |
|---|---|---|---|---|---|---|---|
| 458 | H | $C_6H_5SO_2$ | H | 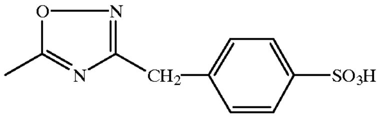 | H | H | reddish blue |
| 459 | H | $C_6H_5SO_2$ | H | 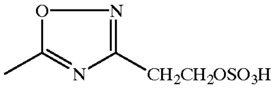 | H | H | reddish blue |
| 460 | H | $C_6H_5SO_2$ | $SO_3H$ | 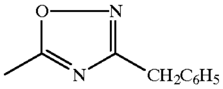 | H | H | reddish blue |
| 461 | H | 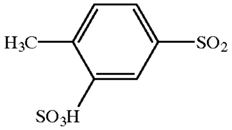 | H | 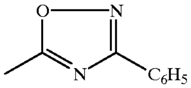 | H | H | reddish blue |
| 462 | 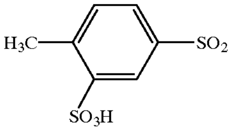 | H | H | 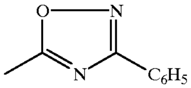 | H | H | reddish blue |

TABLE 23-continued
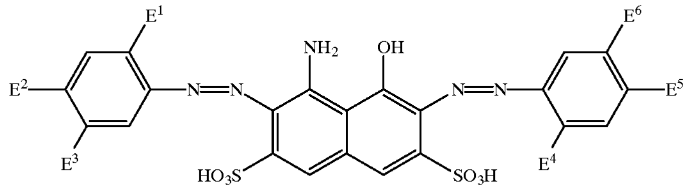
| Ex. No. | $E^1$ | $E^2$ | $E^3$ | $E^4$ | $E^5$ | $E^6$ | Hue on wool |
|---|---|---|---|---|---|---|---|
| 463 | 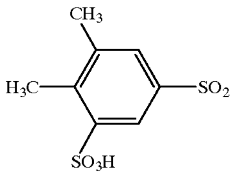 | H | H | 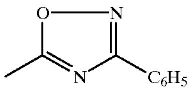 | H | H | reddish blue |
| 464 | $CH_3$ | $HO_3SOCH_2CH_2SO_2$ | $CH_3$ | 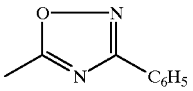 | H | H | navy |
| 465 | H | $CH_3O_2C$ | H | 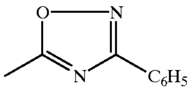 | $SO_3H$ | H | reddish blue |
| 466 | H | 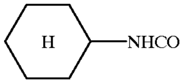 | H | 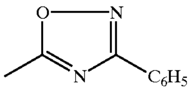 | $SO_3H$ | H | reddish blue |
| 467 | $SO_3H$ | $(C_2H_5)_2NSO_2$ | H | 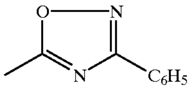 | H | H | reddish blue |
| 468 | $SO_3H$ | 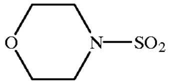 | H | 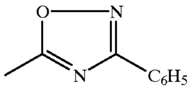 | H | H | reddish blue |

EXAMPLE 469

225 g of 1-aminonaphthalene-3-sulfonic acid were dissolved in 800 ml of water at pH 7 (sodium hydroxide solution) and 50° C. 258 g of 4-acetaminobenzenesulfonyl chloride were then added a little at a time with very thorough stirring while the pH of the mixture was maintained within the range from 6.0 to 7.2 by the simultaneous addition of 60 g of sodium carbonate. The mixture was subsequently stirred at pH 7 for 1 hour, then adjusted to pH 9 with sodium hydroxide solution and admixed with 160 g of dimethyl sulfate added dropwise over 15 min while the reaction pH was maintained at >8 to 9 using sodium hydroxide solution. The resulting suspension was subsequently stirred at 45–50° C. for 2 h, then 100 ml of 25% strength by weight aqueous ammonia solution were added, and the dye was precipitated with 250 g of sodium chloride and filtered off with suction. The filter residue was taken up with 300 ml of methanol and 500 ml of water, the mixture was admixed with 135 g of concentrated sulfuric acid and stirred for 6 h under evaporative cooling. Methanol was then distilled off with a little water, the suspension was stirred overnight until cold, the precipitate was isolated on a suction filter, washed with a little ice-cold, highly dilute hydrochloric acid and dried to leave 350 g of the diazo component of the formula

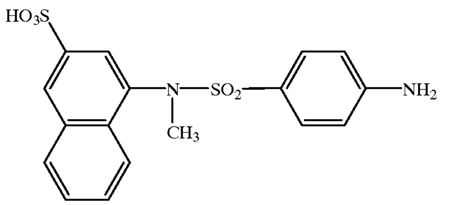

The H—NMR spectrum recorded in hexadeuterodimethyl sulfoxide showed the —N—$CH_3$ signal at 3.18 ppm (singlet of the $CH_3$ protons).

EXAMPLE 470

225 g of 1-aminonaphthalene-3-sulfonic acid were reacted with 258 g of 4-acetaminosulfonyl chloride similarly to Example 469 and alkylated with dimethyl sulfate, and then excess dimethyl sulfate was destroyed with ammonia. Sodium hydroxide solution was then used to render the reaction mixture strongly alkaline (pH >12 to about 13), and the mixture was stirred at 80 to 100° C. for 5 h while the pH was held at >12. Thereafter it was slowly acidified with hydrochloric acid to a pH of about 1 to 1.5 and cooled down to room temperature. After stirring overnight the resulting suspension was filtered off with suction and washed once with very dilute hydrochloric acid, affording the diazo component of the formula

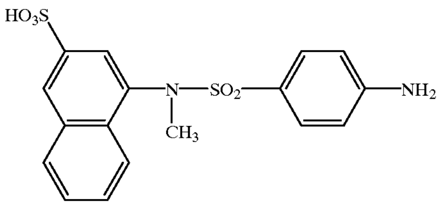

in similar yield and comparable purity.

The following compounds are obtained in a similar manner:

| Ex. No. | | E |
|---|---|---|
| 471<br>472 | 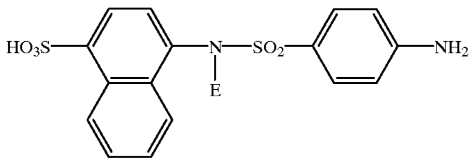 | $CH_3$ (S., 3.14 ppm) and<br>$C_2H_5$ |
| 473<br>474 | 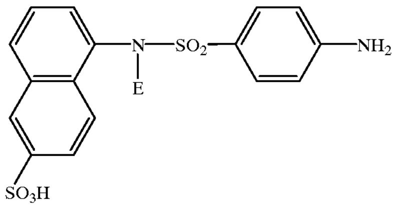 | $CH_3$ (S., 3.18 ppm)<br>$C_2H_5$ |

-continued

| Ex. No. | | E |
|---|---|---|
| 475<br>476 | 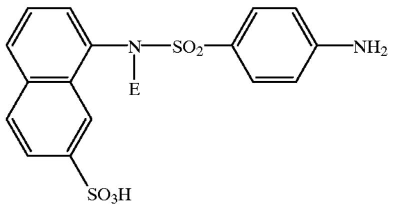 | $CH_3$ (S., 3.06 ppm)<br>$C_2H_5$ |
| 477<br>478 | 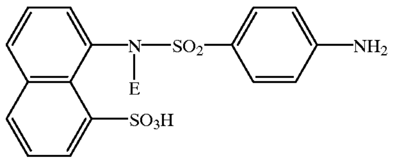 | $CH_3$<br>$C_2H_5$ |
| 479 | 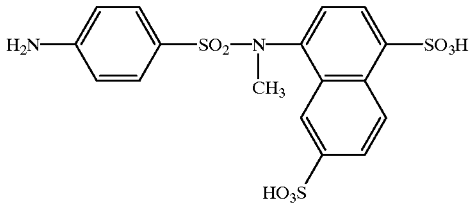 | singlet at 3.05 ppm |

EXAMPLE 480

250 g of N-ethylaminobenzene-4-sulfonic acid were stirred together with 800 ml of water and adjusted to pH 7 at 50–55° C. using sodium hydroxide solution. Then 306 g of 4-acetaminobenzenesulfonyl chloride were added a little at a time with vigorous stirring while the reaction mixture pH was maintained within the range from 6 to 7.5 using sodium carbonate. The mixture was subsequently stirred for 1 h, then adjusted to pH 12.5–14 and subsequently stirred under evaporative cooling at a pH >12.5 to 13 for 7 h during which further sodium hydroxide solution was added. The mixture was then acidified with hydrochloric acid at pH 1 and 70° C., cooled down to room temperature and allowed to crystallize overnight. The precipitated product was filtered off with suction and washed with cold dilute hydrochloric acid. Drying left 400 g of the diazo component of the formula

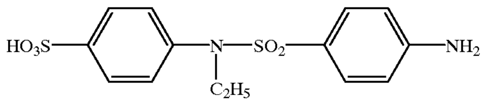

The H—NMR spectrum of the product shows the protons of the $C_2H_5$ group as a quartet at 3.51 ppm (quartet of the —$CH_2$— group) 0.9 ppm (triplet of the —$CH_3$— group) recorded in dimethyl sulfoxide.

Favorable results are also obtained with the following dyes:

| Dye No. | | |
|---|---|---|
| F1 | 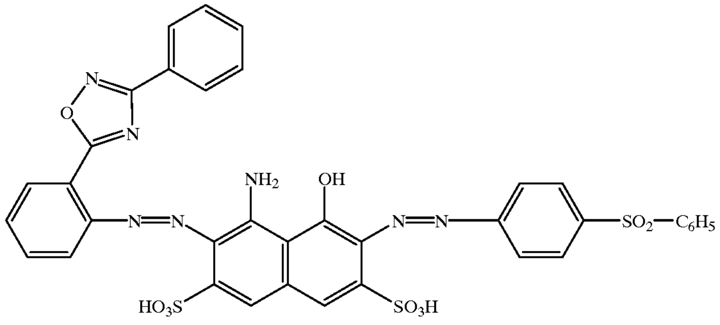 | navy<br>$\lambda_{max}$:<br>587 nm |

-continued
| Dye No. | | |
|---|---|---|
| F2 | 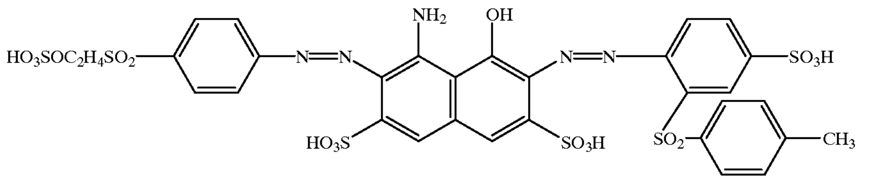 | $\lambda_{max}$: 598 nm |
| F3 | 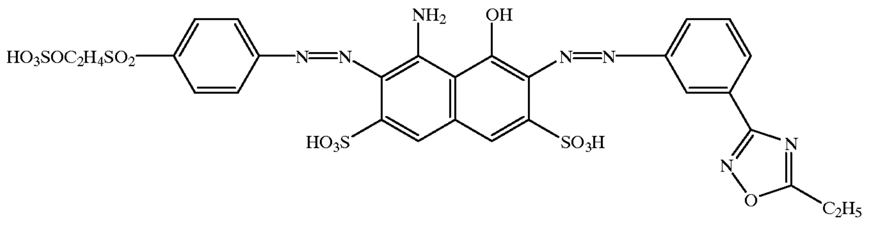 | navy $\lambda_{max}$: 600 nm |
| F4 | 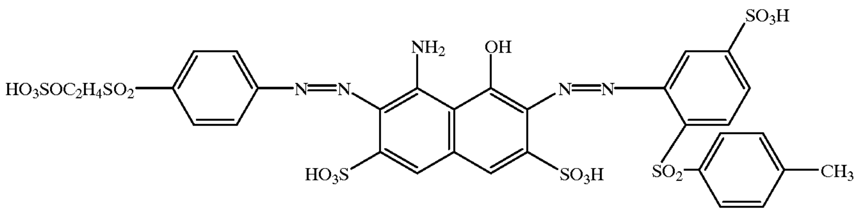 | $\lambda_{max}$: 596.5 nm |
| F5 | 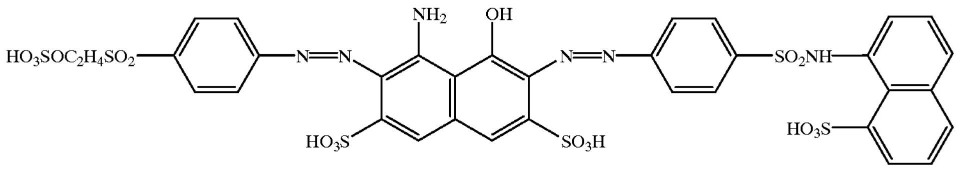 | greenish blue |
| F6 | 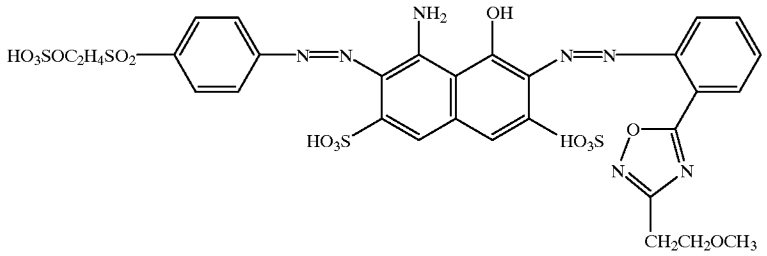 | $\lambda_{max}$: 584 nm |
| F7 | 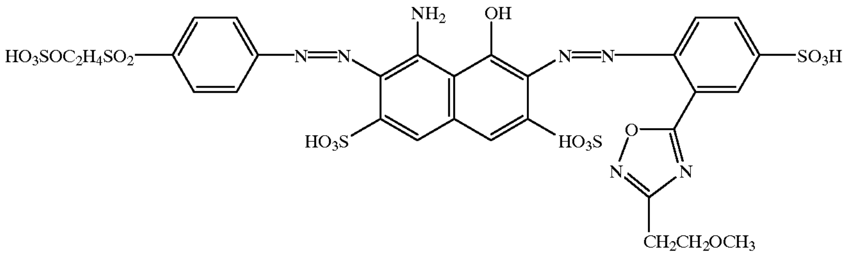 | $\lambda_{max}$: 587 nm shoulder: 620 nm |

-continued
| Dye No. | | |
|---|---|---|
| F8 | 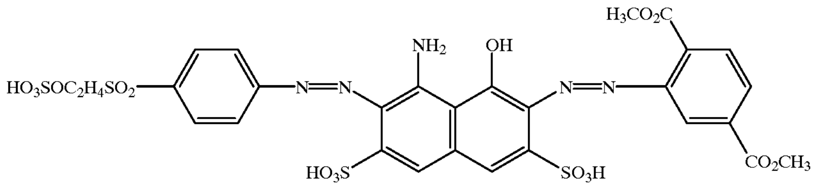 | $\lambda_{max}$: 584 nm shoulder: ~615 nm |
| F9 | 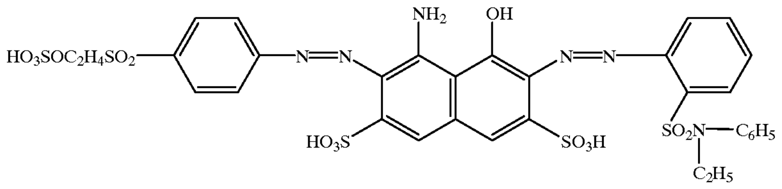 | navy $\lambda_{max}$: 600 nm |
| F10 | 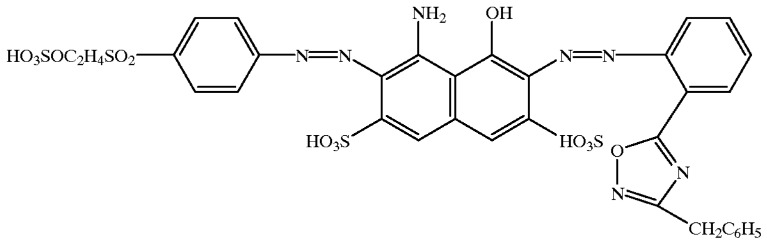 | $\lambda_{max}$: 584 nm |
| F11 | 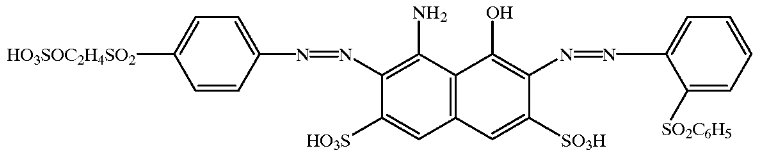 | $\lambda_{max}$: 596 nm |
| F12 | 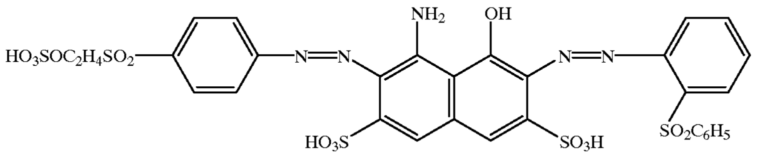 | $\lambda_{max}$: 598 nm |
| F13 | 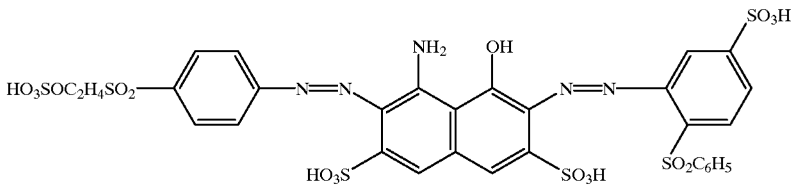 | $\lambda_{max}$: 597 nm |
| F14 | 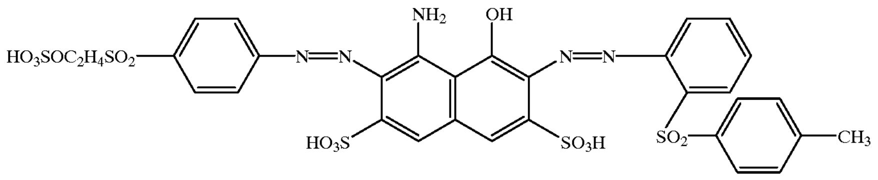 | $\lambda_{max}$: 594 nm |

-continued
| Dye No. | | |
|---|---|---|
| F15 | 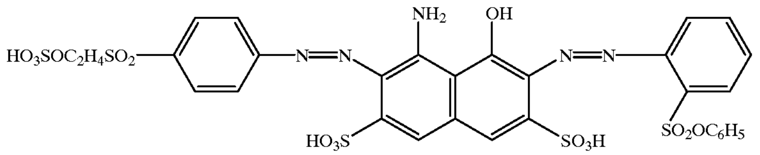 | navy |
| F16 | 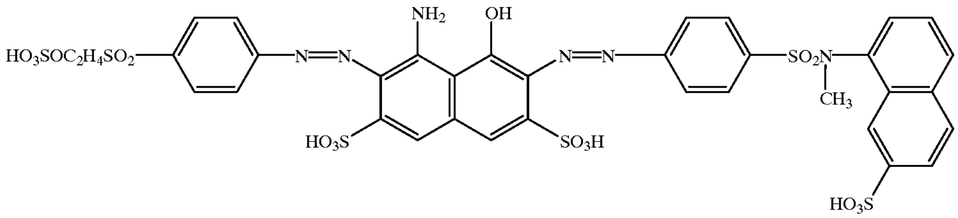 | bluish black |
| F17 | 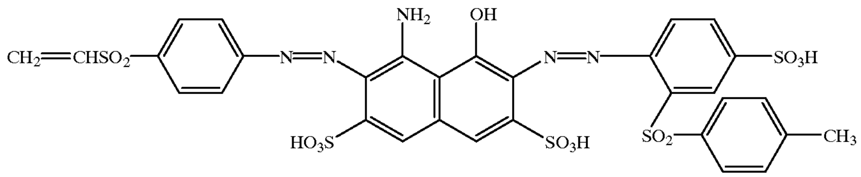 | $\lambda_{max}$: 596 nm |
| F18 | 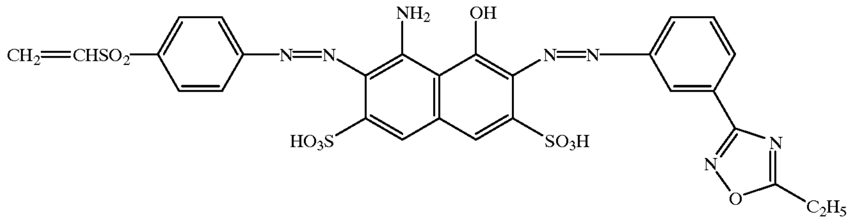 | navy $\lambda_{max}$: 598 nm |
| F19 | 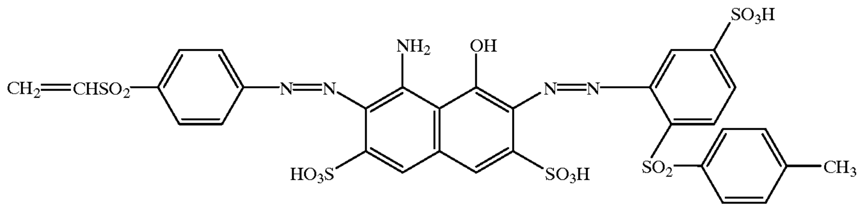 | $\lambda_{max}$: 597 nm |
| F20 | 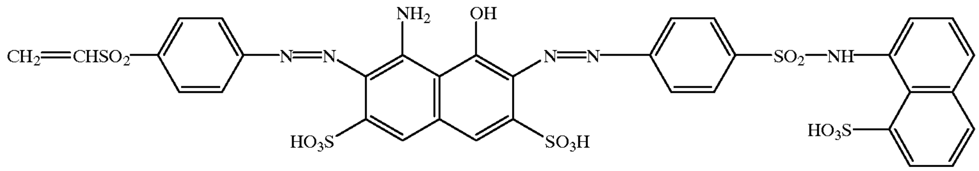 | navy |
| F21 | 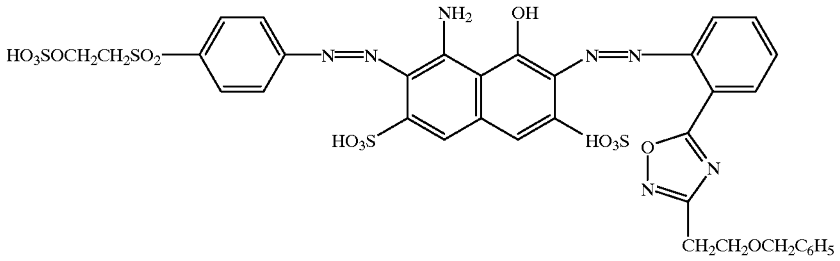 | $\lambda_{max}$: 581 nm shoulder ~618 nm |

-continued
| Dye No. | | |
|---|---|---|
| F22 | 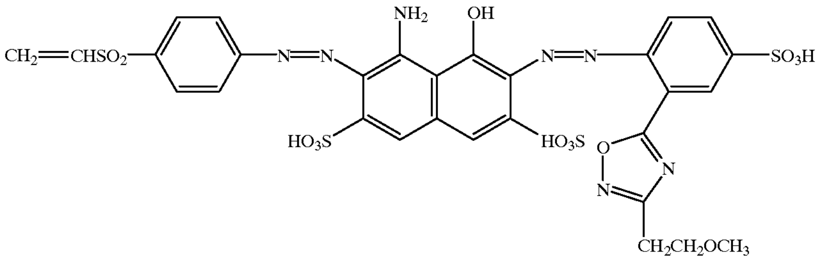 | $\lambda_{max}$: 583 nm shoulder at 620 nm |
| F23 | 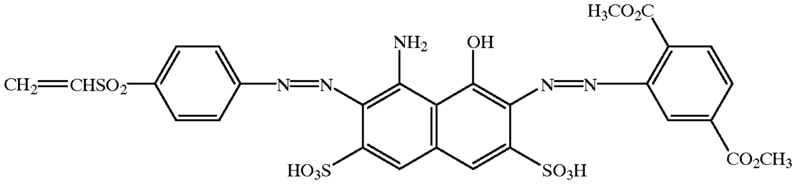 | $\lambda_{max}$: 582 nm shoulder 625 nm |
| F24 | 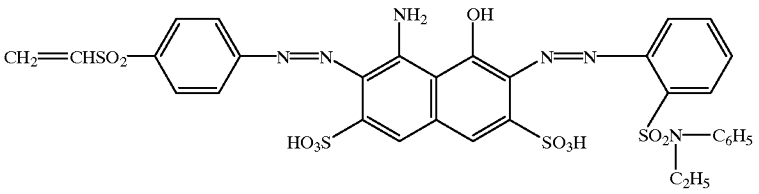 | $\lambda_{max}$: 599 nm |
| F25 | 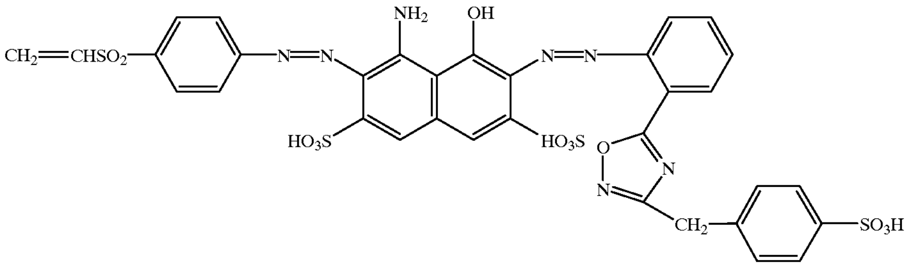 | $\lambda_{max}$: 582 nm |
| F26 | 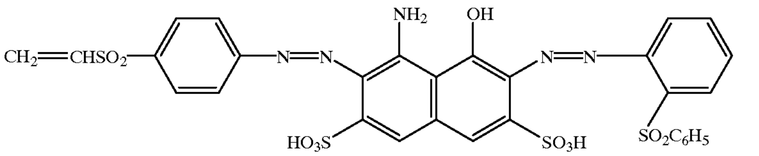 | $\lambda_{max}$: 594 nm |
| F27 | 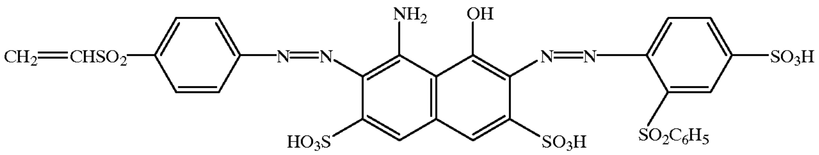 | $\lambda_{max}$: 597 nm |
| F28 | 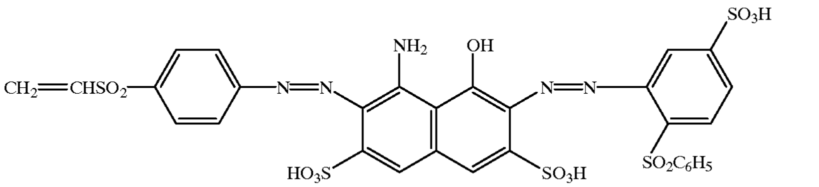 | $\lambda_{max}$: 595 nm |

-continued
| Dye No. | | |
|---|---|---|
| F29 | 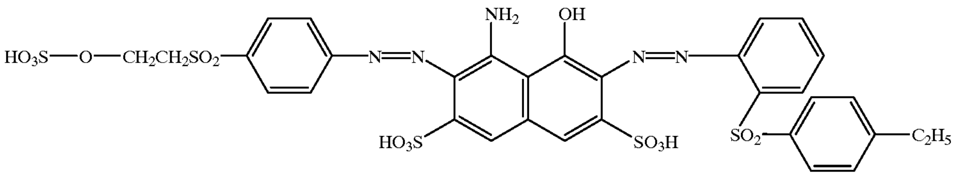 | $\lambda_{max}$: 594 nm |
| F30 | 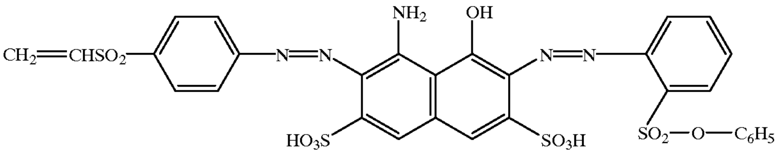 | navy |
| F31 | 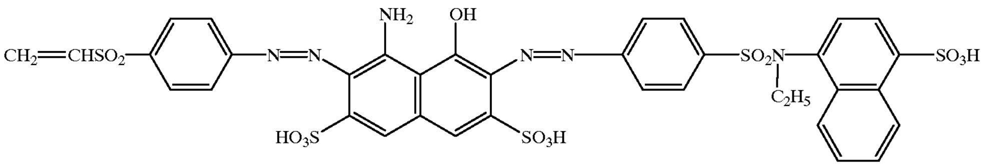 | dark blue |
| F32 | 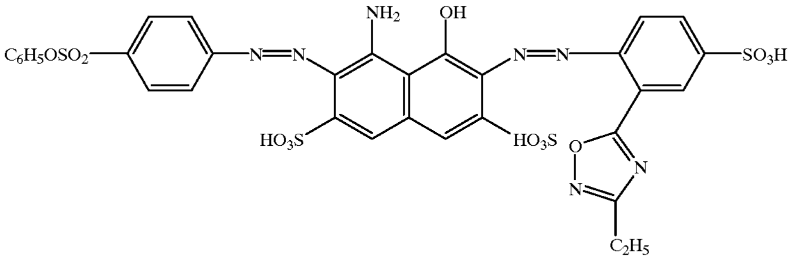 | navy $\lambda_{max}$: 580 nm |
| F33 | 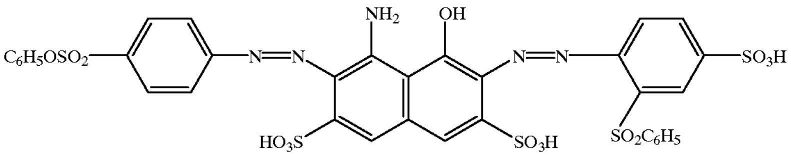 | dark blue $\lambda_{max}$: 579 nm 401 nm shoulder 622 nm |
| F34 | 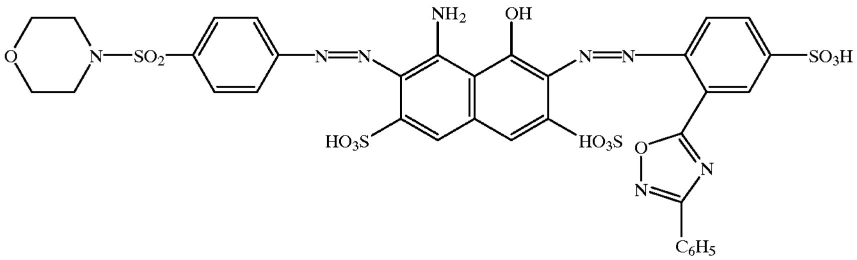 | $\lambda_{max}$: 572 nm shoulder ~625 nm reddish blue |
| F35 | 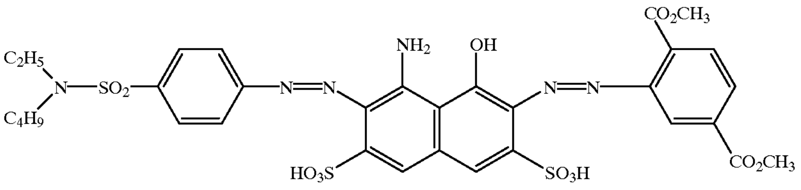 | $\lambda_{max}$: 395 nm 582 nm shoulder 623 nm |

-continued
| Dye No. | | |
|---|---|---|
| F36 | 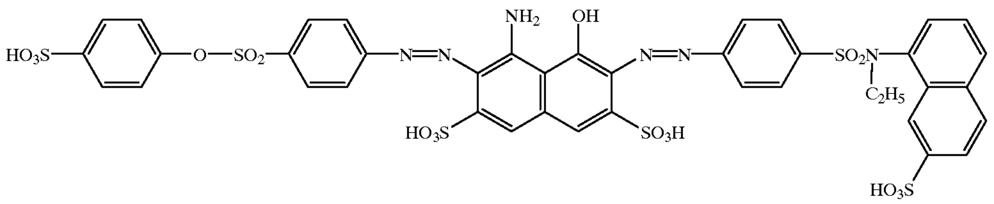 | bluish black |
| F37 | 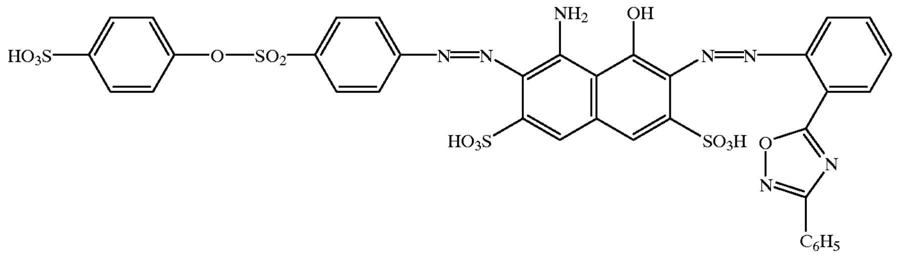 | $\lambda_{max}$: 402 nm 574 nm navy shoulder ~625 nm |
| F38 | 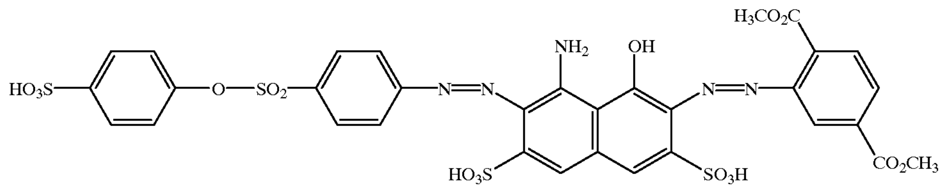 | navy |
| F39 | 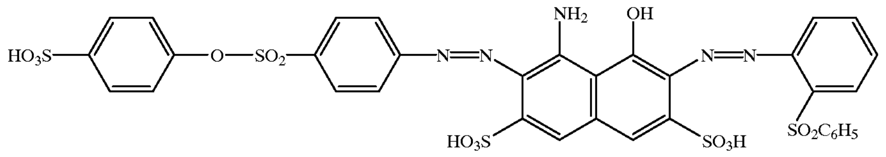 | navy |
| F40 | 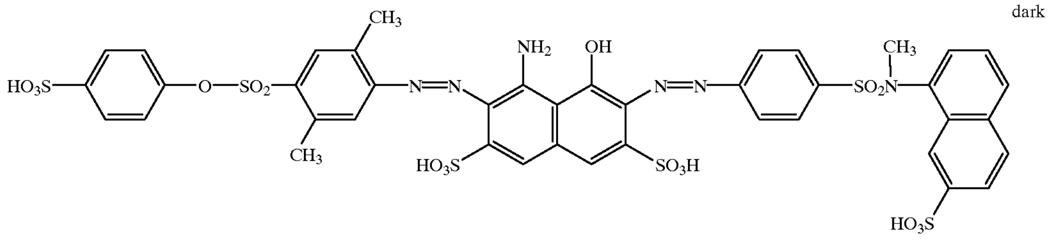 | dark blue |
| F41 | 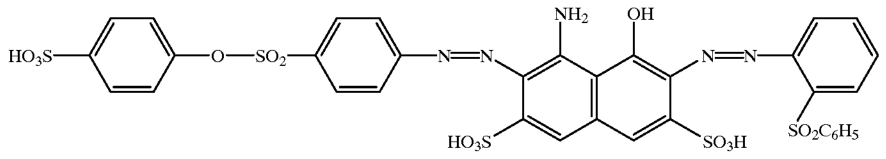 | dark blue |
| F42 | 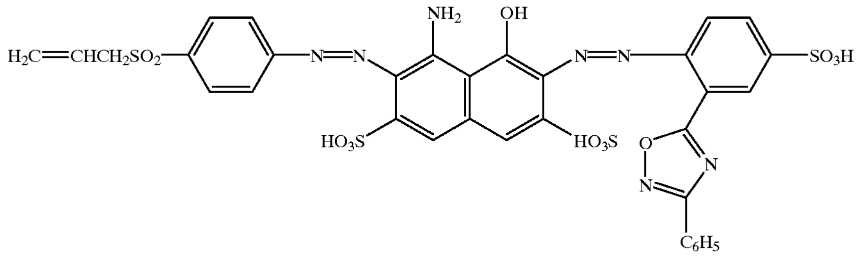 | reddish blue |

-continued
| Dye No. | | |
|---|---|---|
| F43 | 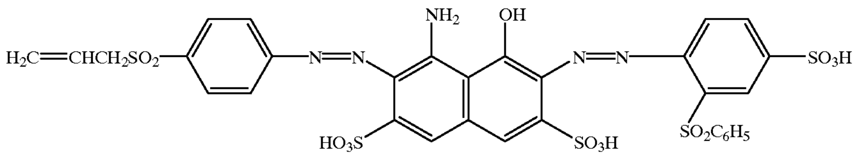 | reddish blue |
| F44 | 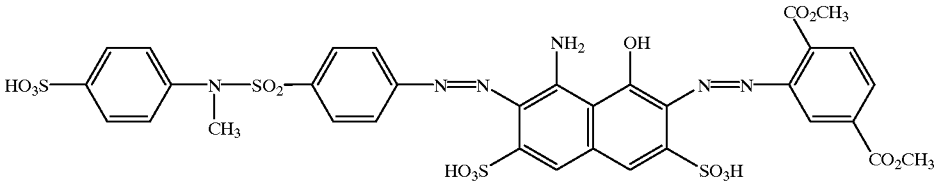 | navy |
| F45 | 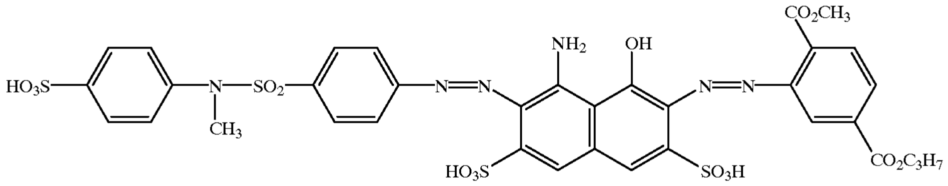 | navy |
| F46 | 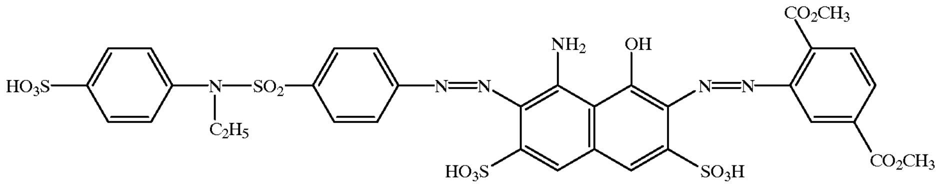 | navy |
| F47 | 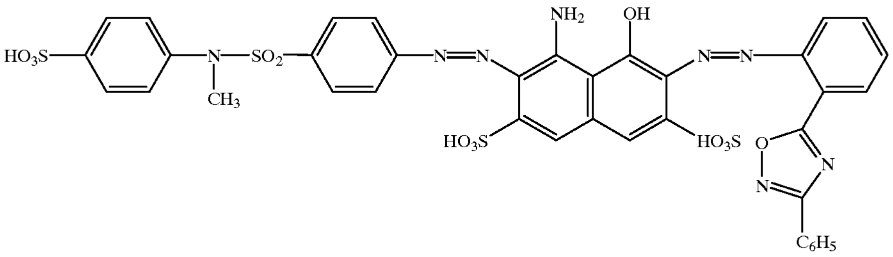 | $\lambda_{max}$: 576 nm shoulder 615 nm |
| F48 | 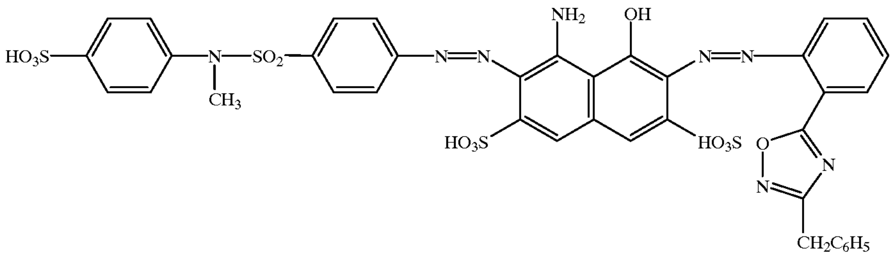 | $\lambda_{max}$: 585 nm shoulder ~620 nm |

-continued
| Dye No. | | |
|---|---|---|
| F49 | 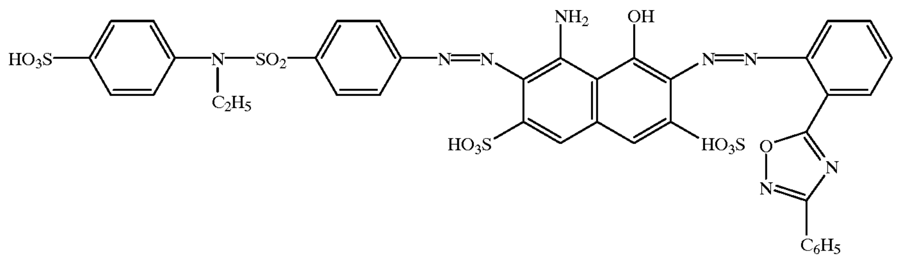 | $\lambda_{max}$: 576 nm shoulder ~615 nm |
| F50 | 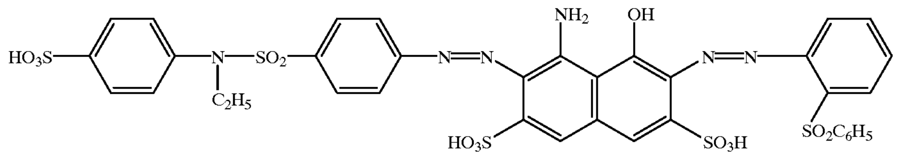 | $\lambda_{max}$: 594 nm |
| F51 | 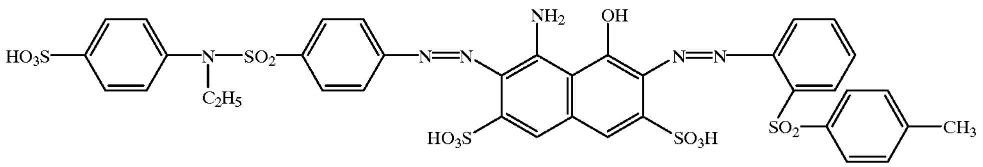 | $\lambda_{max}$: 594 nm |
| F52 | 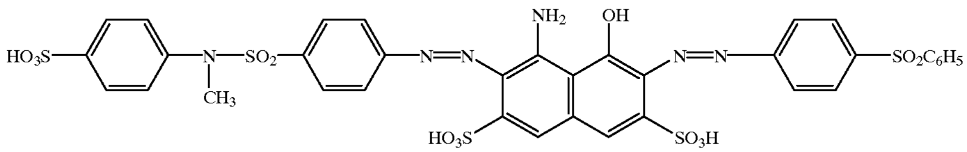 | $\lambda_{max}$: 599 nm |
| F53 | 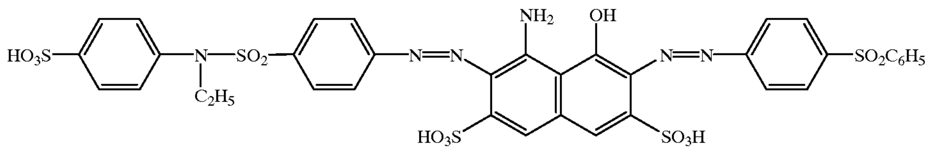 | $\lambda_{max}$: 599 nm |
| F54 | 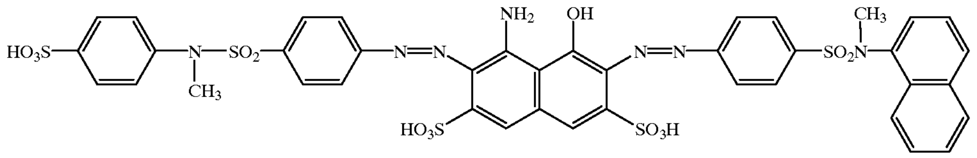 | dark blue |
| F55 | 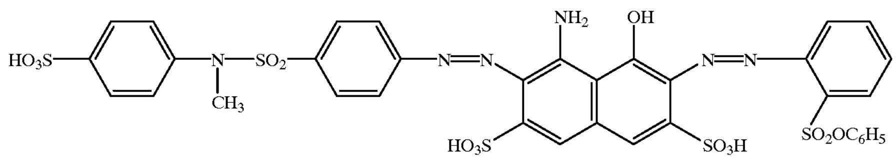 | navy |
| F56 | 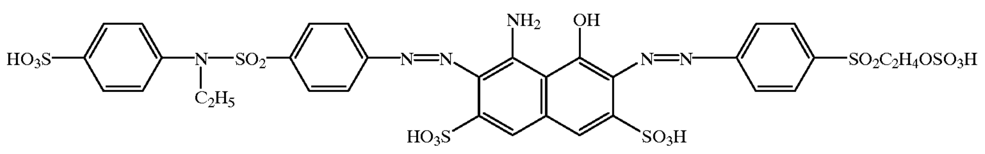 | navy |

-continued
| Dye No. | | |
|---|---|---|
| F57 | 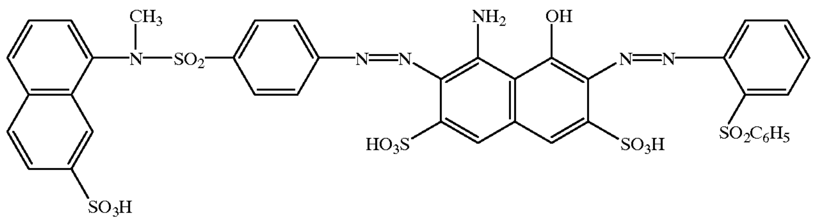 | $\lambda_{max}$: 596 nm |
| F58 | 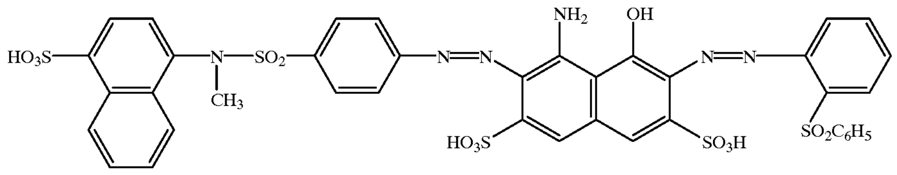 | $\lambda_{max}$: 597 nm |
| F59 | 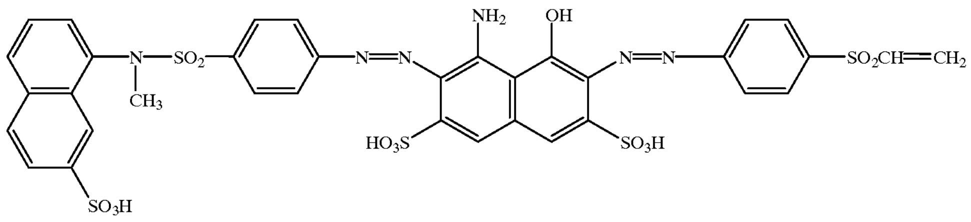 | $\lambda_{max}$: 600 nm |
| F60 | 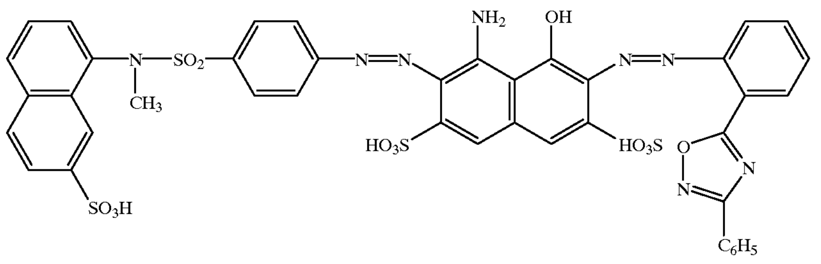 | $\lambda_{max}$: 574 nm shoulder ~615 nm |
| F61 | 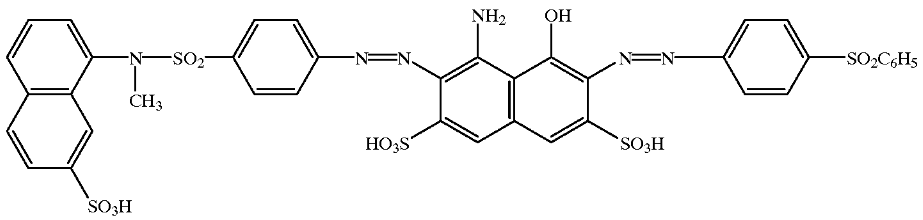 | $\lambda_{max}$: 598 nm |
| F62 | 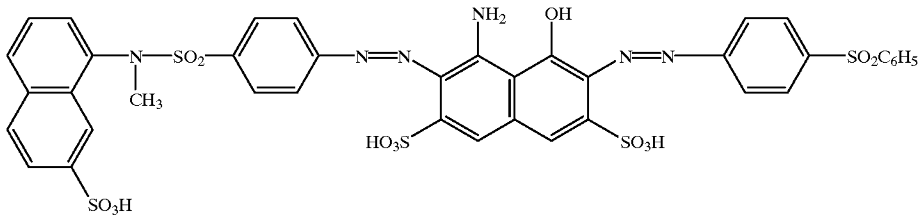 | $\lambda_{max}$: 598 nm |

-continued
| Dye No. | | |
|---|---|---|
| F63 | 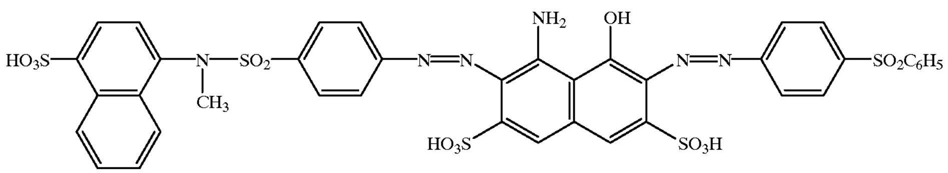 | $\lambda_{max}$: 598 nm |
| F64 | 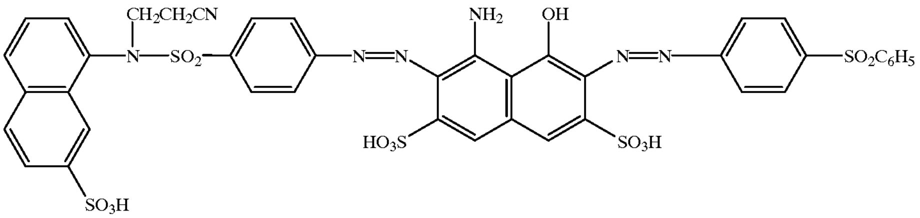 | $\lambda_{max}$: 598 nm |
| F65 | 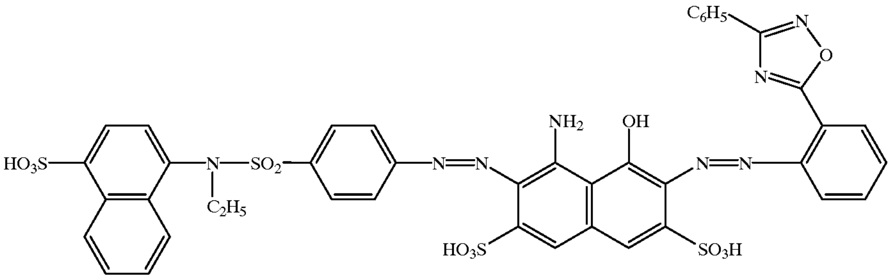 | $\lambda_{max}$: 575 nm navy |
| F66 | 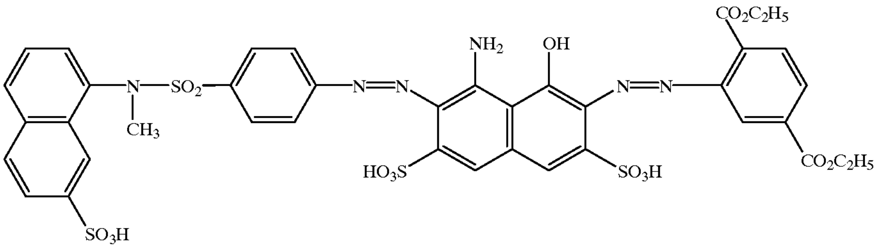 | $\lambda_{max}$: 584 nm shoulder 620 nm |
| F67 | 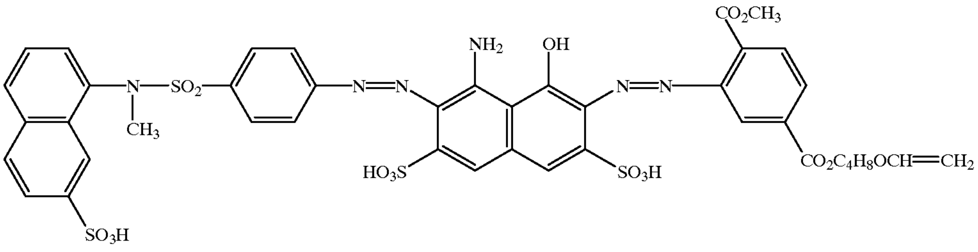 | $\lambda_{max}$: 583 nm shoulder 625 nm |
| F68 | 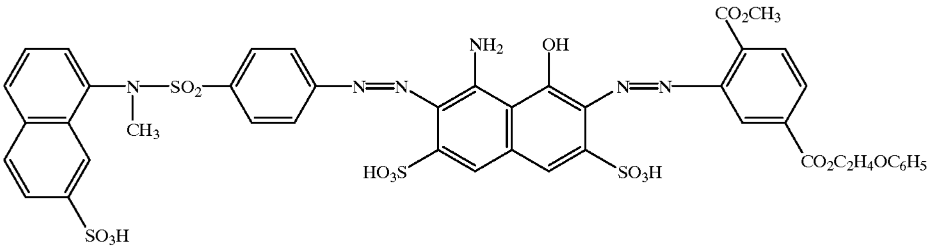 | $\lambda_{max}$: 583 nm shoulder 625 nm |

-continued
| Dye No. | | |
|---|---|---|
| F69 | 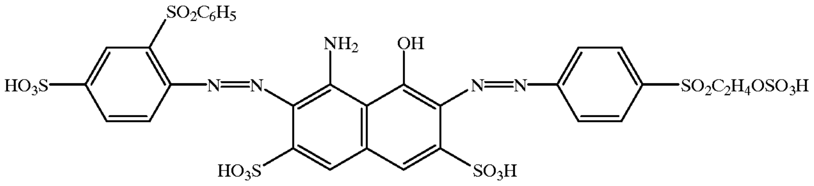 | $\lambda_{max}$: 615 nm |
| F70 | 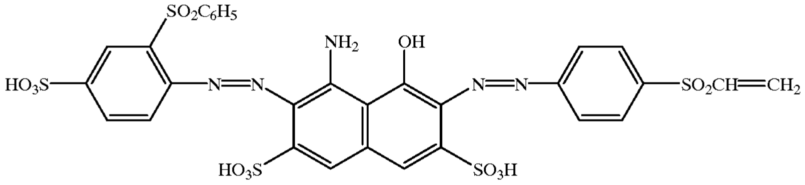 | $\lambda_{max}$: 615 nm |
| F71 | 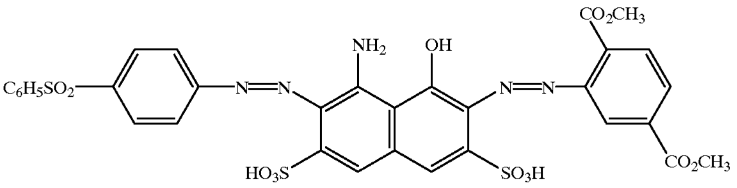 | $\lambda_{max}$: 584 nm shoulder ~625 nm |
| F72 | 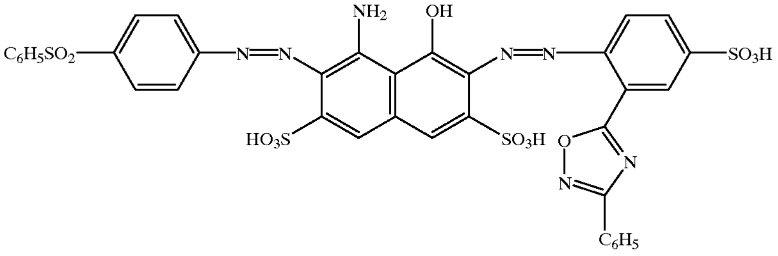 | reddish blue |
| F73 | 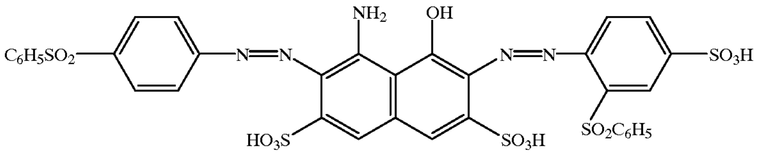 | dark blue |
| F74 | 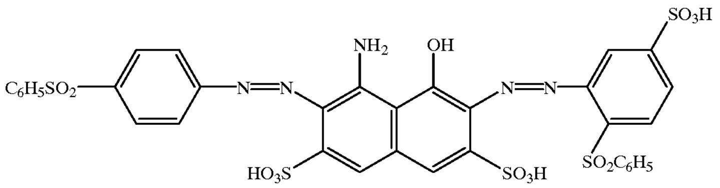 | dark blue |
| F75 | 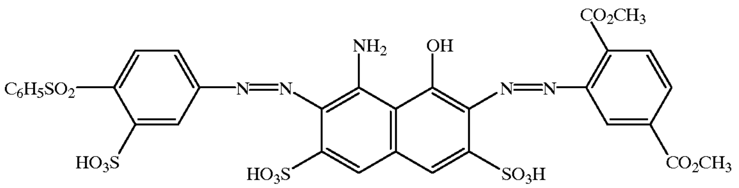 | navy |

-continued
| Dye No. | | |
|---|---|---|
| F76 | 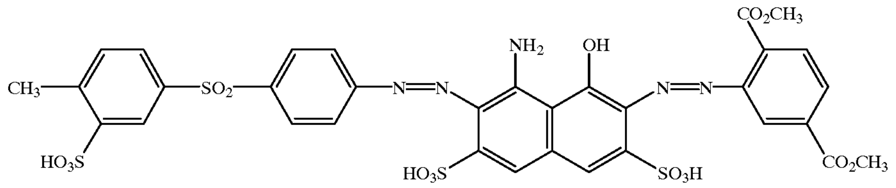 | navy |
| F77 | 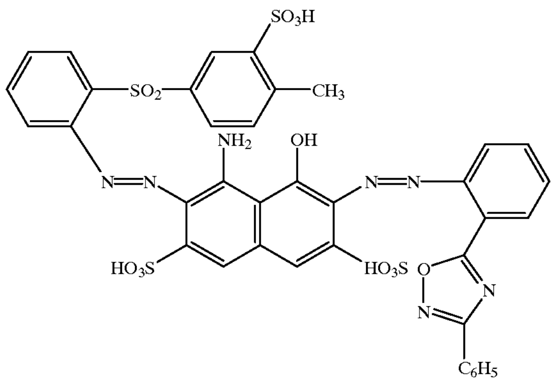 | navy |
| F78 | 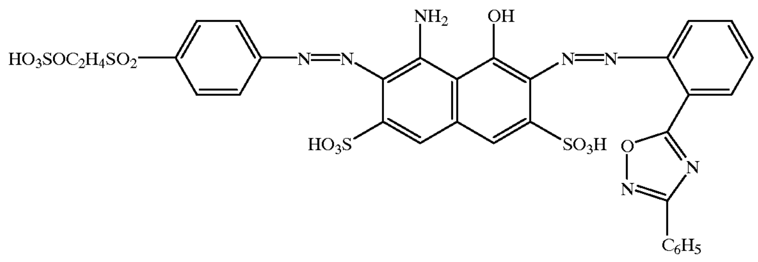 | $\lambda_{max}$: 575 nm (400 nm) shoulder 620 nm navy |
| F79 | 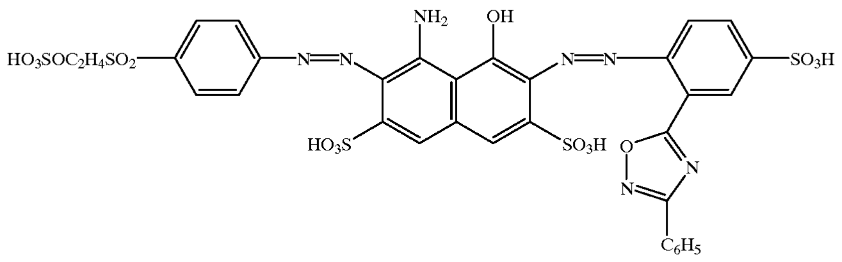 | $\lambda_{max}$: 581 nm (397 nm) shoulder 620 nm |
| F80 | 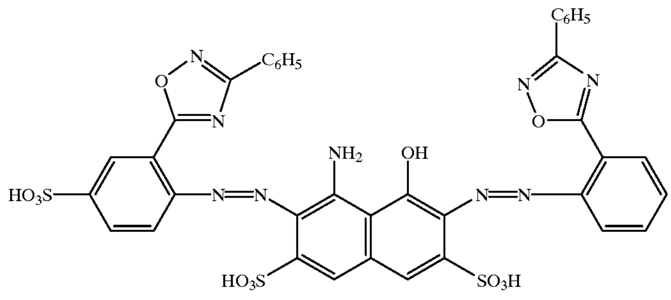 | $\lambda_{max}$: 591 nm (405 nm) shoulder 638 nm |

-continued
| Dye No. | | |
|---|---|---|
| F81 | 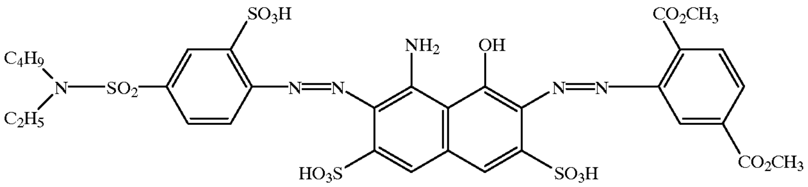 | navy |
| F82 | 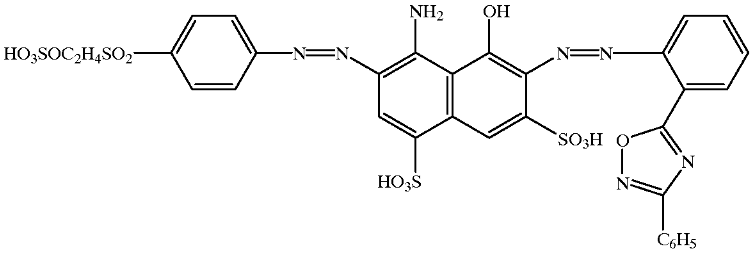 | reddish navy $\lambda_{max}$: 560 nm (405 nm) shoulder: about 605 nm |
| F83 | 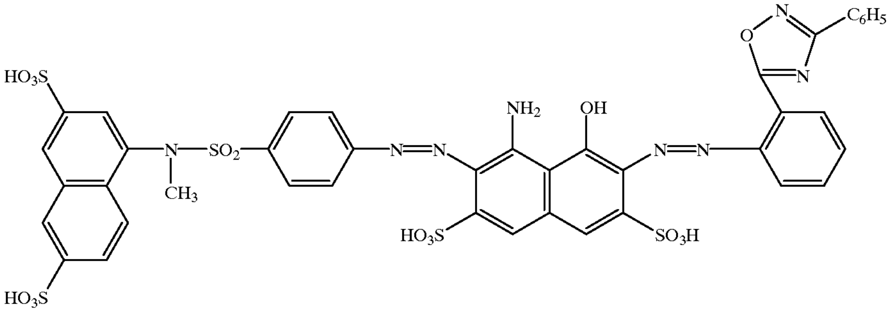 | navy |
| F84 | 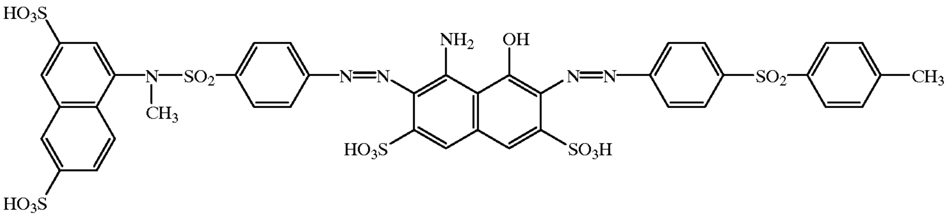 | navy |
| F85 | 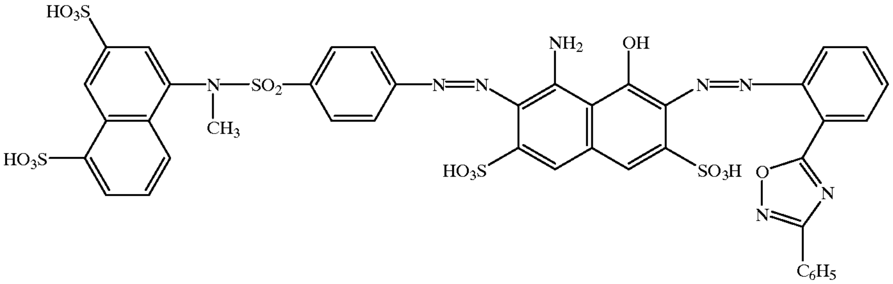 | navy |

-continued
| Dye No. | | |
|---|---|---|
| F86 | 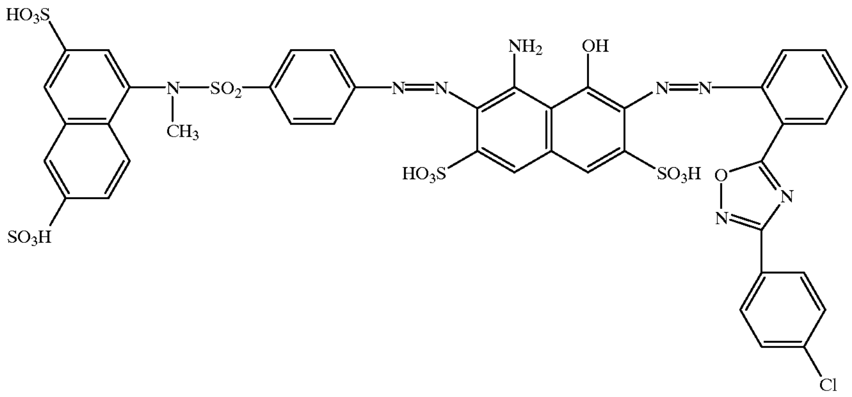 | navy |
| F87 | 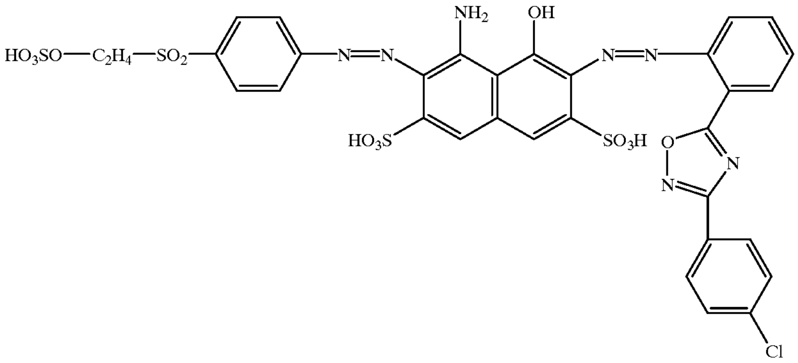 | navy |
| F88 | 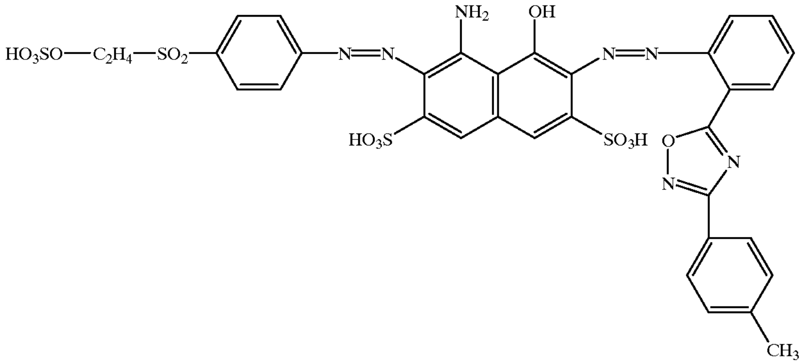 | navy |
| F89 | 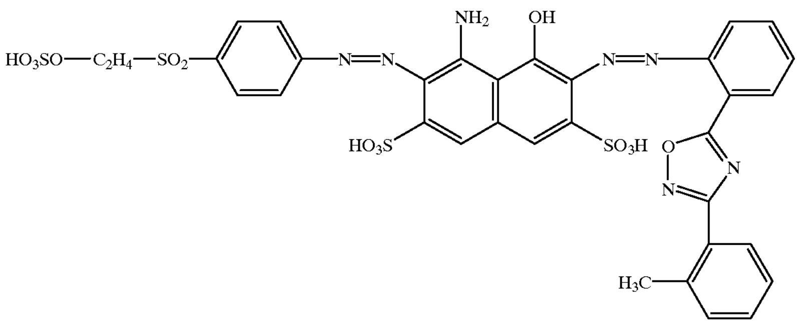 | navy |

-continued

| Dye No. | | |
|---|---|---|
| F90 | 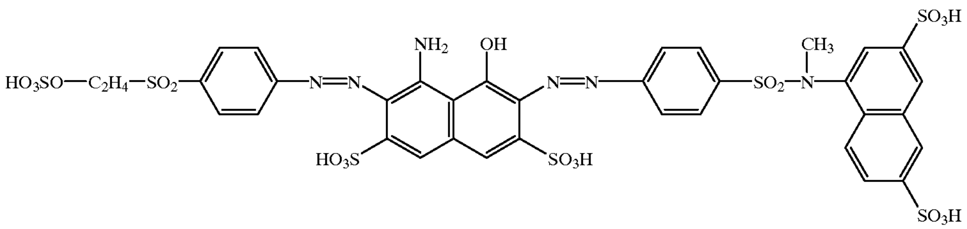 | navy |

What is claimed is:

1. A Disazo dye of the formula III (III)

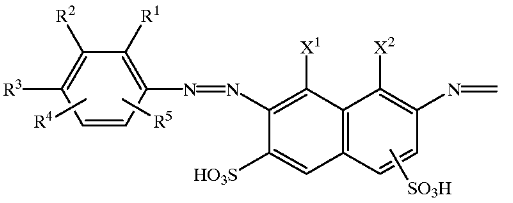

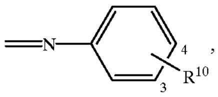
, where one of the two radicals $X^1$ and $X^2$ is hydroxyl and the other is amino, $R^{1'}$ is a radical of the formula CO—OAlk, CO—OAr, $SO_2$—Ar, $SO_2$—OAr,

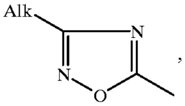
,
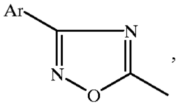
,
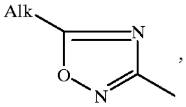
,
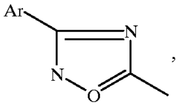
,
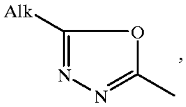
,
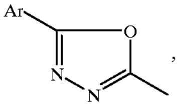
,
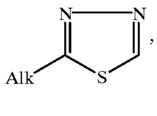
,
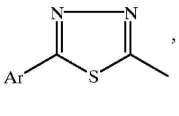
, $R^2$ is hydrogen or $R^2$ and $R^{1'}$ together are a radical of the formula

O—NZ'—CO or

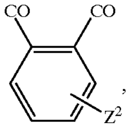
, $R^3$ is hydrogen, hydroxysulfonyl, $C_1$–$C_4$-alkyl, halogen or a radical of the formula $SO_2$—OAr, $SO_2$—N(Ar)Alk or $SO_2$—NHAr or $R^3$ and $R^2$ together are a radical of the formula CO—$NZ^1$—Y, $R^4$ is hydrogen, hydroxysulfonyl, pyrrolidinylsulfonyl, piperidinylsulfonyl, morpholinylsulfonyl or a radical of the formula CO—Ar, CO—OAlk, CO—NHAr, CO—N(Ar)Alk, CO—$N(Alk)_2$, $SO_2$—Alk, $SO_2$—OAr, $SO_2$—$N(Alk)_2$, $SO_2$—NHAlk, $SO_2$—N(Ar)Alk or $SO_2$—NHAr, $R^5$ is hydrogen, $C_1$–$C_4$-alkyl, halogen or hydroxysulfonyl, and $R^{10}$ is $SO_2$—$CH_2CH$=$CH_2$. $SO_2$—CH=$CH_2$ or $SO_2$—$C_2H_4$—Q and $R^{10}$ is in the 3- or 4-position, and Alk is $C_1$–$C_8$-alkyl which may be interrupted by from 1 to 3 oxygen atoms in ether function or by 1 sulfur atom or 1 sulfonyl group and may be substituted by hydroxyl, $C_1$–$C_4$-alkanoyloxy, benzoyloxy, sulfate, halogen, cyano, carbamoyl, carboxyl, hydroxysulfonyl, phenoxy, phenyl or hydroxysulfonylphenyl, or is $C_5$–$C_8$-cycloalkyl, Ar is phenyl or naphthyl, and each of these radicals may be substituted by $C_1$–$C_4$-alkyl, phenyl-($C_1$–$C_4$)-alkyl, halogen, $C_1$–$C_4$-alkoxy, $C_1$–$C_4$-alkoxy-($C_1$–$C_4$)-alkyl, phenoxy, hydroxy, carboxyl, $C_1$–$C_4$-alkanoylamino with or without interruption by 1 oxygen atom in ether function in the alkyl chain, benzoylamino, hydroxysulfonyl, pyrrolidinylsulfonyl, piperidinylsulfonyl, morpholinylsulfonyl or a radical of the formula $SO_2$—Alk, $SO_2$—$CH_2CH$=$CH_2$, $SO_2$—CH=$CH_2$, SO2—$C_2H_4$—Q, $SO_2$—NHAlk, $SO_2$—N$(alk)_2$, $SO_2$—G, $SO_2$—OG, $SO_2$—NHG or $SO_2$—N(Alk)G, Y is methylene or carbonyl, $Z^1$ is hydrogen or a radical of the formula Alk or Ar, $Z^2$ is hydrogen or hydroxysulfonyl, Q is hydroxyl or an alkali-detachable group, and G is phenyl which may be substituted by $C_1$–$C_4$-alkyl, carboxyl, hydroxysulfonyl or $C_1$–$C_4$-alkanoylamino or is naphthyl which may be substituted by hydroxysulfonyl.

2. The Disazo dye as claimed in claim 1, wherein $R^{10}$ is a radical of the formula $SO_2$—$C_2H_4$—$Q^1$ where $Q^1$ is an alkali-detachable group.

3. The Disazo dye as claimed in claim 1, wherein $R^1$, is an oxadiazole radical.

4. The Disazo dye of the formula I (I)

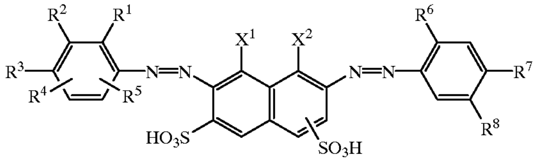

where one of the two radicals $X^1$ and $X^2$ is hydroxyl and the other is amino, $R^1$ is hydrogen, hydroxysulfonyl or a radical of the formula CO—Ar, CO—OAlk, CO—OAr, $SO_2$—Ar, $SO_2$—Alk, $SO_2$—OAr,

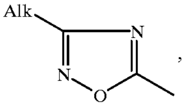 , 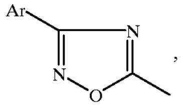 ,

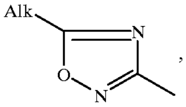 , 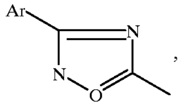 ,

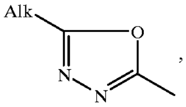 , 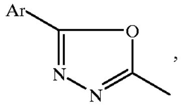 ,

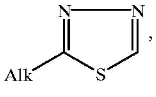 , 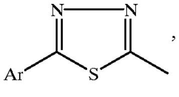 , $R^2$ is hydrogen or $R^2$ and $R^1$ together are a radical of the formula

O—$NZ^1$—CO or

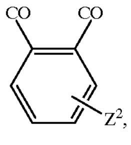, $R^3$ is hydrogen, hydroxysulfonyl, $C_1$–$C_4$-alkyl, halogen or a radical of the formula $SO_2$—OAr, $SO_2$—N(Ar)Alk or $SO_2$—NHAr or $R^3$ and $R^2$ together are a radical of the formula CO—NZ1—Y, $R^4$ is hydrogen, hydroxysulfonyl, pyrrolidinylsulfonyl, piperidinylsulfonyl, morpholinylsulfonyl or a radical of the formula CO—Ar, CO—OAlk, CO—NHAr, CO—N(Ar)Alk, CO—$N(Alk)_2$, $SO_2$—Alk, $SO_2$—OAr, $SO_2$—$N(Alk)_2$, $SO_2$—NHAlk, $SO_2$—N(Ar)Alk or $SO_2$—NHAr, $R^5$ is hydrogen, $C_1$–$C_4$-alkyl, halogen or hydroxysulfonyl, and $R^6$, $R^7$ and $R^8$ are each independently of the others hydrogen, $C_1$–$C_4$-alkyl, halogen, cyano, nitro, hydroxysulfonyl or a radical of the formula CO—Ar, CO—OAr, CO—OAlk, CO—N(Ar)Alk, CO—N(Alk) $_2$, $SO_2$—Ar, $SO_2$—Alk, $SO_2$—$CH_2CH$=$CH_2$, $SO_2$—CH=$CH_2$, $SO_2$—$C_2H_4$—Q, $SO_2$—OAr,

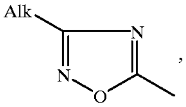 , 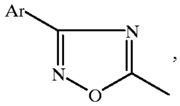 ,

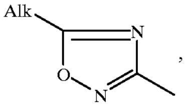 , 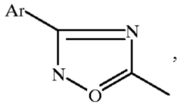 ,

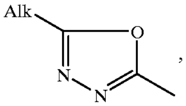 , 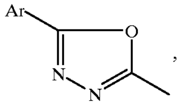 ,

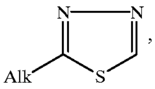 , 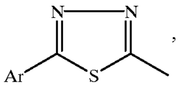 , where

Alk is $C_1$—$C_8$-alkyl which may be interrupted by from 1 to 3 oxygen atoms in ether function or by 1 sulfur atom or 1 sulfonyl group and may be substituted by hydroxyl, $C_1$–$C_4$-alkanoyloxy, benzoyloxy, sulfate, halogen, cyano, carbamoyl, carboxyl, hydroxysulfonyl, phenoxy, phenyl or hydroxysulfonylphenyl, or is $C_5$–$C_8$-cycloalkyl, Ar is phenyl or naphthyl, and each of these radicals may be substituted by $C_1$–$C_4$-alkyl, phenyl-($C_1$–$C_4$)-alkyl, halogen, $C_1$–$C_4$-alkoxy, $C_1$–$C_4$-alkoxy-($C_1$–$C_4$)-alkyl, phenoxy, hydroxy, carboxyl, $C_1$–$C_4$-alkanoylamino with or without interruption by 1 oxygen atom in ether function in the alkyl chain, benzoylamino, hydroxysulfonyl, pyrrolidinylsulfonyl, piperidinylsulfonyl, morpholinylsulfonyl or a radical of the formula $SO_2$—Alk, $SO_2$—$CH_2CH$=$CH_2$, $SO_2$—CH=$CH_2$, SO2—$C_2H_4$—Q, $SO_2$—NHAlk, $SO_2$—N $(alk)_2$, $SO_2$—G, $SO_2$—OG, $SO_2$—NHG or $SO_2$—N (Alk)G, Y is methylene or carbonyl, $Z^1$ is hydrogen or a radical of the formula Alk or Ar, $Z^2$ is hydrogen or hydroxysulfonyl, Q is hydroxyl or an alkali-detachable group, and G is phenyl which may be substituted by $C_1$–$C_4$-alkyl, carboxyl, hydroxysulfonyl or $C_1$–$C_4$-alkanoylamino or is naphthyl which may be substituted by hydroxysulfonyl, and one of the radicals $R^7$ or $R^8$ is a radical of the formula $SO_2—N(Alk)_2$, $SO_2—NHAlk$, $SO_2—N(Ar)Alk$, $SO_2—NHAr$ or pyrrolidinylsulfonyl, piperidinylsulfonyl or morpholinylsulfonyl and the other radical and the radical $R^6$ are each hydrogen or $R^3$ is a radical of the formula $SO_2—N(Ar)Alk$ and the radicals $R^1$, $R^2$, $R^4$ and $R^5$ are each hydrogen.

5. The Disazo dye as claimed in claim 4 containing a radical of the formula $SO_2—C_2H_4—Q^1$ where $Q^1$ is an alkali-detachable group.

6. The Disazo dye as claimed in claim 4, wherein $R^3$ and/or $R^7$ are each a radical of the formula $SO_2—N(Ar)Alk$.

7. The Disazo dye as claimed in claim 4, wherein $R^3$ and/or $R^7$ are each a radical of the formula $SO_2—N(Ar)Alk$ where Ar contains a radical of the formula $SO_2—C_2H_4—Q$, $SO_2—CH═CH_2$ or $SO_2—CH_2—CH═CH_2$.

8. The Disazo dye as claimed in claim 4, wherein $R^1$, $R^6$, $R^7$ or $R^8$ is an oxadiazole radical.

9. A Disazo dye of the formula IV (IV)

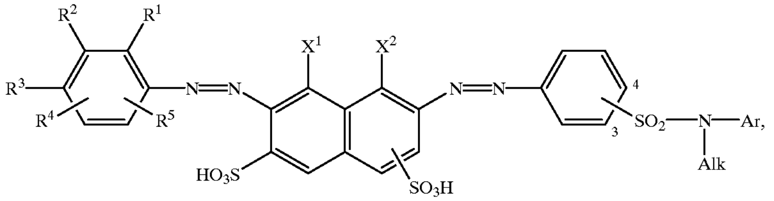

where $R^1$, $R^2$, $R^3$, $R^4$, $R^5$, $X^1$, $X^2$, Alk and Ar are each as defined in claim 4 and the sulfonamide radical is in the 3- or 4-position.

10. A method of dyeing wool at a pH from 3 to 7, which comprises applying thereto a disazo dye as claimed in claim 2.

11. A method of dyeing wool at a pH from 3 to 7, which comprises applying thereto a disazo dye as claimed in claim 5.

12. A method of dyeing a natural or synthetic substrates which comprises applying thereto a disazo dye as claimed in claim 1.

13. A method of dyeing a natural or synthetic substrates which comprises applying thereto a disazo dye as claimed in claim 4.

* * * * *